US010159713B2

(12) United States Patent
Belder et al.

(10) Patent No.: US 10,159,713 B2
(45) Date of Patent: Dec. 25, 2018

(54) TREATMENT OF TYPE 2 DIABETES MELLITUS PATIENTS

(71) Applicant: Sanofi-Aventis Deutschland GmbH, Frankfurt am Main (DE)

(72) Inventors: Rene Belder, Bridgewater, NJ (US); Peter Johnston, Barryville, NY (US); Francesca Lawson, Bridgewater, NJ (US); Lin Ping, Bridgewater, NJ (US); Xiaodan Wei, Bridgewater, NJ (US)

(73) Assignee: Sanofi-Aventis Deutschland GmbH (DE)

( * ) Notice: Subject to any disclaimer, the term of this patent is extended or adjusted under 35 U.S.C. 154(b) by 0 days.

(21) Appl. No.: 15/073,364

(22) Filed: Mar. 17, 2016

(65) Prior Publication Data

US 2016/0296601 A1    Oct. 13, 2016

(30) Foreign Application Priority Data

Mar. 18, 2015  (EP) .................................. 15159733
Oct. 27, 2015  (EP) .................................. 15191585

(51) Int. Cl.
| | | |
|---|---|---|
| A61K 38/26 | (2006.01) | |
| A61P 3/10 | (2006.01) | |
| A61P 5/50 | (2006.01) | |
| A61P 9/10 | (2006.01) | |
| A61P 13/12 | (2006.01) | |

(52) U.S. Cl.
CPC .................................. A61K 38/26 (2013.01)

(58) Field of Classification Search
None
See application file for complete search history.

(56) References Cited

U.S. PATENT DOCUMENTS

| | | | |
|---|---|---|---|
| 3,758,683 | A | 9/1973 | Jackson |
| 3,868,358 | A | 2/1975 | Jackson |
| 4,153,689 | A | 5/1979 | Hirai et al. |
| 4,165,370 | A | 8/1979 | Coval |
| 4,258,134 | A | 3/1981 | Yoshida et al. |
| 4,367,737 | A | 1/1983 | Kozam et al. |
| 4,608,364 | A | 8/1986 | Grau |
| 4,614,730 | A | 9/1986 | Hansen et al. |
| 4,644,057 | A | 2/1987 | Bicker et al. |
| 4,689,042 | A | 8/1987 | Sarnoff et al. |
| 4,701,440 | A | 10/1987 | Grau |
| 4,731,405 | A | 3/1988 | Kirsch et al. |
| 4,783,441 | A | 11/1988 | Thurow |
| 4,839,341 | A | 6/1989 | Massey et al. |
| 4,863,902 | A | 9/1989 | Amagase et al. |
| 4,885,164 | A | 12/1989 | Thurow |
| 4,923,162 | A | 5/1990 | Fleming et al. |
| 4,959,351 | A | 9/1990 | Grau |
| 4,960,702 | A | 10/1990 | Rice et al. |
| 4,994,439 | A | 2/1991 | Longenecker et al. |
| 5,008,241 | A | 4/1991 | Markussen et al. |
| 5,034,415 | A | 7/1991 | Rubin |
| 5,070,186 | A | 12/1991 | Joergensen |
| 5,101,013 | A | 3/1992 | Doerschug et al. |
| 5,177,058 | A | 1/1993 | Doerschug |
| 5,187,177 | A | 2/1993 | Garzaran |
| 5,227,293 | A | 7/1993 | Stengelin et al. |
| 5,253,785 | A | 10/1993 | Haber et al. |
| 5,272,135 | A | 12/1993 | Takruri |
| 5,358,708 | A | 10/1994 | Patel |
| 5,358,857 | A | 10/1994 | Stengelin et al. |
| 5,370,629 | A | 12/1994 | Michel et al. |
| 5,397,771 | A | 3/1995 | Bechgaard et al. |
| 5,407,609 | A | 4/1995 | Tice et al. |
| 5,424,286 | A | 6/1995 | Eng |
| 5,428,006 | A | 6/1995 | Bechgaard et al. |
| 5,473,049 | A | 12/1995 | Obermeier et al. |
| 5,474,978 | A | 12/1995 | Bakaysa et al. |
| 5,478,323 | A | 12/1995 | Westwood et al. |
| 5,496,924 | A | 3/1996 | Habermann et al. |
| 5,506,203 | A | 4/1996 | Baeckstroem et al. |
| 5,509,905 | A | 4/1996 | Michel |
| 5,514,646 | A | 5/1996 | Chance et al. |
| 5,524,286 | A | 6/1996 | Chiesa et al. |
| 5,534,488 | A | 7/1996 | Hoffmann |
| 5,545,618 | A | 8/1996 | Buckley et al. |
| 5,547,929 | A | 8/1996 | Anderson, Jr. et al. |
| 5,559,094 | A | 9/1996 | Brems et al. |
| 5,595,756 | A | 1/1997 | Bally et al. |
| 5,597,796 | A | 1/1997 | Brange |
| 5,614,219 | A | 3/1997 | Wunderlich et al. |
| 5,614,492 | A | 3/1997 | Habener |
| 5,631,224 | A | 5/1997 | Efendic et al. |

(Continued)

FOREIGN PATENT DOCUMENTS

| | | | |
|---|---|---|---|
| AU | 593274 B2 | 2/1990 | |
| AU | 612324 B2 | 7/1991 | |

(Continued)

OTHER PUBLICATIONS

18th World Health Congress (Helsinki). WMA Declaration of Helsinki—Ethical Principles for Medical Research Involving Human Subjects; WMA; Jun. 1964, pp. 1-8.

Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.

Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.

Actrapid® prescribing information, Apr. 2011, pp. 1-4.

(Continued)

Primary Examiner — Julie Ha
Assistant Examiner — Kristina M Hellman
(74) Attorney, Agent, or Firm — Lathrop Gage LLP; James V. DeGiulio

(57) ABSTRACT

The present invention refers to lixisenatide for use in the reduction of progression of urinary albumin excretion in a type 2 diabetes mellitus patient.

17 Claims, 4 Drawing Sheets

Figure 1:
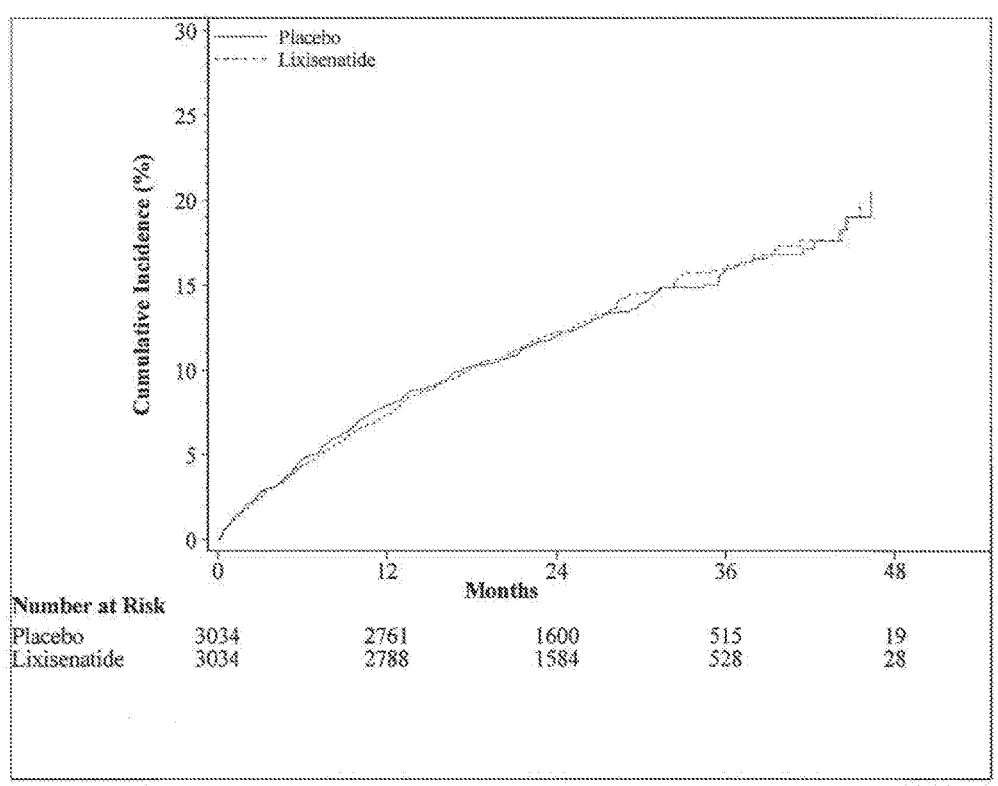

Specification includes a Sequence Listing.

(56) References Cited

U.S. PATENT DOCUMENTS

| | | |
|---|---|---|
| 5,654,008 A | 8/1997 | Herbert et al. |
| 5,656,722 A | 8/1997 | Dorschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti et al. |
| 5,935,566 A | 8/1999 | Yuen et al. |
| 5,948,751 A | 9/1999 | Kimer et al. |
| 5,952,297 A | 9/1999 | De Felippis et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,410,511 B2 | 6/2002 | L'Italien et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,737,401 B2 | 5/2004 | Kim et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Doerschug et al. |
| 6,902,744 B1 | 6/2005 | Kolterman et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 8,901,484 B2 | 12/2014 | Vogel et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | Defelippis et al. |
| 2003/0170691 A1 | 9/2003 | Gimeno et al. |
| 2003/0212248 A1 | 11/2003 | Furman |
| 2004/0022792 A1 | 2/2004 | Klinke |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | Defelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0104210 A1 | 4/2009 | Tota et al. |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |

(56) References Cited

U.S. PATENT DOCUMENTS

| | | |
|---|---|---|
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0122776 A1 | 5/2012 | Graefe-Mody et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0317477 A1 | 11/2013 | Edwards et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |
| 2014/0379277 A1 | 12/2014 | Vogel et al. |
| 2016/0199452 A1 | 7/2016 | Souhami et al. |
| 2016/0235818 A1 | 8/2016 | Bergmann et al. |
| 2016/0287674 A1 | 10/2016 | Roy et al. |
| 2016/0296601 A1 | 10/2016 | Belder et al. |

FOREIGN PATENT DOCUMENTS

| | | |
|---|---|---|
| AU | 200072263 | 2/2001 |
| CA | 1173388 A | 8/1984 |
| CA | 1258427 A | 8/1989 |
| CA | 1336329 C | 7/1995 |
| CA | 1341203 C | 3/2001 |
| CA | 2 685 638 | 5/2011 |
| CN | 1276731 A | 12/2000 |
| CN | 1413582 A | 4/2003 |
| CN | 1662252 A | 8/2005 |
| CN | 101366692 A | 2/2009 |
| CN | 101444618 A | 6/2009 |
| CN | 101454019 A | 6/2009 |
| CN | 101670096 A | 3/2010 |
| DE | 19637230 A1 | 3/1998 |
| DE | 102008003566 A1 | 7/2009 |
| DE | 102008003568 A1 | 7/2009 |
| DE | 102008053048 A1 | 4/2010 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0200383 A2 | 11/1986 |
| EP | 0211299 A2 | 2/1987 |
| EP | 0214826 A2 | 3/1987 |
| EP | 0224885 A1 | 6/1987 |
| EP | 0227938 A2 | 7/1987 |
| EP | 0229998 A2 | 7/1987 |
| EP | 0254516 A2 | 1/1988 |
| EP | 0368187 A2 | 5/1990 |
| EP | 0375437 A2 | 6/1990 |
| EP | 0383472 A2 | 8/1990 |
| EP | 0194864 B1 | 6/1992 |
| EP | 0419504 B1 | 1/1994 |
| EP | 0600372 A1 | 6/1994 |
| EP | 0668282 A1 | 8/1995 |
| EP | 0678522 A1 | 10/1995 |
| EP | 0837072 A2 | 4/1998 |
| EP | 0845265 A1 | 6/1998 |
| EP | 0885961 A1 | 12/1998 |
| EP | 1076066 A1 | 2/2001 |
| EP | 1172114 A2 | 1/2002 |
| EP | 1222207 A1 | 7/2002 |
| EP | 1523993 A1 | 4/2005 |
| EP | 2112161 A2 | 10/2009 |
| EP | 2324853 A1 | 5/2011 |
| EP | 2329848 A1 | 6/2011 |
| EP | 2389945 A1 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | H02264798 A | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2006137678 A | 6/2006 |
| JP | 2007204498 A | 8/2007 |
| JP | 2009091363 A | 4/2009 |
| RU | 2386631 C2 | 4/2010 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO-9200321 A1 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO-9632414 A1 | 10/1996 |
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO-9805351 A1 | 2/1998 |
| WO | WO-9808531 A1 | 3/1998 |
| WO | WO-9808871 A1 | 3/1998 |
| WO | WO-9808873 A1 | 3/1998 |
| WO | WO-9819698 A1 | 5/1998 |

(56) References Cited

FOREIGN PATENT DOCUMENTS

| | | |
|---|---|---|
| WO | WO-9830231 A1 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO-9907404 A1 | 2/1999 |
| WO | WO-9921573 A1 | 5/1999 |
| WO | WO-9921578 A1 | 5/1999 |
| WO | WO-9924071 A1 | 5/1999 |
| WO | WO-9925727 A2 | 5/1999 |
| WO | WO-9925728 A1 | 5/1999 |
| WO | WO-9940788 A1 | 8/1999 |
| WO | WO-9943708 A1 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0072582 A1 | 11/2000 |
| WO | WO-0074736 A1 | 12/2000 |
| WO | WO-0100223 A2 | 1/2001 |
| WO | WO-0102039 A1 | 1/2001 |
| WO | WO-0104156 A1 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO 01/32157 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO-03020201 A2 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO-2004005342 A1 | 1/2004 |
| WO | WO-2004035623 A2 | 4/2004 |
| WO | WO 2004/050115 | 6/2004 |
| WO | WO-2004045592 A2 | 6/2004 |
| WO | WO-2004064862 A1 | 8/2004 |
| WO | WO-2004078196 A1 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO-2004105781 A2 | 12/2004 |
| WO | WO-2004107979 A1 | 12/2004 |
| WO | WO-2005021022 A2 | 3/2005 |
| WO | WO-2005023291 A2 | 3/2005 |
| WO | WO-2005028516 A2 | 3/2005 |
| WO | WO-2005046716 A1 | 5/2005 |
| WO | WO-2005048950 A2 | 6/2005 |
| WO | WO-2005112949 A1 | 12/2005 |
| WO | WO-2005117948 A1 | 12/2005 |
| WO | WO-2006000567 A2 | 1/2006 |
| WO | 2006/017541 | 2/2006 |
| WO | WO-2006015879 A1 | 2/2006 |
| WO | WO-2006029634 A2 | 3/2006 |
| WO | WO-2006051103 A2 | 5/2006 |
| WO | WO-2006051110 A2 | 5/2006 |
| WO | WO-2006058620 A2 | 6/2006 |
| WO | WO-2006110551 A2 | 10/2006 |
| WO | WO-2007001150 A2 | 1/2007 |
| WO | WO-2007006307 A2 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO 2007/081792 | 7/2007 |
| WO | WO-2007075534 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A1 | 1/2008 |
| WO | WO-2008021560 A2 | 2/2008 |
| WO | WO-2008023050 A1 | 2/2008 |
| WO | WO-2008028914 A1 | 3/2008 |
| WO | WO-2008034881 A2 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO-2009039963 A1 | 4/2009 |
| WO | WO-2009048959 A1 | 4/2009 |
| WO | WO-2009056569 A1 | 5/2009 |
| WO | WO-2009063072 A2 | 5/2009 |
| WO | WO-2009087081 A2 | 7/2009 |
| WO | WO-2009089181 A1 | 7/2009 |
| WO | WO-2009098318 A1 | 8/2009 |
| WO | WO-2009102467 A2 | 8/2009 |
| WO | WO-2009134380 A2 | 11/2009 |
| WO | WO-2009143014 A1 | 11/2009 |
| WO | WO-2010030670 A2 | 3/2010 |
| WO | WO-2010043566 A2 | 4/2010 |
| WO | WO-2010044867 A1 | 4/2010 |
| WO | WO 2010/089304 | 8/2010 |
| WO | WO-2010092163 A2 | 8/2010 |
| WO | WO 2010/138671 | 12/2010 |
| WO | WO-2011012719 A1 | 2/2011 |
| WO | WO-2011017554 A2 | 2/2011 |
| WO | WO-2011029892 A2 | 3/2011 |
| WO | WO-2011058082 A1 | 5/2011 |
| WO | WO-2011058083 A1 | 5/2011 |
| WO | WO-2011089203 A1 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A1 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | WO-2012156296 A1 | 11/2012 |

(56) References Cited

FOREIGN PATENT DOCUMENTS

| WO | WO-2012156299 A1 | 11/2012 |
|----|------------------|---------|
| WO | WO-2012177929 A2 | 12/2012 |
| WO | WO-2013060850 A1 | 5/2013 |
| WO | WO-2014017849 A1 | 1/2014 |
| WO | WO-2014118355 A1 | 8/2014 |
| WO | 2014/131815 | 9/2014 |
| WO | WO-2014202483 A1 | 12/2014 |
| WO | WO 2015/059302 | 4/2015 |

OTHER PUBLICATIONS

Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Ahualli J., "The Double Duct Sign," Radiology, 2007, vol. Jul. 244 (1), pp. 314-315.
Akbar D.H., "Sub-Optimal Postprandial Blood Glucose Level in Diabetics Attending the Outpatient Clinic of a University Hospital," Saudi Med Journal, Oct. 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
American Diabetes Association, "Type 2 Diabetes in Children and Adolescents," Diabetes Care, Mar. 2000, vol. 23 (3), pp. 381-389.
American Diabetes Association, "Standards of Medical Care in Diabetes—2011," Diabetes Care, Jan. 2011, vol. 34 (Suppl 1), pp. S11-S61.
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.
Aquiliante C.L., "Sulfonylurea Pharmacogenomics in Type 2 Diabetes: The Influence of Drug Target and Diabetes Risk Polymorphisms," Expert Review of Cardiovascular Therapy, Mar. 2010, vol. 8 (3), pp. 359-372.
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, Jun. 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, Nov. 2007, vol. 29 (11), pp. 2333-2348.
Barnett A.H., "Insulin Glargine in the Treatment of Type 1 and Type 2 Diabetes," Vascular Health and Risk Management, Published Jan. 25, 2006, vol. 2 (1), pp. 59-67.
Barnett A.H., "Lixisenatide: Evidence for its Potential Use in the Treatment of Type 2 Diabetes," Core Evidence, Published Online Sep. 8, 2011, vol. 6, pp. 67-79.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, May 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.
Bethel M.A., et al., "Basal Insulin Therapy in Type 2 Diabetes," The Journal of the American Board of the Family Practice, May-Jun. 2005, vol. 18 (3), pp. 199-204.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, Jun. 29, 1996, vol. 312 (7047), pp. 1654.
Bolen et al., "Systematic Review: Comparative Effectiveness and Safety of oral Medications for Type 2 Diabetes Mellitus," Annals of Internal Medicine, Epub Jul. 16, 2007, vol. 147 (6), pp. 386-399.
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli G.B., et al., "Efficacy and Safety of Lixisenatide once Daily Vs Placebo in People with Type 2 Diabetes Insufficiently Controlled on Metformin (Getgoal-F1)," Diabetic Medicine, Published Online Oct. 24, 2014, vol. 31 (2), pp. 176-184.
Bolli G.B., "The Pharmacokinetic Basis of Insulin Therapy in Diabetes Mellitus," Diabetes Research and Clinical Practice, May 1989, vol. 6 (4), pp. S3-15.
Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.
Boutajangout A., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange "Galenics of Insulin" 1987, p. 35-36.
Brange J., et al., "Chemical Stability of Insulin 3. Influence of Excipients, formulation, and Ph," Acta Pharmaceutica Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112. Abstract only submitted.

(56) References Cited

OTHER PUBLICATIONS

Brange J., et al., "Monomeric Insulins and their Experimental and Clinical Implications," Diabetes Care, Sep. 1990, vol. 13 (9), pp. 923-954.
Brange J., et al., "Neutral Insulin Solutions Physically Stabilized by Addition of Zn2+," Diabetic Medicine, Nov.-Dec. 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.
Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.
Broderick J., et al., "Guidelines for the Management of Spontaneous intracerebral Hemorrhage in Adults," Circulation, 2007, vol. 116 (16), pp. e391-e413.
Brown J.B., et al., "Slow Response to Loss of Glycemic Control in Type 2 Diabetes Mellitus," American Journal of Managed Care, 2003, vol. 9 (3), pp. 213-217.
"Buffer" Oxford Dictionary of Biochemistry and Molecular Biology, Oxford University Press, 2001, p. 83.
Burgermeister W., et al., "The Isolation of Insulin from the Pancreas," Insulin, 1975, vol. Part 2, pp. 715-727.
Burke G.T., et al., "Nature of the B10 Amino Acid Residue Requirements for High Biological Activity of Insulin," International Journal of Peptide and Protein Research, 1984, vol. 23 (4), pp. 394-401.
Buse J.B., et al., "Use of Twice-Daily Exenatide in Basal Insulin-Treated Patients with Type 2 Diabetes: A Randomized, Controlled Trial," Annals of Internal Medicine, Jan. 2011, vol. 154 (2), pp. 103-112.
BYETTA—Summary of Product Characteristics, updated Jan. 27, 2015, last accessed Apr. 18, 2015, pp. 1-12.
Byrne M.M., et al., "Inhibitory Effects of Hyperglycaemia on Fed Jejunal Motility: Potential Role of Hyperinsulinaemia," European Journal of Clinical Investigation, 1998, vol. 28 (1), pp. 72-78.
Cadario B., "SITAGLIPTIN," Drug Information Perspectives, 2010, vol. 30 (4), pp. 1-6.
Campas C., et al., "Ave-0010 GLP-1 Receptor Agonist Treatment of Diabetes," Drugs of the Future, Oct. 2008, vol. 33 (10), pp. 838-840.
Campbell R.K., et al., "Insulin Glargine," Clinical Therapeutics, 2001, vol. 23 (12), pp. 1938-1957.
Canadian Cardiovascular Society Grading of Angina Pectoris, From http://www.sscts.org/pages/Classificationanginaccs.aspx. Accessed May 27, 2016, one page.
Canadian Diabetes Association, Clinical Practice Guidelines Expert Committee, Canadian Diabetes Association 2008, Clinical Practice Guidelines for the Prevention and Management of Diabetes in Canada, Canadian Journal of Diabetes, 2008, pp. S162-S167.
Cannon P.C., et al., "Intensive versus Moderate Lipid Lowering with Statins alter Acute Coronary Syndromes." New England Journal Medicine, Apr. 2004; Epub 2004 Mar. 8, 2004, vol. 350 (15), pp. 1495-1504.
Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.
Centers for Disease Control and Prevention, National Diabetes Fact Sheet: General Information and National Estimates on Diabetes in the United States, 2003, Revolution Education Atlanta, GA: U.S. Department of Health and Human Services, Centers for Disease Control and Prevention, 2004, pp. 1-8.
Chancel, "Natixis Conference on Diabetes." Sanofi, Paris, pp. 1-23 (Nov. 8, 2011).
Charles M.A., et al., "Prevention of Type 2 Diabetes: Role of Metformin," Drugs, Sep. 1999, vol. 58 (Suppl 1), pp. 71-73.

Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.
Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.
Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.
Chi E.Y., Excipients and their Effects on the Quality of Biologics, Available online at https://www.aaps.org/uploadedFiles/Content!Sections_and_Groups/Sections/Formulation_Design_And_Development_Section/FDDTechCornerMay2012.pdf, 9 pages (2012.
Childs B.P., et al., "Defining and Reporting Hypoglycemia in Diabetes: A Report from the American Diabetes Association Workgroup on Hypoglycemia," Diabetes Care, May 2005, vol. 28 (5), pp. 1245-1249.
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D10E80-887D-49A7-B3BB-0517D38CE757, accessed on May 14, 2014, pp. 1-12.
Christensen M., et al., "Lixisenatide, A Novel GLP-1 Receptor Agonist for the Treatment of Type 2 Diabetes Mellitus," IDrugs: The Investigational Drugs Journal, Aug. 2009, vol. 12 (8), pp. 503-513.
Christensen M., et al., "Lixisenatide for Type 2 Diabetes Mellitus," Expert Opinion on Investigational Drugs, Epub Mar. 11, 2011, vol. 20 (4), pp. 549-557.
Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Cochran E., et al., "The Use of U-500 in Patients with Extreme Insulin Resistance," Diabetes Care, 2005, vol. 28 (5), pp. 1240-1244.
Colclough et al., Abstract "Levels of FPG and HbA1 c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo P.A., et al., "Postprandial Plasma-Glucose and -Insulin Responses to Different Complex Carbohydrates," Diabetes, Dec. 1977, vol. 26 (12), pp. 1178-1183.
Croom K.F., et al., "Liraglutide a Review of its Use in Type 2 Diabetes Mellitus," Drugs, 2009, vol. 69 (14), pp. 1985-2004.
Cryer P.E., "Hypoglycemia Is the Limiting Factor in the Management of Diabetes," Diabetes/Metabolism Research and Reviews, Jan.-Feb. 1999, vol. 15 (1), pp. 42-46.
Cvetkovic R.S., et al., "Exenatide A Review of its Use in Patients with Type 2 Diabetes Mellitus (As an Adjunct to Metformin and/or a Sulfonylurea)," Drugs, 2007, vol. 67 (6), pp. 935-954.
Czech C., et al., "Proteolytical Processing of Mutated Human Amyloid Precursor Protein in Transgenic Mice," Brain Research Molecular Brain Research, 1997, vol. 47 (1-2), pp. 108-116.
D'Alessio D., "GLP-1 Receptor Agonists: Strategies for PPG Control," Medical Nursing Education, Jan. 2011, vol. 3, pp. 1-26.
D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.

(56) References Cited

OTHER PUBLICATIONS

Das., et al., "The British Cardiac Society Working Group Definition of Myocardial Infarction: Implications for Practice," Heart, 2005, vol. 92 (1), pp. 21-26, Jan. 2006; Epub Apr. 14, 2005.
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.
De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.
De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.
Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.
Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of Phase, Clinical Trials.gov NIH, accessed, Mar. 2016, one page.
Definition of sphincter of pancreatic duct in the Medical Dictionary, http://medicaldictionary.thefreedictionary.com/, accessed on May 22, 2014, pp. 1-2.
Defronzo R.A., et al., "Effects of Exenatide (Exendin-4) on Glycemic Control and Weight Over 30 Weeks in Metformin-Treated Patients with Type 2 Diabetes," Diabetes care, May 2005, vol. 28 (5), pp. 1092-1100.
Defronzo R.A., "Pathogenesis of Type 2 Diabetes: Implications for Metformin," Drugs, Sep. 1999, vol. 58 (Suppl 1), pp. 29-30.
Defronzo R.A., "Pharmacologic therapy for Type 2 Diabetes Mellitus," Annals of Internal Medicine, 1999, vol. 131 (4), pp. 281-303.
Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.
Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.
Dewitt D.E., "Case Study: Treating New on-Set Catabolic Type 2 Diabetes with Glargine and Lispro," Clinical Diabetes, Oct. 2006, vol. 24 (4), pp. 180-181.
Diabetes Control and Complications Trial/ Epidemiology of Diabetes Interventions and Complications Research Group, "Intensive Diabetes Treatment and Cardiovascular Disease in Patients with Type 1 Diabetes," New England Journal Medicine, Dec. 2005, vol. 353 (25), pp. 2643-2259.
Diabetes Control and Complications Trial, "Intensive diabetes therapy and carotid intima-media thickness in type 1 diabetes," New England Journal Medicine Jun. 2003, vol. 348 (23), pp. 2294-2303.
Diabetes Prevention Program Research Group, "Reduction in the incidence of Type 2 Diabetes with Lifestyle intervention or Metformin," The New England Journal of Medicine, 2002, vol. 346 (6), pp. 393-403.

Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon G.H., et al., "Regeneration of Insulin Activity from the Separated and inactive A and B Chains," Nature, 1960, vol. 188 (4752), pp. 721-724.
Donelli G., et al., "Plastic Biliary Stent Occlusion: Factors Involved and Possible Preventive Approaches," Clinical Medicine & Research, 2007, vol. 5 (1), pp. 53-60.
Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, Oct. 8, 2005, vol. 366 (9493), pp. 1279-1289.
Doyle M.E. et al., "Mechanisms of Action of Glucagon-Like Peptide 1 in the Pancreas," Pharmacology & Therapeutics, Mar. 2007, vol. 113 (3), pp. 546-593.
Drucker D.J. et al., "The incretin System: Glucagon-Like Peptide-1 Receptor Agonists and Dipeptidyl Peptidase-4 inhibitors in Type 2 Diabetes," Lancet, Nov. 11, 2006, vol. 368 (9548), pp. 1696-1705.
Drucker D.J., "Glucagon-Like Peptides," Diabetes, 1998, vol. 47 (2), pp. 159-169.
Drucker D.J., "Mini Review: The Glucagon-Like Peptides," Endocrinology, 2001, vol. 142 (2), pp. 521-527.
Drucker D.J., "The Biology of Lncretin Hormones," Cell Metabolism, 2006, vol. 3 (3), pp. 153-165.
Druet C., et al., "Characterization of Insulin Secretion and Resistance in Type 2 Diabetes of Adolescents," The Journal of Clinical Endocrinology & Metabolism, Feb. 2006, vol. 91 (2), pp. 401-404 (Epub Nov. 15, 2005).
DrugBank, "Insulin glargine," available online at http://www.drugbank.ca/drugs/DB00047, 16 pages (accessed online Sep. 25, 2014).
Drury P.L., et al., "Diabetic Nephropathy," British Medical Bulletin, 1989, vol. 45 (1), pp. 127-147.
Dubois B., et al., "Revising the Definition of Alzheimer's Disease: A New Lexicon," Lancet Neurology, 2010, vol. 9 (11), pp. 1118-1127.
Dunn C.J., et al., "Insulin Glargine: An Updated Review of its Use in the Management of Diabetes Mellitus," Drugs, 2003, vol. 63 (16), pp. 1743-1778.
During M.J., et al., "Glucagon-Like Peptide-1 Receptor is involved in Learning and Neuroprotection," Nature Medicine, 2003, vol. 9 (9), pp. 1173-1179.
Eckert A., et al., "Alzheimer's Disease-Like Alterations in Peripheral Cells from Presenilin-1 Transgenic Mice," Neurobiology of Disease, 2001, vol. 8 (2), pp. 331-342.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6017; Clinical Trial Eudra CT No. 2007-005884-92, accessed Apr. 24, 2015, one page.
EFC6018; Clinical trial EudraCT 2007-005887-29, "Getgoal-Mono" accessed Jul. 27, 2014; pp. 1-16.
EMA—Science Medicines Health "TOUJEO" EPAR Summary for the Public, first published Nov. 5, 2009, pp. 1-3.
EMA—European Medicines Agency, "Note for guidance on non-clinical safety studies for the conduct of human clinical Trials and marketing authorization for pharmaceuticals," Jul. 2008, pp. 1-22.
EMA Press Release, "European Medicines Agency recommends suspension of Avandia, Avandamet and Avaglim" pp. 1-2 (Sep. 23, 2010).
Eng J., et al., "Isolation and Characterization of Exendin-4, An Exendin-3 Analogue, from Heloderma Suspectum Venom Further Evidence for an Exendin Receptor on Dispersed Acini from Guinea Pig Pancreas," The Journal of Biological Chemistry, 1992, vol. 267 (11), pp. 7402-7405.

(56) References Cited

OTHER PUBLICATIONS

English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
English translation of the TIPO Search Report for ROC Patent Application No. 104116749, dated Feb. 22, 2016, One page.
English translation of the TIPO Search Report for ROC Patent Application No. 101131466; dated Mar. 2, 2016, one pag.
English Translation of TIPO Search Report for ROC Patent Application No. 101130936, dated Dec. 1, 2015, one page.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
European Medicines Agency, Committee for Medicinal Products for Human Use (CHMP), "Assessment Report—Lyxumia", Nov. 28, 2012, pp. 1-81.
European Medicines Agency, "Toujeo (previously Optisulin) insulin glargine," <http:index.jsp?curl="pages/medicines/human/medicines/000309/human_med_000955.jsp&mid=WC0b01ac058001d124" >, last updated Jan. 25, 2016, visited Feb. 3, 2016, pp. 1-6— screenshot of "About" tab of webpage and printouts f "About" tab of webpage with listed items collapsed and expanded.</http: >.
European Public Assessment Report (EPAR) Optisulin EPAR Summary for the Public. Feb. 2009, pp. 1-3.
Ex Parte Herrmann, Appeal No. 2009-001777 U.S. Appl. No. 10/616,457 (B. Pai. Nov. 13, 2009).
Executive Summary, "Standards of Medical Care in Diabetes— 2009" Diabetes Care,32(Suppl. 1):S6-S12 (Jan. 2009).
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; of Aug. 18, 2014, pp. 1-6.
Extended European Search Report for European Application No. 14 19 7154.9: dated Apr. 8, 2015, pp. 1-7.
Extended European Search Report for European Application No. 15159064.3, dated Oct. 19, 2015, pp. 1-4.
Fabunmi R., et al., "Patient Characteristics, Drug Adherence Patterns, and Hypoglycemia Costs for Patients with Type 2 Diabetes Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, Aug. 2010, vol. 164 (1), pp. 40-41.
FDA—Food and Drug Administration, CFR-Code of Federal Regulations Title 21, Chapter 1, Subchapter D, Part 312.21, "Phases of an investigation," Apr. 1, 2015, pp. 1-2.

FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (CDER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liraglutide (Nn2211), a Long-Acting GLP-1 Analogue, on Glycaemic Control and Bodyweight in Subjects with Type 2 Diabetes," Diabetic Medicine, Jul. 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/123,835; dated Feb. 12, 2013, pp. 1-13.
Final Office Action issued in U.S. Appl. No. 13/602,913; dated Apr. 2, 2015, pp. 1-7.
Final Office Action issued in U.S. Appl. No. 13/602,913; dated Jun. 20, 2014, pp. 1-27.
Final Office Action issued in U.S. Appl. No. 13/602,913; dated Sep. 13, 2013, pp. 1-11.
Final Office Action issued in U.S. Appl. No. 12/617,805; dated May 25, 2016, pp. 1-9.
Final Office Action issued in U.S. Appl. No. 13/382,442; dated Aug. 11, 2015, pp. 1-35.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. No. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/363,956; dated May 20, 2014, pp. 1-16.
Final Rejection issued in U.S. Appl. No. 13/382,442; dated Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.
Final Rejection issued in U.S. Appl. No. 13/382,772; dated Feb. 10, 2015, pp. 1-36.
Final Rejection issued in U.S. Appl. No. 13/467,707; dated Feb. 12, 2016, pp. 1-12.
Final Rejection issued in U.S. Appl. No. 13/467,707; dated Feb. 25, 2014, pp. 1-18.
Final Rejection issued in U.S. Appl. No. 13/467,707; dated Jan. 7, 2015, pp. 1-8.
Final Rejection issued in U.S. Appl. No. 13/468,422; dated Jan. 6, 2014, pp. 1-21.
Final Rejection issued in U.S. Appl. No. 13/468,422; dated Jan. 23, 2015, pp. 1-27.

(56) References Cited

OTHER PUBLICATIONS

Final Rejection issued in U.S. Appl. No. 13/469,633; dated Dec. 4, 2013, pp. 1-17.
Final Rejection issued in U.S. Appl. No. 13/469,633; dated Jan. 23, 2015, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542, dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/661,476, dated Oct. 2, 2014, pp. 1-33.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/819,114; dated Mar. 2, 2015, pp. 1-10.
Final Rejection issued in U.S. Appl. No. 13/382,772; dated Feb. 24, 2016, pp. 1-36.
Final Rejection issued in U.S. Appl. No. 14/303,895; dated Apr. 27, 2015, pp. 1-10.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Final-Rejection issued in U.S. Appl. No. 13/432,811; dated Sep. 6, 2014, pp. 1-8.
Final Rejection issued in U.S. Appl. No. 13/509,542, dated Feb. 10, 2016, pp. 1-40.
Final-Rejection issued in U.S. Appl. No. 13/432,811; dated Feb. 10, 2016, pp. 1-9.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Forman J.P., et al., "Higher Levels of Albuminuria within the Normal Range Predict Incident Hypertension." Journal of American Social Nephrology, Oct. 2008, vol. 19 (10), pp. 1983-1988.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, Aug. 1996, vol. 13 (8), pp. 1252-1257.
Galloway J.A., et al., "New forms of Insulin," Diabetes, 1972, vol. 21 (2 Suppl), pp. 637-648.
Gallwitz B., "Liraglutide. GLP-1 Receptor Agonist Treatment of Type 2 Diabetes Treatment of Obesity," Drugs of the Future, Jan. 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber A., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, Feb. 7, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, Jun. 10, 2008; published online Mar. 29, 2008, vol. 587 (1-3), pp. 112-117.
Gavin J.R., "Report of the Expert Committee on the Diagnosis and Classification of Diabetes Mellitus," Diabetes Care, Jul. 1997, vol. 20 (7), pp. 1183-1197.
Geiger R., "The Chemistry of Insulin," Chemiker Zeitung, Jan. 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.
Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.
Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.
Goke R., et al., "Exendin-4 is a High Potency Agonist and Truncated Exendin-(9-39)-Amide an Antagonist at the Glucagon-Like Peptide 1-(7-36)-Amide Receptor of Insulin-Secreting Beta-Cells," The Journal of Biological Chemistry, 1993, vol. 268 (26), pp. 19650-19655.
Goldstein D.E., et al., "Tests of Glycemia in Diabetes," Diabetes Care, Jun. 1995, vol. 18 (6), pp. 896-909.
Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.
Goykhman S., et al., "Insulin Glargine: A Review 8 Years After its introduction," Expert Opinion on Pharmacotherapy, 2009, vol. 10 (4), pp. 705-718.
Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.
Gura T., "Systems for Identifying New Drugs Are often Faulty," Science, 1997, vol. 278 (5340), pp. 1041-1042.
Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.
Gygi S.P., et al, "Quantitative Analysis of Complex Protein Mixtures Using Isotope-Coded Affinity Tags," Nature Biotechnology, Oct. 1999, vol. 17 (10), pp. 994-999.
Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.
Hamilton A., et al., "Receptors for the incretin Glucagon-Like Peptide-1 are Expressed on Neurons in the Central Nervous System," NeuroReport, 2009, vol. 20 (13), pp. 1161-1166.
Hanas R., et al., "2010 Consensus Statement on the Worldwide Standardization of the Hemoglobin A1C Measurement," Diabetes Care, Aug. 2010, vol. 33 (8), pp. 1903-1904.
Hanefeld M., et al., "The Postprandial State and the Risk of Atherosclerosis," Diabetic Medicine, 1997, vol. 14 (Suppl 3), pp. S6-S11.
Hanefeld M., "Normnahe Postprandiale Hyperglykamie-Eine Essenzielle Komponente Guter Diabeteskontrolle Und Pravention Kardiovaskularer

(56) References Cited

OTHER PUBLICATIONS

Erkrankungen (Near-Normal Postprandial Hyperglycemia—An Essential Component of Good Diabetes Control and Prevention of Cardiovascular Diseases)," Paul Langerhans Lecture Diabetologie und Stoffinfechsel, 2007, vol. 2, pp. 362-369, in German with English abstract.
Hanna et al., "Canadian Diabetes Association Clinical Practice Guidelines Expert Committee Pharmacologic Management of Type 2 Diabetes," Canadian Journal of Diabetes, Dec. 2003, vol. 27 (Supp 2), pp. S37-S42.
Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.
Harris S.B., et al., "Clinical inertia in Patients with T2Dm Requiring Insulin in Family Practice," Canadian Family Physician, 2010, vol. 56 (12), pp. e418-e424.
Hartmann H., et al., "Biological Activity of Des-(B26-B30)-Insulinamide and Related Analogues in Rat Hepatocyte Cultures," Diabetologia, 1989, vol. 32 (7), pp. 416-420.
Heinrich G., et al., "Pre-Proglucagon Messenger Ribonucleic Acid: Nucleotide and Encoded Amino Acid Sequences of the Rat Pancreatic Complementary Deoxyribonucleic Acid," Endocrinology, 1984, vol. 115 (6), pp. 2176-2181.
Hellstrom M., et al., "T1388 GTP-010 as a Therapetuic tool in IBS Pain Relief: Prospective, Randomized, Palebo-Controlled Study of a GLP-1 Analog," Gastroenterology, Apr. 2008, vol. 134 (4), pp. A-544.
Higgins G.C., et al., "Oxidative Stress: Emerging Mitochondrial and Cellular themes and Variations in Neuronal Injury," Journal of Alzheimer's Disease, 2010, vol. 20, pp. S453-S473.
Himeno T., et al., "Beneficial Effects of Exendin-4 on Experimental Polyneuropathy in Diabetic Mice," Diabetes, 2011, vol. 60 (9), pp. 2397-2406.
Hinds K., et al., "Synthesis and Characterization of Poly(Ethylene Glycol)-Insulin Conjugates," Bioconjugate Chemistry, Mar.-Apr. 2000, vol. 11 (2), pp. 195-201.
Hinnen D.A., "Therapeutic Options for the Management of Postprandial Glucose in Patients With Type 2 Diabetes on Basal Insulin," Clinical Diabetes, 2015, vol. 33 (4), pp. 175-180.
HOE 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.
Holman R.R., et al., "10-Year Follow-Up of intensive Glucose Control in Type 2 Diabetes," The New England Journal of Medicine, 2008, vol. 359 (15), pp. 1577-1589.
Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.
Holscher C., et al., "New Roles for Insulin-Like Hormones in Neuronal Signalling and Protection: New Hopes for Novel Treatments of Alzheimer's Disease'?," Neurobiology of Aging, 2008, vol. 31 (9), pp. 1495-1502.
Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.
Holscher C., "Possible Causes of Alzheimer's Disease: Amyloid Fragments, Free Radical, and Calcium Homeostasis," Neurobiology of Disease, 1998, vol. 5 (3), pp. 129-141.
Holscher C., "The Role of GLP-1 in Neuronal Activity and Neurodegeneration," Vitamins and Hormones, 2010, vol. 84, pp. 331-354.
Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.
Holst J.J., "Glucagon-Like Peptide-1, A Gastrointestinal Hormone with a Pharmaceutical Potential," Current Medicinal Chemistry, 1999, vol. 6 (11), pp. 1005-1017.
Home P.D., et al., "Insulin Treatment: A Decade of Change," British Medical Bulletin, 1989, vol. 45 (1), pp. 92-110.
http://diabetes.emedtv.com/lantus/generic-lantus.html; one page, last accessed Dec. 23, 2015.
Humalog® prescribing information, Apr. 2012, pp. 1-6.
Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.
IDF Clinical Guidelines Task Force, Global Guideline for Type 2 Diabetes, Brussels: International Diabetes Federation, Aug. 2005, pp. 1-82.
IDF, International Diabetes Federation Guideline Development Group, "Guideline for management of postmeal glucose in diabetes," Diabetes Research Clinical Practice, 2012, pp. 1-13.
Inpharma, Product News. "AVE0010 set to deliver in type 2 diabetes mellitus," Database Adisnews, retrieved from STN, Jun. 2008, pp. 1-3.
"Insulin Aspart Injection." Formulated Preparations: Specific Monographs. British Pharmacopoeia 3. pp. 1-3 (2012).
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
International Search Report by the ISA for International Application No. PCT/EP2015/079285; dated Mar. 9, 2016, pp. 1-7.
Inzucchi S.E., et al., "Management of Hyperglycemia in Type 2 Diabetes: A Patient-Centered Approach," Diabetes Care, Jun. 2012, vol. 35, pp. 1364-1379.

(56) References Cited

OTHER PUBLICATIONS

Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
ISPAD, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, Jul. 1994, vol. 271 (1), pp. 58-65.
Jang J.H., et al., "Neuroprotective Effects of Triticum Aestivum L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-LB.pdf.
Johnson P.J., et al., "Diabetes, Insulin Resistance, and Metabolic Syndrome in Horses," Journal of Diabetes Science and Technology, May 2012, vol. 6 (3), pp. 534-540.
Jones K.L., et al., "Effect of Metformin in Pediatric Patients with Type 2 Diabetes: A Randomized Controlled Trial," Diabetes Care, Jan. 2002, vol. 25 (1), pp. 89-94.
Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm N.C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T- to R-Allosteric Transition in the Insulin Hexamer," Biochemistry, Oct. 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, Jun. 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kanazawa M., et al., "Criteria and Classification of Obesity in Japan and Asia-Oceania," Asia Pacific Journal of Clinical Nutrition, Dec. 2002, vol. 11 (Suppl 7), pp. S732-S737.
Kang S., et al., "Subcutaneous Insulin Absorption Explained by Insulin'S Physicochemical Properties Evidence from Absorption Studies of Soluble Human Insulin and Insulin Analogues in Humans," Diabetes Care, Nov. 1991, vol. 14 (11), pp. 942-948.
Kao C.H., et al., "The Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin A.J., et al., "Entry of Exedin-4 into Brain Is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kell T.M., et al., "Systematic Review: Glucose Control and Cardiovascular Disease in Type 2 Diabetes." Annals Internal Medicine, 2009, vol. 151 (6), pp. 394-403, Sep. 2009; Epub Jul. 20, 2009.
Kemmler W., et al., "Studies on the Conversion of ProInsulin to Insulin," The Journal of Biological Chemistry, 1971, vol. 246 (22), pp. 6786-6791.
Kendall D.M., et al., "Clinical Application of Incretin-Based Therapy: Therapeutic Potential, Patient Selection and Clinical Use." European Journal of Internal Medicine, Jul. 2009, vol. 20 (Suppl 2), pp. S329-S339.
Kendall D.M., et al., "Effects of Exenatide (Exendin-4) on Glycemic Control Over 30 Weeks in Patients with Type 2 Diabetes Treated with Metformin and a Sulfonylurea," Diabetes care, May 2005, vol. 28 (5), pp. 1083-1091.
Khaw K., et al., "Giycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.
Kielgast U., et al., "Treatment of Type 1 Diabetic Patients with Glucagon-Like Peptide-1 (GLP-1) and GLP-1R Agonists," Current Diabetes Reviews, Nov. 2009, vol. 5 (4), pp. 266-275.
Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.
Kim S.Y., et al., "Retinopathy in Monkeys with Spontaneous Type 2 Diabetes" Investigative Opth & Visual Science, Dec. 2004, vol. 45 (12), pp. 4543-4553.
Knee T.S., et al., "A Novel Use of U-500 Insulin for Continuous Subcutaneous Insulin infusion in Patients with Insulin Resistance: A Case Series," Endocrine Practice, May/Jun. 2003, vol. 9 (3), pp. 181-186.
Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.
Kohn W.D., et al., "Pi-Shifted Insulin Analogs with Extended in Vivo Time Action and Favorable Receptor Selectivity," Peptides, 2007, vol. 28 (4), pp. 935-948.
Kohner E.M., "Diabetic Retinopathy," British Medical Bulletin, 1989, vol. 45 (1), pp. 148-173.
Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.
Korczyn A.D., et al, "Emerging therapies in the Pharmacological Treatment of Parkinson's Disease," Drugs, 2002, vol. 62 (5), pp. 775-786.
Krishnamurthy G.T., et al., "Constancy and Variability of Gallbladder Ejection Fraction: Impact on Diagnosis and therapy," Journal of Nuclear Medicine, Nov. 2004, vol. 45 (11), pp. 1872-1877.
Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).
Langston J.W., et al., "Chronic Parkinsonism in Humans due to a Product of Meperedine-Analog Synthesis," Science, 1983, vol. 219 (4587), pp. 979-980.
Langui D., et al., "Subcellular Topography of Neuronal Aβ Peptide in APPxPS1 Transgenic Mice," The American Journal of Pathology, 2004, vol. 165 (5), pp. 1465-1477.

(56) References Cited

OTHER PUBLICATIONS

Lantus® Annex I—Summary of product characteristics. Date of first authorisation: Jun. 9, 2000, pp. 1-164.
Lantus® prescribing information, May 2012, pp. 1-6.
Lantus® Product Information—European Medicines Agency, first published Aug. 5, 2009, pp. 1-2.
Larsen B.D., et al., "Sequence-Assisted Peptide Synthesis (SAPS)," Journal of Peptide Research, 1998, vol. 52 (6), pp. 470-476.
Larsen P.J., et al., "Combination of the Insulin Sensitizer, Pioglitazone, and the Long-Acting Glp-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.
Laursen K., et al., "Enhanced Monitoring of Biopharmaceutical Product Purity Using Liquid Chromatography-Mass Spectrometry," Journal of Chromatography A, Jul. 2011; Epub May 2011, vol. 1218 (28), pp. 4340-4348.
Lee C.H., et al., "Ischemia-Induced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.
Leib R.D., et al., "Direct Quantitation of Peptide Mixtures without Standards Using Clusters formed by Electrospray Ionization Mass Spectrometry," Analytical Chemistry, May 2009, vol. 81 (10), pp. 3965-3972.
Lens J., "The Terminal Carboxyl Groups of Insulin," Biochimica et Biophysica Acta, 1949, vol. 3, pp. 367-370.
Levemir® prescribing information, Dec. 2011, pp. 1-6.
Levene P.A., et al., "Calculation of Isoelectric Point," The Journal of Biological Chemistry, 1923, vol. 55, pp. 801-813.
Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.
Levine R.L., et al., "Oxidation of Methionine in Proteins: Roles in Antioxidant Defense and Cellular Regulation," IUBMB life, Oct. 2000, vol. 50 (4-5), pp. 301-307.
Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.
Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.
Li L., et al., "Common Pathological Processes in Alzheimer Disease and Type 2 Diabetes: A Review," Brain Research Reviews, 2007, vol. 56, pp. 384-402.
Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.
Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.
Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.
Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61, (English Translation Included).
Liu & Ruus, Abstract "Pharmacokinetics and Safety of the GLP-1 Agonist AVE0010 in Patients with Renal Impairment," Diabetes 58 (Suppl. 1): Abstract 557-P For the 69th Scientific Session of the American Diabetes Association Jun. 5-9, 2009, New Orleans, Louisiana, pp. 1-2.

Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.
Insulinpraparat Wikipedia, http://de.wikipedia.org/wiki/Insulinpr%C3%A4parat, pp. 1-15 (Feb. 5, 2013).
Insuman® Comb25 prescribing information, Feb. 2011, pp. 1-4.
Insuman® Infusat prescribing information, Feb. 2011, pp. 1-4.
Lopez-Delgado M.I., et al., "Effects of Glucagon-Like Peptide 1 on the Kinetics of Glycogen Synthase a in Hepatocytes from Normal and Diabetic Rats," Endocrinology, 1998, vol. 139 (6), pp. 2811-2817.
Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.
Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.
Lougheed W.D., et al., "Physical Stability of Insulin Formulations," Diabetes, 1983, vol. 32 (5), pp. 424-432.
Lyxumia 10 micrograms solution for injection, Summary of Product Characteristics, updated Oct. 31, 2014, pp. 1-12.
Lyxumia® Annex I—Summary of product characteristics. Date of first authorisation: Feb. 1, 2013, pp. 1-92.
Lyxumia, Chemical Subgroup A10BX, Community Register of Medicinal Products for Human Use, Eurpean Commission Public Health, p. 1-2 (May 2, 2013).
Lyxumia® Product Information—European Medicines Agency, first published Mar. 14, 2013, pp. 1-2.
Madsbad S., "Impact of Postprandial Glucose Control on Diabetes-Related Complications: How is the Evidence Evolving?" Journal of Diabetes and Its Complications, 2016, vol. 30, pp. 374-385, Available online Oct. 9, 2015.
Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.
Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, May 2008, vol. 116 (5), pp. 282-288.
Margolis R.L., et al., "Diagnosis of Huntington Disease," Clinical Chemistry, 2003, vol. 49 (10), pp. 1726-1732.
Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.
Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.
Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.
Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.
Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.
Mattson M.P., "Calcium and Neurodegeneration," Aging Cell, 2007, vol. 6 (3), pp. 337-350.
McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.

(56) References Cited

OTHER PUBLICATIONS

McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.
Mecklenburg R.S., et al., "Complications of Insulin Pump therapy: The Effect of Insulin Preparation," Diabetes Care, 1985, vol. 8 (4), pp. 367-370.
Medline Plus, "Obesity" available at http://www.nlm.nih.gov/medlineplus/obesity.html, Retrieved Aug. 22, 2013, one page.
Meier J.J., "GLP-1 Receptor Agonists for individualized Treatment of Type 2 Diabetes Mellitus," Nature Reviews. Endocrinology, 2012, vol. 8 (12), pp. 728-742.
Merrifield B., "Solid Phase Synthesis," Science, 1986, vol. 232 (4748), pp. 341-347.
Mikhail N.E., "Is Liraglutide a Useful Addition to Diabetes therapy? ," Endocrine Practice, Nov.-Dec. 2010, vol. 16 (6), pp. 1028-1037.
Miyazaki Y., et al., "Improved Glycemic Control and Enhanced Insulin Sensitivity in Type 2 Diabetic Subjects Treated with Pioglitazone", Diabetes Care, Apr. 2001, vol. 24(4), pp. 710-719.
Monnier L., et al., "Postprandial and Basal Glucose in Type 2 Diabetes: Assessment and Respective Impacts" Diabetes Technology & Therapeutics, 2011, vol. 13 (Suppl 1 ), pp. S25-S32.
Monnier L., et al., "The Loss of Postprandial Glycemic Control Precedes Stepwise Deterioration of Fasting with Worsening Diabetes," Diabetes Care, 2007, vol. 30 (2), pp. 263-269.
Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.
Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, Aug. 2008, vol. 30 (8), pp. 1448-1460.
Muller G., et al., "Insulin Signaling in the Yeast *Saccharomyces cerevisiae*. 1. Stimulation of Glucose Metabolism and Snf 1 Kinase by Human Insulin," Biochemistry, Jun. 1998, vol. 37 (24), pp. 8683-8695.
Muzaffar M., et al., "The Mechanism of Enhanced Insulin Amyloid Fibril formation by Naciis Better Explained by a Conformational Change Model," PLoS One, 2011, vol. 6 (11), pp. 1-11, e27906.
Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.
Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.
Nathan D.M., et al., "Medical Management of Hyperglycemia in Type 2 Diabetes: A Consensus Algorithm for the Initiation and Adjustment of Therapy" Diabetes Care, Jan. 2009, vol. 32 (1), pp. 193-203.
Nathan M.D., et al., "Insulinotropic Action of Glucagon Like Peptide-1-(7-37) in Diabetic and Nondiabetic Subjects," Diabetes Care, 1992, vol. 15 (2), pp. 270-276.
Nauck M.A., et al., "Comparative Evaluation of Incretin-Based Antidiabetic Medications and Alternative therapies to be Added to Melformin in the Case of Monotherapy Failure," Journal of Diabetes Investigation, Feb.-Apr. 2010, vol. 1 (1-2), pp. 24-36.
Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.
Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.
Nauck M.A., et al., "Glucagon-Like Peptide 1 (GLP-1) as a New therapeutic Approach for Type 2-Diabetes," Experimental and Clinical Endocrinology, 1997, vol. 105 (4), pp. 187-195.

NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00688701 Clinical Trials.gov "GLP-1 Receptor Agonist Lixisenatide in Patients with Type 2 Diabetes for Glycemic Control and Safety Evaluation in Monotherapy (Getgoal-Mono)" accessed Jul. 27, 2014; pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00713830, Clinical Trials.gov "GLP-1 Agonist in Patients with Type 2 Diabetes for Glycemic Control and Safety Evaluation, on Top of Sulfonylurea", 2016, pp. 1-3, accessed Mar. 16, 2016, (Updated Jul. 13, 2008).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
NCT00866658 ClinicaiTrials.gov, "GLP-1 Agonist AVE0010 in Patients with Type 2 Diabetes for Glycemic Control Safety Evaluation, on Top of Basil Insulin+/- Sulfonylurea," 2016, pp. 1-3, accessed Mar. 16, (Updated Jan. 010).
NCT00975286, Clinical Trials.gov, "24-week Treatment with Lixisenatide in Type 2 Diabetes Insufficiently Controlled With Melformin and Insulin Glargine", Aug. 8, 2011, pp. 1-4.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01169779, Clinical Trials.gov, "Efficacy and Safety of Lixisenatide in Patients with Type 2 Diabetes Mellitus Insufficiently Controlled by Metformin," 2016, pp. 1-3, accessed Mar. 16, 2016, (updated Mar. 28, 2011).
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on 6 Feb. 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.
NHSC—National Horizon Scanning Center, "AVE0010 (ZP10) for type 2 diabetes mellitus" University of Birmingham, England; pp. 1-6 (Dec. 2008).

(56) References Cited

OTHER PUBLICATIONS

Nice, National Institute for Health and Care Excellence, "Evidence Summary: New Medicine, ESNM26: Type 2 Diabetes: lixisenatide; Key Points from the Evidence," Sep. 24, 2013, pp. 1-26.
Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
NIH, National Institute of Diabetes and Digestive and Kidney Disease, "Hypoglycimia," Mar. 16, 2016, pp. 1-8.
Nilsson A., et al., "Effects of GI vs Content of Cereal Fibre of the Evening Meal on Glucose Tolerance at a Subsequent Standardized Breakfast," European Journal of Clinical Nutrition, Jun. 2008, vol. 62 (6), pp. 712-720 (Epub May 23, 2007).
Noble S.L., et al., "Insulin Lispro: A Fast-Acting Insulin Analog," American Family Physician, 1998, vol. 57 (2), pp. 279-286.
Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10, 2011, pp. 1-12.
Non-Final Office Action from U.S. Appl. No. 12/617,805; dated Sep. 15, 2015, pp. 1-12.
Non-Final Office Action issued in U.S. Appl. No. 13/123,835; dated Dec. 22, 2014, pp. 1-13.
Non-Final Office Action issued in U.S. Appl. No. 13/123,835; dated Jul. 19, 2012, pp. 1-14.
Non-Final Office Action issued in U.S. Appl. No. 13/123,835; dated May 28, 2015, pp. 1-11.
Non-Final Office Action issued in U.S. Appl. No. 13/602,913; dated Dec. 2, 2014, pp. 1-12.
Non-Final Office Action issued in U.S. Appl. No. 13/602,913; dated Jan. 13, 2014, pp. 1-53.
Non-Final Office Action issued in U.S. Appl. No. 13/602,913; dated May 17, 2013, pp. 1-7.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,563; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/617,811; dated Apr. 27, 2011, pp. 1-10.
Non-Final Rejection issued in U.S. Appl. No. 12/617,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118; dated Mar. 19, 2012, pp. 1-19.
Non-Final Rejection issued in U.S. Appl. No. 13/310,118, dated Mar. 29, 2013, pp. 1-21.
Non-Final Rejection issued in U.S. Appl. No. 13/310,118, dated Mar. 25, 2015, pp. 1-15.
Non-Final Rejection issued in U.S. Appl. No. 13/363,956; dated Apr. 10, 2013, pp. 1-15.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final Rejection issued in U.S. Appl. No. 13/363,956; dated Nov. 20, 2013, pp. 1-10.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,442; dated Mar. 31, 2016, pp. 1-29.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.
Non-Final Rejection issued in U.S. Appl. No. 13/467,707; dated Jul. 15, 2013, pp. 1-20.
Non-Final Rejection issued in U.S. Appl. No. 13/467,707; dated Jul. 25, 2014, pp. 1-22.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.
Non-Final Rejection issued in U.S. Appl. No. 13/469,633; dated Aug. 19, 2013, pp. 1-25.
Non-Final Rejection issued in U.S. Appl. No. 13/469,633; dated Aug. 22, 2014, pp. 1-23.
Non-Final Rejection issued in U.S. Appl. No. 13/469,633; dated Mar. 27, 2013, pp. 1-39.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.
Non-Final Rejection issued in U.S. Appl. No. 13/509,507; dated Dec. 8, 2015, pp. 1-14.
Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/661,476, dated Dec. 4, 2013, pp. 1-11.
Non-Final Rejection issued in U.S. Appl. No. 13/661,476, dated Mar. 6, 2014, pp. 1-28.
Non-Final Rejection issued in U.S. Appl. No. 13/661,476, dated Sep. 16, 2013, pp. 1-19.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.

(56) References Cited

OTHER PUBLICATIONS

Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 13/819,114; dated Dec. 2, 2015, pp. 1-14.
Non-Final Rejection issued in U.S. Appl. No. 13/819,114; dated Jul. 31, 2014, pp. 1-9.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.
Non-Final Rejection issued in U.S. Appl. No. 13/467,757; dated Apr. 17, 2013, pp. 1-9.
Non-Final Rejection issued in U.S. Appl. No. 13/468,422; dated Jun. 4, 2014, pp. 1-24.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Non-Final Rejection issued in U.S. Appl. No. 13/382,772; dated Apr. 10, 2013, pp. 1-48.
Non-Final Rejection dated Dec. 17, 2015 for U.S. Appl. No. 12/820,722, filed Jun. 22, 2010, pp. 1-5.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Non-Final-Rejection issued in U.S. Appl. No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Olansky L., "Do Incretin-Based Therapies Cause Acute Pancreatitis?," Journal of Diabetes Science and Technology, Jan. 2010, vol. 4 (1), pp. 228-229.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study A Prospective 4-Year-Follow-Up Study on the Quality of Treatment for Type 2 Diabetes in Daily Practice," Deutsche Medizinische Wochenschrift, 2009, vol. 134 (7), pp. 291-297, English Absract submitted.
Park C.W., et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 2007, vol. 18 (4), pp. 1227-1238, Apr. 2007; Epub Mar. 14, 2007.
Park C.W., et al., "PPARalpha Agonist Fenofibrate Improves Diabetic Nephropathy in Db/Db Mice," Kidney International, Published Online Mar. 1, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.

Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, Aug. 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, Oct. 1998, vol. 15(10), pp. 1637-1639.
Pinget M., et al., "Efficacy and safety of lixisenatide once daily versus placebo in type 2 diabetes insufficiently controlled on pioglitazone (GetGoal-P)," Diabetes,61(Supp 1):A258, Poster 1010-P (Jun. 2012).
Pinhas-Hamiel O., et al., "Clinical Presentation and Treatment of Type 2 Diabetes in Children," Pediatric Diabetes, Dec. 2007, vol. 8 (Suppl. 9), pp. 16-27.
Pi-Sunyer F.X., "The Effects of Pharmacologic Agents for Type 2 Diabetes Mellitus on Body Weight," Postgraduate Medicine, Jul. 2008, vol. 120 (2), pp. 5-17.
Pohl M., et al., "Molecular Cloning of the Heloderman and Exendin-4 cDNAs in the Lizard," The Journal of Biological Chemistry, 1998, vol. 273 (16), pp. 9778-9784.
Porter D.W., et al., "Four Weeks Administration of Liraglutide Improves Memory and Learning as Well as Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-S66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, Sep. 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109, (Winter 2011).
Raccah D., et al., "When Basal Insulin therapy in Type 2 Diabetes Mellitus is not Enough—What Next?," Diabetes/Metabolism Research and Reviews, Published Online Feb. 21, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, published online, Jan. 11, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.

(56) References Cited

OTHER PUBLICATIONS

Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.

Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, Sep. 2010, vol. 27 (9), pp. 1024-1032.

Ratner R.E., et al., "Post-Meal Pharmacodynamics Profile of Ave0010, A Once-Daily GLP-1 Receptor Agonist, in Patiens with Type 2 Diabetes Inadequately Controlled on Metformin," Diabetologia, Sep. 2009, vol. 52 (Suppl 1), pp. S60. Abstract 131.

Ratner R.E., et al., "Abstract # 433-P, A Dose-Finding Study of the New GLP-1 Agonist AVE0010 in Type 2 Diabetes Insufficiently Controlled with Metformin,"Jun. 6-10, 2008, vol. 57 (Suppl 1), p. A129.

Raufman J.P., "Bioactive Peptides from Lizard Venoms," Regulatory peptides, 1996, vol. 61 (1), pp. 1-18.

"Remington: The Science and Practice of Pharmacy", Twentieth Edition, Lippincott Williams & Wilkins, USA, 2000, pp. 1-5.

Request for "Type C" Meeting letter sent by Michael Lutz addressed to Mary Parks, dated Apr. 21, 2006, pp. 1-10.

Richter, von Margret, "Oldtimer as Newcomer" Pharmazie, pp. 1-9; http://www.pharmazeutische-zeitung.de/pza/2002-12/pharm1.htm (Feb. 2002).

Riddle M., et al., "Contributions of Basal and Postprandial Hyperglycemia over a Wide Range of A 1 C Levels before and alter Treatment Intensification in Type 2 Diabetes," Diabetes Care, Published Online Oct. 25, 2011, vol. 34, pp. 2508-2514.

Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, Sep. 2013, vol. 36 (9), pp. 2489-2496.

Riddle M.C., et al., "Adding once-Daily Lixisenatide for Type 2 Diabetes inadequately Controlled with Newly initiated and Continuously Titrated Basal Insulin Glargine," Diabetes Care, Sep. 2013, pp. 2497-2503.

Ritzel U., et al., "A Synthetic Glucagon-Like Peptide-1 Analog with Improved Plasma Stability," The Journal of Endocrinology, 1998, vol. 159 (1), pp. 93-102.

Rohrmann C.A., "Differential Diagnosis of Pancreatic and Biliary Duct Diseases," Diseases of the Abdomen and Pelvis Syllabus, 1999, pp. 170-174.

Rosenstock J., et al., "Dose Range Effects of the New Once Daily GLP-1 Receptor Agonist AVE0010 Added to Metformin in Type 2 Diabetes," Diabetologia, Sep. 2008, vol. 51 (Suppl 1), pp. S66. Abstract 145.

Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.

Rosenstock J., et al., "Post-Meal Effects of AVE0010, A Once-Daily GLP-1 Receptor Agonist, in Type 2 Diabetes Inadequately Controlled on Metformin," Diabetes, Jun. 1, 2009, vol. 58 (Suppl 1), pp. A151-A152. Abstract 564P.

Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.

Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.

Sanger F., et al., "The Amide Groups of Insulin," The Biochemical Journal, 1955, vol. 59 (3), pp. 509-518.

Sanofi and Zealand Pharma Press Release (Evaluate), "Additional Positive Results from Global Phase III Program With Lixisenatide for Type 2 Diabetes", (Apr. 12, 2011) pp. 1-3.

Sanofi's Lantus Draft Prescribing Information/Package Insert: "NDA 21-081 DRAFT package insert" (Sponsor revision #5) Date of submission: Apr. 20, 2000; see http://www.drugbank.ca/system/fds_labels/DB00047.pdf1265922812; pp. 1-14.

Sanofi Press Release entitled "FDA Accepts Sanofi's New Drug Application for Basal Insulin Toujeo®," dated Jul. 8, 2014, pp. 1-2.

Sanofi Press Release; "Lyxumia (lixisenatide) in Combination with Basal insulin plus Oral Anti-Diabetics Significantly Reduced HbAl c and Post-Prandial Glucose"; Paris, France (Jun. 9, 2012) pp. 1-6.

Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.

Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.

Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.

Sanofi Press Release "Positive Results for Investigational Compound Lyxumia (Lixisenatide) Presented at American Diabetes Association's 71st Annual Scientific Sessions," (Jun. 24, 2011), pp. 1-5.

Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.

Sanofi-Aventis Press Release, "A Promising R&D Portfolio, Well Positioned to Deliver Future Growth," Sep. 17, 2007, pp. 1-11.

Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.

Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.

Sanofi-aventis Press Release (Peron and Schaeffer), "Sanofi-aventis Announces Positive Top-line Lixisentatide Phase III Results" Paris, France (Feb. 2, 2011) pp. 1-2.

Sanofi Press Release entitled "Sanofi Receives FDA Approval of Once-Daily Basal Insulin Toujeo®," dated Feb. 26, 2015, pp. 1-4.

Schapira A.H., "Causes of Neuronal Death in Parkinson's Disease," Advances in Neurology, 2001, vol. 86, pp. 155-162.

Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.

Schellenberger V., et al., "Protease-Catalyzed Kinetically Controlled Peptide Synthesis," Angewante Chemie, 1991, vol. 30 (11), pp. 1437-1449.

Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.

Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.

Schubert-Zsilavecz M., et al., "Better Blood Sugar Control in Diabetics. Insulin Glargin—A Long Acting Insulin Analogue," Pharmazie in Unserer Zeit, 2001, vol. 30 (2), pp. 125-130, With English translation.

Schwartz G.J., et al., "New Equations to Estimate GFR in Children with CKD," Journal of the American Society of Nephrology, Mar. 2009, vol. 20 (3), pp. 629-637 (Epub Jan. 21, 2009).

Schwartz G.P., et al., "A Superactive Insulin: [B10-Aspartic Acid]Insulin(Human)," Proceedings of the National Academy of Sciences of the United States of America, Sep. 1987, vol. 84 (18), pp. 6408-6411.

(56) References Cited

OTHER PUBLICATIONS

Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Search Report of the Intellectual Property Office of Singapore for Patent Application No. 10201500871T, dated Nov. 2, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, Oct. 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (In Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: a Retrospective Observational Study," Cardiovascular Diabetology, Published Jan. 19, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, Nov. 1991, vol. 88 (21), pp. 9377-9381.
Smolka M.B., et al., "Optimization of the Isotope-Coded Affinity Tag-Labeling Procedure for Quantitative Proteome Analysis," Analytical Biochemistry, Oct. 2001, vol. 297 (1), pp. 25-31, Abstract only submitted.
Spertus J.A., et al., "Development and Evaluation of the Seattle Anginal Questionnaire: a New Functional Status Measure for Coronary Artery Disease." Journal American College of Cardiology, Feb. 1995, vol. 25 (2), pp. 333-341.
Spertus J.A., et al., "Health Status Predicts Long-Term Outcome in Outpatients with Coronary Disease." Circulation, Jul. 2002, vol. 106 (1 ), pp. 43-49.
Sporn M.B., et al., "Chemoprevention of Cancer," Carcinogenesis, 2000, vol. 21 (3), pp. 535-530.
Srinivasan K., et al., "Animal Models in Type 2 Diabetes Research: An Overview." Indian Journal Medical Research, Mar. 2007, vol. 125, pp. 451-472.
St. John Providence Health Center, "Preventing Obesity" http://www.stjohnprovidence.org/HealthInfolib/swarticle.aspx?type=85&id= P07863, Retrieved Aug. 22, 2013, pp. 1-2.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Summary of Product Characteristics Lyxumia 10 micrograms solution for injection, pp. 1-93, published Mar. 14, 2013.
Sundby F., "Separation and Characterization of Acid-induced Insulin Transformation Products by Paper Electrophoresis in 7 M Urea," The Journal of Biological Chemistry, Nov. 1962, vol. 237 (11), pp. 3406-3411.
Tanner C.M., et al., "Rotenone, Paraquat, and Parkinson's Disease," Environmental Health Perspectives, 2011, vol. 119 (6), pp. 866-872.
Tanner J.M., et al., "Standards from Birth to Maturity for Height, Weight, Height Velocity, and Weight Velocity: British Children, Part II," Archives of Disease in Childhood, 1966, vol. 41 (220), pp. 613-635.

Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral Ischemia," Journal of Cerebral Blood Flow and Metabolism, 2011, vol. 31 ( 8), pp. 1696-1705.
Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
Tews D., et al., "Enhanced Protection against Cytokine- and Fatty Acid-Induced Apoptosis in Lns-1 Beta-Cells by Combined Treatment with Insulin Glargine and the Novel GLP-1 Receptor Agonist Ave0010," Diabetes, 2007, vol. 56 (Suppl 1), pp. A72-A73.
Tews D., et al., "Enhanced Protection Against Cytokine- and Fatty Acid-induced Apoptosis in Pancreatic Beta Cells by Combined Treatment with Glucagon-Like Peptide-1 Receptor Agonists and Insulin Analogues," Hormone and Metabolic Research, Mar. 2008, vol. 40 (3), pp. 172-180.
The Advance Collaborative Group, "Intensive Blood Glucose Control and Vascular Outcomes in Patients with Type 2 Diabetes." New England Journal of Medicine, Jun. 2008, vol. 358 (24), pp. 2560-2572.
The Diabetes Control and Complications Trial Research Group, "The Effect of intensive Treatment of Diabetes on the Development and Progression of Long-Term Complications in Insulin-Dependent Diabetes Mellitus," The New England Journal of Medicine, Sep. 1993, vol. 329, pp. 977-986.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.
Thurow H., et al., "Stabilisation of Dissolved Proteins against Denaturation at Hydrophobic Interfaces," Diabetologia, Aug. 1984, vol. 27 (2), pp. 212-218.
Toth M.L., et al., "Neurite Sprouting and Synapse Deterioration in the Aging Caenorhabditis Elegans Nervous System," The Journal of Neuroscience, 2012, vol. 32 (26), pp. 8778-8790.
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," May 2010, vol. 233; No. 9: 750-754, pp. 1-4.
Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.
Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.
UK Prospective Diabetes Study (UKPDS) Group, "Effect of intensive Blood-Glucose Control with Metformin on Complications in Overweight Patients with Type 2 Diabetes (UKPDS 34)," Lancet, Sep. 1998, vol. 352 (9131), pp. 854-865.
UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," The Lancet, Sep. 12, 1998, vol. 352, pp. 837-853.

(56) References Cited

OTHER PUBLICATIONS

UK Prospective Diabetes Study (UKPDS) Group, "Tight Blood Pressure Control and Risk of Macrovascular and Microvascular Complications in Type 2 Diabetes (UKPDS 38)," BMJ, Sep. 1998, vol. 317, pp. 703-713.
"Suspension" Stedman's Medical Dictionary, 20th Edition, p. 1450 (Williams & Wilkins Co., Baltimore 1961).
"Suspension" Taber's Cyclopedic Medical Dictionary, 19th Edition, p. 2097 (F.A. Davis Co., Philadelphia 2001).
Uttenthal L.O., et al., "Molecular forms of Glucagon-Like Peptide-1 in Human Pancreas and Glucagonomas," The Journal of Clinical Endocrinology & Metabolism, 1985, vol. 61 (3), pp. 472-479.
Valle J., et al., "Cisplatin Plus Gemcitabine Versus Gemcitabine for Biliary Tract Cancer," The New England Journal of Medicine, Apr. 2010, vol. 362 (14), pp. 1273-1281.
Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.
Victoza® Annex I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, Nov. 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wan Z., et al., "Enhancing the Activity of Insulin at the Receptor Interface: Crystal Structure and Photo-Cross-Linking of A8 Analogues," Biochemistry, 2004, vol. 43 (51), pp. 16119-16133.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, Jan. 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2, (2 Pages Including Abstract and Poster).
Werner U., et al., "Pharmacological Profile of Lixisenatide: A New GLP-1 Receptor Agonist for the Treatment of Type 2 Diabetes," Regulatory Peptides, Epub Jun. 2, 2010, vol. 164 (2-3), pp. 58-64.
Weyer C., et al., "Long-Term Changes in Insulin Action and Insulin Secretion Associated with Gain, Loss, Regain and Maintenance of Body Weight," Diabetologia, Jan. 2000, vol. 43 (1), pp. 36-46.
White I.R., et al., "Randomized Clinical Trials with Added Rescue Medication: Some Approaches to their Analysis and interpretation," Statistics in medicine, 2001, vol. 20 (20), pp. 2995-3008.
Whittingham J.L., et al., "Insulin at pH 2: Structural Analysis of the Conditions Promoting Insulin Fibre formation," Journal of Molecular Biology, 2002, vol. 318 (2), pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines,http://www.who.int/medicines/areas/rational_use/en/downloaded Dec. 18, 2014 10:02:48 AM (2012).
Widjaja A., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.
Wiernsperger N.F., et al., "The Antihyperglycaemic Effect of Metformin: Therapeutic and Cellular Mechanisms," Drugs, Sep. 1999, vol. 58 (Suppl 1), pp. 31-39.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Lixisenatide" Retrieved from the Internet: https://en.wikipedia.org/wiki/Lixisenatide one page, retrieved Apr. 11, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.
Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wivioti S.D., et al., "Greater Clinical Benefit of More Intensive Oral Anti platelet Therapy With Prasugrel in Patients With Diabetes Mellitus in the Trial to Assess Improvement in Therapeutic Outcomes by Optimizing Platelet Inhibition With Prasugrei-Thrombolysis in Myocardial Infarction 38," Circulation, 2008, vol. 118 (16), pp. 1626-1636, Oct. 2008; Epub Aug. 31, 2008.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
World Health Organisation Report on "Definition and Diagnosis of Diabetes Mellitus and Intermediate Hyperglycemia: Report of a WHO/IDF Consultation," 2006, pp. 1-50.
World Health Organization, "Definition, Diagnosis and Classification of Diabetes Mellitus and its Complications, Part 1: Diagnosis and Classification of Diabetes Mellitus," WHO/NCD/NCS/99.2, Geneva, 1999, pp. 1-66.
Written Opinion of the ISA for International Application No. PCT/EP2011/058079, dated Mar. 22, 2012, pp. 1-8.
Xie H., et al., "Characterization of Protein Impurities and Site-Specific Modifications Using Peptide Mapping with Liquid Chromatography and Data Independent Acquisition Mass Spectrometry," Analytical Chemistry, Jul. 2009, vol. 81 (14), pp. 5699-5708.
Yki-Jarvinen H., et al., "Insulin Glargine or Nph Combined with Metformin in Type 2 Diabetes: The Lanmet Study," Diabetologia, Mar. 2006, vol. 49 (3), pp. 442-451.
Yki-Jarvinen H., "Thiazolidinediones," The New England Journal of Medicine, Sep. 2004, vol. 351 (11), pp. 1106-1118.
Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.

(56) References Cited

OTHER PUBLICATIONS

Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278, Abstract only.
Yusuf S., et al., "Effects of Clopidogrel in Addition to Aspirin in Patients with Acute Coronary Syndromes without ST-Segment Elevation." New England Journal Medical, Aug. 2001, vol. 345 (7), pp. 494-502.
Zealand Pharma Company Announcement "Zealand Pharma, Additional positive results from Global Phase III program with −3-lixisenatide for type 2 diabetes", Apr. 12, 2011, pp. 1-3, URL: http://files.shareholder.com/downloads/ABEA-58QR0J/0x0x458202/3ccd84a6-5f99-451a-ada0-0a8282da3dad/ZEAL_News_2011_4_12Company_Releases.pdf.
Zealand Pharma Press Release entitled "Sanofi-Aventis finalize phase IIa clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, Feb. 2010, vol. 51 (2), pp. 277-281.
Zimmet P., et al., "Clinical Efficacy of Metformin Against Insulin Resistance Parameters: Sinking the Iceberg," Review Article, Drugs, Sep. 1999, vol. 58 (Suppl 1), pp. 21-28.
Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+TZD)," Diabetes Care, Jul. 2009, vol. 32 (7), pp. 1224-1230.
Zinman B., "The Physiologic Replacement of Insulin an Elusive Goal," The New England Journal of Medicine, Aug. 1989, vol. 321 (6), pp. 363-370.
Zoungas et al., "Combined Effects of Routine Blood Pressure Lowering and Intensive Glucose Control on Macrovascular and Microvascular Outcomes in Patients With Type 2 Diabetes. New results from the Advance trial." Diabetes Care, 2009, vol. 32(11 ), pp. 2068-2074, Nov. 2009; Epub Aug. 3, 2009.
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Home et al., "Management of type 2 diabetes: updated NICE guidance" BMJ 336: 1306-1308 (Jun. 2008).
Ismail-Beigi et al., "Individulaizing Glycemic Targets in Type 2 Diabetes Mellitus: Implications of Recent Clinical Trials" Annals of Internal Medicine 154(8):554-559 (Apr. 2011).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Lantus® Drug Description, downloaded Nov. 12, 2015, one page.
Lee et al., "Goals of Glycemic Control in Frail Older Patients with Diabetes" JAMA 305(13):1350-51 (Apr. 2011).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in postprandial glycaemic control compared to sitagliptin," Diabetologia 51(Supplement 1) p. S348, Abstract 872, one p. (2008).
Mainous et al., "Impact of the population at risk of diabetes on projections of diabetes burden in the United States: an epidemic on the way." Diabetologia 50(5):934-40 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Miller et al., "Type 2 diabetes in the child and adolescent", In: Lifshitz F (ed) Pediatric Endocrinology: 5th edition, vol. 1, New York, Marcel Dekker, pp. 169-188 (2007).
Mokdad et al., "The association of body mass index with the risk of type 2 diabetes: a case-control study nested in an electronic health records system in the United States." JAMA, 289(1):76-79 (Jan. 2003).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008.
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
NCT00866658 ClinicalTrials.gov, "GLP-1 agonist AVE0010 in patients with type 2 diabetes for glycemic control and safety evaluation, on top of basil insulin +/− sulfonylurea" p. 1-3, accessed Mar. 16, 2016 (updated Aug. 3, 2010).
Nice, National Institute for Health and Care Excellence, "Type 2 diabetes in adults: management" pp. 1-45 (Dec. 2, 2015).
Nihonn-Iyakuhin-shu Iryoyaku "Pioglitazone hydrochloride, Insulin sensitizing hypoglycemic agent" 2009 Edition, Jiho Inc. p. 1901 (2009).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Osterbye et al., "Sulfatide promotes the folding of proinsulin, preserves insulin crystals, and mediates its monomerization." Glycobiology 11(6):473-79 (Jun. 2001).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).

(56) References Cited

OTHER PUBLICATIONS

Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).
Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).
Raman & Heptulla, "New potential adjuncts to treatment of children with type 1 diabetes mellitus" Pediatric Research, 65(4):370-74 (Apr. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; 2000.
Riddle et al., "The treat-to-target trial: randomized addition of glargine or human NPH insulin to oral therapy of type 2 diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Sacks et al., "Guidelines and Recommendations for Laboratory Analysis in the Diagnosis and Management of Diabetes Mellitus." Clinical Chemistry 48(3):436-72 (Mar. 2002).
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Sanofi-aventis Press Release, "Once Daily Lixisenatide in Combination with Basal Insulin Demonstrates Significant Improvement in Glucose Control" Paris, France (Sep. 30, 2010) pp. 1-3.
Sanofi Press Release entitled "Sanofi Announces Top-Line Results for Cardiovascular Outcomes Study of Lyxumia® (lixisenatider).", dated Mar. 19, 2015, Paris, France, pp. 1-2.
Shehadeh et al., "Can GLP-1 preparations be used in children and adolescents with diabetes mellitus?" Pediatric Endocrinology Reviews, 11(3):324-27 (Mar. 2014).
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Sloop et al., "Glucagon as a target for the treatment of Type 2 diabetes." Expert Opin Ther Targets. 9(3):593-600 (Jun. 2005).
Ahmad & Swann, and Bloomgren "Exenatide and rare adverse events." N Engl J Med 358(18):1969-72 (May 2008).
Ahren, "GLP-1 for type 2 diabetes", Experimental Cell Research, 317(9):1239-45 (Jan. 2011).
Albert-Ludwigs University Freiburg, Institute fur Medizinische Biometrie und Statistik "Non-Inferiority Trails" dated Mar. 29, 2017, one page.

American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9, 2008, two pages.
American Diabetes Association, "Standards of Medical Care in Diabetes." Diabetes Care 28(Supplement 1): S4-S36 (Jan. 2005).
American Diabetes Association, "Standards of Medical Care in Diabetes—2008." Diabetes Care 31(Supplement 1): S12-S54.
American Diabetes Association, "Standards of Medical Care in Diabetes—2017" Diabetes Care 40(Supplement 1):S1-S142 (Jan. 2017).
Bastyr et al., "Therapy focused on lowering postprandial glucose, not fasting glucose, may be superior for lowering HbA1c. IOEZ Study Group." Diabetes Care 23(9):1236-41 (Sep. 2000).
Bell et al., "Sequence of the human insulin gene." 284(5751):26-32 (Mar. 1980).
Bennett, "Impact of the new WHO classification and diagnostic criteria." Diabetes Obes Metab 1(Supplement 2):S1-S6 (1999).
Bergenstal et al., "Type 2 Diabetes: Assessing the Relative Risks and Benefits of Glucose-lowering Medications" The American Journal of Medicine 123(4):e9-e18 (Apr. 2010).
Buse et al., "Effects of exenatide (Exendin-4) on glycemic control over 30 weeks in sulfonylurea-treated patients with type 2 diabetes." Diabetes Care 27(11):2628-35 (Nov. 2004).
Byetta® Labeling Revision, pp. 1-24 (Jan. 11, 2008).
Byetta® European Public Assessment Report (EPAR), pp. 1-36 (Feb. 16, 2012).
Byetta® Prescribing Information, pp. 1-34 (Revised Oct. 2009).
Byetta® Summary of Product Characteristics, updated Jul. 22, 2016, last accessed Jul. 31, 2017, pp. 1-13.
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
D'Alessio et al., "The role of dysregulated glucagon secretion in type 2 diabetes" Diabetes, Obesity and Metabolism, 13(Supppl. 1):126-132 (Oct. 2011).
Definition of "prevent" Dictionary.com; last accessed Sep. 29, 2016, pp. 1-6.
Definition of "induce" Dictionary.com; last accessed Sep. 29, 2016, pp. 1-6.
Definition of "reduce" Dictionary.com; last accessed Aug. 13, 2017, pp. 1-4.
Degn et al., "Effect of Intravenous Infusion of Exenatide (Synthetic Exendin-4) on Glucose-Dependent Insulin Secretion and Counterregulation During Hypoglycemia." Diabetes 53(9):2397-2403 (Sep. 2004).
De la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
Denker et al., "Exenatide (Exendin-4)-Induced Pancreatitis: A case report" Diabetes Care 29(2):471 (Feb. 2006).
De Venciana et al., "Postprandial versus preprandial blood glucose monitoring in women with gestational diabetes mellitus requiring insulin therapy." N Engl J Med 333(19):1237-41 (Nov. 1995).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).

(56) References Cited

OTHER PUBLICATIONS

Donahue et al., "Postchallenge glucose concentration and coronary heart disease in men of Japanese ancestry. Honolulu Heart Program." Diabetes 36(6):689-92 (Jun. 1987).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
Eckert et al., "Assessing the progression of Parkinson's disease: A metabolic network approach," Lancet Neurol. 6(10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16 (9):716-730 (1999).
Faichney, "Metformin in Type 1 diabetes: Is This a Good or Bad Idea?" Diabetes Care 26(5):1655 (May 2003).
Forlenza et al., "Diagnosis and biomarkers of predementia in Alzheimer's disease," BMC Medicine 8:89 pp. 1-14 (Dec. 2010).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
GenBank: AAP20099.1 "Interferon Alpha 2B [*Homo sapiens*]" dated Apr. 30, 2003; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAA52578.1 "GM-CSF [*Homo sapiens*]" dated Nov. 8, 1994; accessed Jan. 18, 2017, one page.
Gerich, "Insulin glargine: long-acting basal insulin analog for improved metabolic control." Curr Med Res Opin. 20(1):31-37 (Jan. 2004).
Giacometti et al., "In vitro activity of the histatin derivative P-113 against multidrug-resistant pathogens responsible for pneumonia in immunocompromised patients." 49(3):1249-52 (Mar. 2005).
Glucophage XR, Product Information, Bristol-Meyers Squibb Company (Jan. 2009).
Godoy-Matos, "The role of glucagon on type 2 diabetes at a glance," Diabetology & Metabolic Syndrome 6:91, pp. 1-5 (Aug. 2014).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Gromada et al., "Alpha-Cells of the Endocrine Pancreas: 35 Years of Research but the Enigma Remains" Endocrine Reviews 28(1):84-116 (Jan. 2007).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Harkavyi & Whitton, "Glucagon-like peptide 1 receptor stimulation as a means of neuroprotection" British Journal of Pharmacology 159(3):495-501 (2010; Epub Jan. 29, 2010).
Heine & Dekker, "Beyond postprandial hyperglycemia: metabolic factors associated with cardiovascular disease." Diabetologia 45(4):461-75 (Apr. 2002).
U.S. Appl. No. 15/340,969, filed Nov. 1, 2016, Werner et al.
U.S. Appl. No. 15/595,929, filed May 15, 2017, Brunner-Schwarz et al.
U.S. Appl. No. 15/275,867, filed Sep. 26, 2016, Silvestre et al.
U.S. Appl. No. 15/237,285, filed Aug. 15, 2016, Boka et al.
U.S. Appl. No. 15/144,270, filed May 2, 2016, Silvestre et al.
U.S. Appl. No. 15/197,378, filed Jun. 29, 2016, Niemöller.
U.S. Appl. No. 15/657,683, filed Jul. 24, 2017, Souhami et al.
U.S. Appl. No. 15/646,760, filed Jul. 11, 2017, Roy et al.
U.S. Appl. No. 15/146,255, filed May 4, 2016, Hess et al.
U.S. Appl. No. 15/411,557, filed Jan. 20, 2017, Boka et al.

Aguilar, "Heart failure and diabetes: Time to pay attention" American Heart Journal, 162(5):795-97 (Nov. 2011).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Game "Novel hypoglycaemic agents: Considerations in patients with chronic kidney disease" Nephron Clin Pract. 126(1):14-18 (Jan. 11, 2014).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Hasslacher et al., "Diabetic kidney disease" Exp and Clin Endocrinol Diabetes 122(7):391-94 (Jul. 2014).
Hubschle et al., "Anti-atherosclerotic activity of lixisenatide in ApoE knockout mice" Abstract 809, Diabetologia, 55 (Supplement 1):S334 (Oct. 2012).
Katz et al., "The clinical burden of type 2 diabetes in patients with acute coronary syndromes: Prognosis and implications for short- and long-term management" Diabetes and Vascular Disease Research, 11(6):395-409 (Nov. 2014).
Petersen & Christensen et al., "Clinical potential of lixisenatide once daily treatment for type 2 diabetes mellitus" Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Wohlfart et al., "Cardioprotective effects of lixisenatide in rat myocardial ischemia-reperfusion injury studies" Journal of Translational Medicine, 11(1):84, 12 pages (Mar. 2013).
Partial International Search Report by the ISA for International Application No. PCT/EP2016/055954; dated Jun. 21, 2016, pp. 1-6.
International Search Report by the ISA for International Application No. PCT/EP2016/055954; dated Sep. 9, 2016, pp. 1-12.
Spasov & Chepurnova, "Scientific Approaches to Combination Therapy for Type 2 Diabetes Mellitus," Bulletin of Volgograd State Medical University,1(37):8-10 (2011). See English Abstract.
Stumvoll et al., "Type 2 diabetes: Principles of pathogenesis and therapy." Lancet 365(9467):1333-46 (Apr. 2005).
Sutter Medical Foundation, "Type 2 Diabetes Adult Outpatient Insulin Guidelines" Feb. 2011, pp. 1-6.
Tanner & Davies, "Clinical longitudinal standards for height and height velocity for North American children." J Pediatr. 107(3):317-29 (Sep. 1985).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
van Gaal & De Leeuw, "Rationale and options for combination treatment of type 2 diabetes." Diabletologia 46 (Supplement 1):M44-M50 (Mar. 2003).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
Wahlin-Boll et al., "Impaired effect of sulfonylurea following increased dosage." Eur J Clin Pharmacol 22(1):21-25 (1982).

(56) References Cited

OTHER PUBLICATIONS

Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
Werner, "Preclinical pharmacology of the new GLP-1 receptor agonist AVE0010", Ann. Endocrinol. (Paris), 69(2):164-65 (Apr. 2008).
WHO, World Health Organization Media Center. Obesity and overweight, Fact Sheet No. 311. Updated Jan. 2015, pp. 1-5.
Wikipedia® entry for "Stratified sampling" Retrieved on Mar. 28, 2017, pp. 1-4.
Williams & Pickup, "Macrovascular disease in Diabetes." In handbook of Diabetes. 2nd ed. Williams G, Pickup JC, Eds. Oxford, UK, Blackwell Science Chapter 21; pp. 151-158 (1999).
Wolever et al., "Second-meal effect: low-glycemic-index foods eaten at dinner improve subsequent breakfast glycemic response." Am J Clin Nutr 48(4):1041-47 (Oct. 1988).
Yki-Järvinen, "Combination Therapies with insulin in type 2 diabetes." Diabetes Care 24(4):758-67 (Apr. 2001).
Yki-Järvinen et al., "Comparison of Bedtime insulin regimes in patients with type 2 diabetes mellitus." Annals of Internal Medicine 130(5):389-96 (Mar. 1999).
Zeitler et al., "ISPAD Clinical Practice Consensus Guidelines 2014. Type 2 diabetes in the child and adolescent." Pediatr Diabetes 15(Suppl 20):26-46 (Sep. 2014).
Zimmet et al., "The metabolic syndrome in children and adolescents." Lancet 369(9579):2059-61 (Jun. 2007).
Zinman et al., "The Effect of Adding Exenatide to a Thiazolidinedione in Suboptimally Controlled Type 2 Diabetes" Annals of Internal Medicine, 146(7):477-85 (Apr. 2007).
Final Office Action issued in U.S. Appl. No. 13/123,835; dated Nov. 18, 2015, pp. 1-16.
Non-Final Office Action issued in U.S. Appl. No. 15/340,969; dated Jul. 24, 2017, pp. 1-6.
Final Rejection issued in U.S. Appl. No. 13/382,442; dated Sep. 21, 2016, pp. 1-32.
Non-Final Office Action issued in U.S. Appl. No. 15/275,867; dated Jun. 1, 2017; pp. 1-11.
Non-Final Rejection issued in U.S. Appl. No. 13/509,507; dated Sep. 21, 2016, pp. 1-7.
Non-Final Rejection issued in U.S. Appl. No. 13/509,542; dated Nov. 23, 2016, pp. 1-34.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Jun. 30, 2016, pp. 1-9.
Non-Final Rejection issued in U.S. Appl. No. 13/467,707; dated Nov. 7, 2016, pp. 1-17.
Non-Final Rejection issued in U.S. Appl. No. 15/197,378; dated Jun. 15, 2017, pp. 1-13.
Non-Final Rejection in U.S. Appl. No. 13/633,563; dated Oct. 5, 2016, pp. 1-12.
Final Rejection in U.S. Appl. No. 13/633,496; dated Oct. 13, 2016, pp. 1-10.
Non-Final Rejection in U.S. Appl. No. 13/633,496; dated May 25, 2017, pp. 1-10.
Non-Final Rejection issued in U.S. Appl. No. 14/303,895; dated Mar. 24, 2017, pp. 1-17.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
International Search Report by the ISA for International Application No. PCT/EP2016/055267; dated May 20, 2016, pp. 1-7.
International Search Report by the ISA for International Application No. PCT/EP2016/055267; dated Jun. 7, 2016, pp. 1-8.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
ADIS R&D Profile "Insulin Glargine: Glargine, HOE 71GT15, HOE 71GT80, HOE 901", Drugs R&D 2(2):107-109 (Aug. 1999).
Ashford & Landi, "Stabilizing Properties of Tween 80 in Dilute Protein Solutions" Bull Parenteral Drug Assoc. 20(3):74-84 (May-Jun. 1966).
Aventis SEC Form 20-F; pp. 1-303 (Apr. 8, 2002).
Bam et al., "Tween protects recombinant human growth hormone against agitation-induced damage via hydrophobic interactions" J. Ph. Sci. 87(12):1554-59 (Dec. 1998).
Bam et al., "Stability of Protein Formulations: Investigation of Surfactant Effects by a Novel EPR Spectroscopic Technique," Pharmaceutical Research, 12(1):2-11 (Jan. 1995).
Bates et al., "Kinetics of hydrolysis of polyoxyethylene (20) sorbitan fatty acid ester surfactants," J. Pharmacy and Pharmacology 25(6):470-77 (Jun. 1973).
Berchtold & Hilgenfeld, "Binding of Phenol to R6 Insulin Hexamers" Biopolymers 51(2):165-72 (1999).
Bucceri et al., "Gallbladder and gastric emptying: relationship to cholecystokininemia in diabetics." Eur. J. Intern. Med. 13(2):123-28 (Mar. 2002).
Caprio, "Obesity and Type 2 Diabetes: The Twin Epidemic" Diabetes Spectrum 16(4):230 (2003).
Chawla et al., "Aggregation of Insulin, Containing Surfactants, in Contact with Different Materials", Diabetes 34(5):420-24 (May 1985).
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Colagiuri, "Diabesity: therapeutic options" Diabetes, Obesity and Metabolism 12(6):463-73 (Jun. 2010).
Definition of "hypoglycemia" Stedman's Medical Dictionary, 5th Edition, Japan, published on Feb. 20, 2002, p. 853; in Japanese, English translation also submitted.
Derewenda et al., "Phenol Stabilizes More Helix in a New Symmetrical Zinc Insulin Hexamer" Nature 338(6216):594-96 (Apr. 1989).
Drug Facts and Comparison; J. B. Lippincot Company, St. Louis, MO; pp. 1781-1790 (1988).
EMEA Public Statement on Insuman Infusat (Feb. 14, 2000), at http://www.ema.europa.eu/ema/index.jsp?curl=pages/news_and_events/news/2010/08/news_detail_001094jsp&mid=WC0b01ac058004d5c1 (accessed Jun. 1, 2017); pp. 1-27.
Excerpts from "Handbook of Pharmaceutical Excipients" 2nd Edition (eds. A. Wade and P.J. Weller) American Pharmaceutical Association, Washington, The Pharmaceutical Press, London; pp. 1-55 (1994).
Farag & Gaballa, "Diabesity: an overview of a rising epidemic" Nephrol Dial Transplant 26(1):28-35 (Jan. 2011; Epub Nov. 2, 2010).
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Gatlin & Gatlin, "Formulation and Administration Techniques to Minimize Injection Pain and Tissue Damage Associated with Parenteral Products" in Injectable Drug Development, Chapter 17; pp. 401-421 (eds. P.K. Gupta and G.A. Brazeau) (CRC Press) (1999).
Gillies et al, "Insulin Glargine" Drugs 59(2)L253-60 (Feb. 2000).
Grau & Saudek, "Stable Insulin Preparation for Implanted Insulin Pumps", Diabetes 36(12):1453-59 (Dec. 1987).

(56) References Cited

OTHER PUBLICATIONS

Gualandi-Signorini & Giorgi, "Insulin formulations—a review" European Review for Medical and Pharmacological Sciences 5:73-83 (2001).
Hallas-Moller, "The Lente Insulins", Diabetes 5:7-14 (Jan.-Feb. 1956).
Heile & Schneider, "The Evolution of Insulin Therapy in Diabetes Mellitus", J Fam Pract 61(5 Suppl.):S6-12 (May 2012).
INSUMAN INFUSAT entry in Rote Liste, one page (2001).
INSUMAN INFUSAT; FASS Entry for INSUMAN INFUSAT; pp. 1-6 (Jan. 2000). English translation of Jun. 5, 2017, pp. 1-8 also submitted.
Jones, "Insulin Glargine Aventis Pharma", IDrugs 3(9):1081-87 (Sep. 2000).
Jones et al. "Surfactant-Stabilized Protein Formulations: A Review of Protein-Surfactant interactions and Novel Analytical Methodologies," Therapeutic Protein & Peptide Delivery, ACS Symposium Series; Chapter 12, pp. 206-222 (1997).
Katakam et al., "Effect of Surfactants on the Physical Stability of Recombinant Human Growth Hormone" J Pharm Sci 84(6):713-16 (Jun. 1995).
Lantus® 100U/ml solution for injection (insulin glargine); published in vol. 24 No. 9 of Pract. Diab. Int. Nov./Dec. 2007, p. 472.
Lantus® entry in Physician's Desk Reference; pp. 1-6 (2001).
Lantus®—FDA Drug Approval Letter for Lantus® (NDA 02-1081) at https://www.accessdata.fda.gov/scripts/cder/daf/index.cfm?event=overview.process&ApplNo=021081 (accessed Jan. 25, 2018), pp. 1-5.
Lantus®—FDA Drug Approval Label for Lantus® (NDA 02-081) (Apr. 20, 2000) at https://www.accessdata.fda.gov/scripts/cder/daf/index.cfm?event=overview.process&ApplNo=021081 (accessed Jan. 25, 2018), pp. 1-14.
Lawson et al., "Coordination of gastric and gallbladder emptying after ingestion of a regular meal." Gastroenterology. 85(4):866-70 (Oct. 1983).
Lee et al., "Effect of Brij-78 on Systemic Delivery of Insulin from an Ocular Device" J Pharm Sci 86(4):430-33 (Apr. 1997).
Lee et al., "Review on the Systemic Delivery of Insulin via the Ocular Route" Int'l J Pharmaceutics 233(1-2):1-18 (Feb. 2002).
Lougheed et al., "Insulin Aggregation in Artificial Delivery Systems" Diabetologia 19(1):1-9 (Jul. 1980).
Manning et al., "Stability of Protein Pharmaceuticals," Pharm Research, 6(11):903-18 (Nov. 1989).
McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT01195454, NIH Clinical Trials, "Euglycemic clamp dose-response study comparing insulin glargine U300 with Lantus U100" last updated Sep. 3, 2010, pp. 1-3.
NCT00765817, Clinical Trials.gov "Addition of Exenatide to Insulin Glargine in Type 2 Diabetes Mellitus" last updated Oct. 26, 2016, last accessed Jan. 19, 2018, pp. 1-8.
Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).
Sanofi-aventis Press Release (Melia), "New Diabetes Compound AVE0010 Showed Clear Dose Response Results With Once-A-Day Injection in Phase IIb Study" San Francisco, California (Jun. 7, 2008) pp. 1-3.

Schmolka, "Poloxamers in the Pharmaceutical Industry" in Polymers for Controlled Drug Delivery, Chapter 10, pp. 189-214 (CRC Press) (1991).
Shi, "The Newest Handbook of Clinical Drugs" Military Medical Science Press, p. 809, (Jan. 2008). English translation submitted.
Tang, "Biotech Drugs—Introduction and Practice Handbook" Chemical Industry Press, pp. 635-636, (Jan. 2008). English translation submitted.
U.S. Appl. No. 15/803,589, filed Nov. 13, 2017, Hagendorf et al.
U.S. Appl. No. 15/730,033, filed Oct. 11, 2017, Niemoller et al.
U.S. Appl. No. 15/803,589, filed Nov. 3, 2017, Pharmaceutical Composition Comprising a GLP-1 Agonist, An Insulin and Methionine.
U.S. Appl. No. 15/730,033, filed Oct. 11, 2017, Pharmaceutical Combination for Improving Glycemic Control as Add-On Therapy to Basal Insulin.
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.
Meier et al., "Effect of lixisenatide vs liraglutide on glycaemic control, gastric emptying and safety parameters in optimised insuline glargine type 2 diabetes mellitus +/− metformin" Poster and Abstract 926, 50th EASD Annual Meeting, Vienna, Austria Sep. 15-19, 2014, pp. 1-3.
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Kondrat'ev, Methodical Guidelines—Ministry of Health Ukraine, one page, May 7, 2010. Accessed on Mar. 24, 2016, English translation provided.
Final Rejection in U.S. Appl. No. 13/633,563; dated Apr. 8, 2016, pp. 1-12.
Final Rejection in U.S. Appl. No. 13/633,496; dated Aug. 26, 2015, pp. 1-16.
Non-Final Rejection in U.S. Appl. No. 13/633,496; dated Apr. 21, 2016, pp. 1-12.
Final Rejection issued in U.S. Appl. No. 13/509,507; dated May 13, 2016, pp. 1-11.
Abraira et al., "Glycaemic separation and risk factor control in the Veterans Affairs Diabetes Trial: an interim report." Diabetes Obes Metab 11(2):150-56. (2009; Epub Jul. 29, 2008).
Ampudia-Blasco et al., "Basal Plus Basal-Bolus approach in type 2 diabetes." Diabetes Technol Ther. 13 Suppl 1:S75-83 (Jun. 2011).
Atkinson et al., "Validation of a general measure of treatment satisfaction, the Treatment Satisfaction Questionnaire for Medication (TSQM), using a national panel study of chronic disease." Health Qual Life Outcomes. 2:12, pp. 1-13 (Feb. 2004).
Beckman et al., "Diabetes and atherosclerosis: epidemiology, pathophysiology, and management." JAMA 287 (19):2570-81 (May 2002).
Brazier et al., "Testing the validity of the Eurogol and comparing it with the SF-36 health survey questionnaire." Qual Life Res 2(3):169-80 (Jun. 1993).
Byetta® Summary of product characteristics. Annex I, pp. 1-71, (2011).
Byetta® Product information. EMA pp. 1-2, accessed Jun. 10, 2016.
De Lemos et al., "Early intensive vs. a delayed conservative simvastatin strategy in patients with acute coronary syndromes: phase Z of the A to Z trial." JAMA 292(11):1307-16 (Sep. 2004; Epub Aug. 30, 2004).
Del Prato & Tiengo, "The importance of first-phase insulin secretion: implications for the therapy of type 2 diabetes mellitus." Diabetes Metab Res Rev. 17(3):164-74 (May-Jun. 2001).
Del Prato et al., "Global Partnership for Effective Diabetes Management. Tailoring treatment to the individual in type 2 diabetes practical guidance from the Global partnership for effective diabetes managment." Int J Clin Pract. 64 (3):295-304 (Feb. 2010).

(56) References Cited

OTHER PUBLICATIONS

DeWitt & Hirsch, "Outpatient insulin therapy in type 1 and type 2 diabetes mellitus: scientific review." JAMA 289 (17):2254-64 (May 2003).
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Encyclopedia of Drugs, "Metformin" Moscow, Drug Register of 2001, p. 549, English translation provided pp. 1-2.
EuroQol Group, "EuroQol—a new facility for the measurement of health-related quality of life." Health policy (Amsterdam, Netherlands) 16(3):199-208 (Dec. 1990).
FDA, Food and Drug Administration. Guidance for Industry—Diabetes Mellitus: Developing Drugs and Therapeutic Biologics for Treatment and Prevention. pp. 1-34 (Feb. 2008).
Gerstein et al., "Albuminuria and risk of cardiovascular events, death, and heart failure in diabetic and nondiabetic individuals." JAMA 286(4):421-6 (Jul. 2001).
Holman et al., "Three-year efficacy of complex insulin regimens in type 2 diabetes." N Engl J Med. 361(18):1736-47 (Oct. 2009; Epub Oct. 22, 2009).
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Juniper et al., "Determining a minimal important change in a disease-specific quality of life questionnaire." J Clin Epidemiol 47(1):81-87 (Jan. 1994).
King et al., Global burden of diabetes, 1995-2025. Prevalence, numerical estimates and projections. Diabetes Care 21(9):1414-21 (Sep. 1998).
Kolotkin et al., "Assessing impact of weight on quality of life." Obes Res. 3(1):49-56 (Jan. 1995).
Kolotkin et al., "Development of a brief measure to assess quality of life in obesity." Obes Res. 9(2):102-11 (Feb. 2001).
Korytkowski, "When oral agents fail: practical barriers to starting insulin." Int J Obes Relat Metab Disord. 26 Suppl 3:S18-24 (Sep. 2002).
Lovshin & Drucker, "Incretin-based therapy for type 2 diabetes mellitus." Nat. Rev. Endocrinol. 5(5):262-69 (May 2009).
McFarlane, "Insulin therapy and type 2 diabetes: management of weight gain," J Clin Hypertens (Greenwich). 11(10):601-7 (Oct. 2009).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Monnier & Colette, "Addition of rapid-acting insulin to basal insulin therapy in type 2 diabetes: indications and modalities." Diabetes Metab 32(1):7-13 (Feb. 2006).
Nathan et al., "Modern-day clinical course of type 1 diabetes mellitus after 30 years' duration: the diabetes control and complications trial/epidemiology of diabetes interventions and complications and Pittsburgh epidemiology of liabetes complications experience (1983-2005)." Arch Intern Med. 169(14):1307-16 (Jul. 2009).
Nowels et al., "Validation of the EQ-50 quality of life instrument in patients after myocardial infarction." Qual Life Res 14(1):95-105 (Feb. 2005).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Ray et al., "Effect of intensive control of glucose on cardiovascular outcomes and death in patients with diabetes mellitus: a meta-analysis of randomized controlled trials." Lancet 373(9677):1765-72 (May 2009).
Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Russell-Jones & Khan, Insulin-associated weight gain in diabetes: causes, effects and coping strategies. Diabetes Obes Metab.9(6):799-812 (Nov. 2007).
Merck Index, "Metformin", The Merck Index, 15th Edition (2013), RSC Publishing, 4 pages submitted, see p. 6009.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Seino et al., "Lixisenatide significantly improves glycemic control in Asian patients with T2DM insufficiently controlled on basal insulin ± SU." Diabetes, Abstract book for 71st Scientific Session. p. A76; Abstract 278-OR (2011).
Shaw et al., "US valuation of the EQ-5D health states: development and testing of the D1 valuation model." Med Care 43(3):203-20 (Mar. 2005).
Spertus et al., "Monitoring the quality of life in patients with coronary heart disease." Am J Cardiol. 74(12):1240-44 (Dec. 1994).
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Definition of "Combination", Concise Oxford English Dictionary, edited by A. Stevenson and M. Waite, Oxford University press, 12th Edition, Aug. 2011, 4 pages submitted, see p. 285.
Weir "Glucagon-like peptide-1 (7-37) actions on endocrine pancreas." Diabetes 38(3):338-42 (Mar. 1989).
WHO, World Health Organization Media Center. Diabetes Fact Sheet. Available from: http://www.who.int/mediacentre/factsheets/fs312/en/index.html. Accessed Jun. 13, 2016, pp. 1-6.
Wild et al., "Global prevalence of diabetes: estimates for the year 2000 and projections for 2030." Diabetes Care 27(5):1047-53 (May 2004).
Williams et al., "Macrovascular disease in Diabetes." In handbook of Diabetes. 4nd ed. Williams G, Pickup JC, Eds. Oxford, UK, Blackwell Science pp. 151-58 (2010).
Wright et al., U.K. Prospective Diabetes Study Group. "Sulfonylurea inadequacy: efficacy of addition of insulin over 6 years in patients with type 2 diabetes in the UK. Prospective Diabetes Study (UKPDS 57)." Diabetes Care 25 (2):330-36 (Feb. 2002).
Zimmet et al., "Global and societal implications of the diabetes epidemic." Nature 414(6865):782-87 (Dec. 2001).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Brange & Langkjaer, "Insulin Structure and Stability" Chapter 11; Pharm Biotechnol 5:315-50 (1993).
U.S. Appl. No. 13/382,772, filed May 29, 2012, Schoettle.
U.S. Appl. No. 13/382,442, filed Feb. 21, 2012, Schoettle.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Nov. 11, 2012, Becker et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niemoller et al.

(56) References Cited

OTHER PUBLICATIONS

U.S. Appl. No. 13/468,422, filed May 10, 2012, Silvestre et al.
U.S. Appl. No. 13/467,757, filed May 9, 2012, Silvestre et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 14/965,586, filed Dec. 10, 2015, Souhami et al.
U.S. Appl. No. 14/995,910, filed Jan. 14, 2016, Bergmann et al.
U.S. Appl. No. 15/068,286, filed Mar. 11, 2016, Roy et al.
U.S. Appl. No. 13/123,835, filed Sep. 30, 2011, Werner et al.
U.S. Appl. No. 13/633,496, filed Oct. 2, 2012, Stechl et al.
U.S. Appl. No. 13/661,476, filed Oct. 26, 2012, Silvestre et al.
U.S. Appl. No. 14/303,895, filed Jun. 13, 2014, Souhami et al.
Thurow & Geisen, "Stabilisation of dissolved proteins against denaturation at hydrophobic interfaces", Diabetologia 27(2)212-18 (Aug. 1984).
Wang, "Instability, Stabilization and Formulation of Liquid Protein Pharmaceuticals," Int'l J Pharm, 185(2)129-88 (Aug. 1999).
Wikipedia® entry for "Standard deviation" Retrieved on Oct. 10, 2017, pp. 1-3.
Non-Final Rejection issued in U.S. Appl. No. 13/382,442; dated Sep. 20, 2017, pp. 1-28.
Non-Final Rejection issued is U.S. Appl. No. 15/595,929; dated Sep. 20, 2017, pp. 1-9.
Non-Final Rejection issued in U.S. Appl. No. 15/237,285; dated Sep. 29, 2017, pp. 1-10.
Non-Final Rejection issued in U.S. Appl. No. 15/144,270; dated Dec. 13, 2017, pp. 1-25.
Non-Final Rejection issued in U.S. Appl. No. 14/220,562; dated Apr. 8, 2015, pp. 1-18.
Non-Final Rejection issued in U.S. Appl. No. 14/624,575; dated Mar. 26, 2015, pp. 1-14.
Non-Final Rejection issued in U.S. Appl. No. 15/162,563; dated Feb. 8, 2017, pp. 1-13.
Final Rejection issued in U.S. Appl. No. 15/162,563; dated Dec. 18, 2017, pp. 1-16.
Non-Final Office Action issued in U.S. Appl. No. 15/146,255; dated Sep. 18, 2017, pp. 1-10.
Final Rejection in U.S. Appl. No. 13/633,563; dated Apr. 28, 2017, pp. 1-12.
Non-Final Rejection issued in U.S. Appl. No. 14/995,910; dated Dec. 11, 2017, pp. 1-7.
Extended European Search Report for European Application No. 16 19 0103.8; dated Jun. 23, 2017, pp. 1-5.
Extended European Search Report for European Application No. 17 20 2727.8; dated Dec. 20, 2017, pp. 1-9.
Search Report in Chinese Patent Application No. 201410818149.0; dated Jan. 10, 2017, pp. 1-3. English translation submitted.
Search Report of the Intellectual Property Office of Singapore for Patent Application No. 10201403840V; search completed Nov. 21, 2017 and dated Jan. 4, 2017, pp. 1-3.
U.S. Appl. No. 15/162,563, dated May 23, 2016, Becker et al.
U.S. Appl. No. 15/893,577, dated Feb. 9, 2018, Becker et al.
Acunman et al., "Lixisenatide protects the neurovascular unit in diabetes retinopathy" Abstract & Poster 1045; EASD meeting in Lisbon 2017, 2 pages (Sep. 11-15, 2017).
Burgstaller et al., "Shedding Light on Insulin Aggregation with the Litesizer 500" Anton Paar—Application Report, pp. 1-4 (2014).
Chiasson "Early Insulin Use in Type 2 Diabetes—What are the cons?" Diabetes Care 32(Suppl. 2):S270-S274 (Nov. 2009).
Dietrich et al., "The DPP4 Inhibitor Linagliptin Protects from Experimental Diabetic Retinopathy" PLoS ONE 11(12): e1067853, pp. 1-17 (Dec. 2016).
European Medicines Agency, LYXUMIA 10/20 micrograms solution for injection, Summary of Product Characteristics, Date of first authorisation: Feb. 1, 2013, pp. 1-82 (retrieved from the Internet on Mar. 12, 2018).
Hernandez et al., "Topical Administration of GLP-1 Receptor Agonists Prevents Retinal Neurodegeneration in Experimental Diabetes" Diabetes 65:172-187 (Jan. 2016).
Lee et al., "Epidemiology of diabetic retinopathy, diabetic macular edema and related vision loss" Eye and Vision 2:17, pp. 1-25 (2015).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Oct. 11, 2016, Retrieved Mar. 30, 2018, pp. 1-11.
NCT01572649, "Evaluation of the Blood Levels of the Drug (Lixisenatide), the Plasma Glucose Levels and Safety in Paediatric and Adult Patients with Type 2 Diabetes", last updated May 23, 2014; accessed Jul. 5, 2018, pp. 1-6.
Nowotny et al., "Advanced Glycation End Products and Oxidative Stress in Type 2 Diabetes Mellitus" Biomolecules 5:194-222 (Mar. 2015).
Regard et al., "Anatomical profiling of G protein-coupled receptor expression" Cell 135(3):561-571 (Oct. 2008).
Soeborg et al., "Absorption kinetics of insulin after subcutaneous administration" European Journal of Pharmaceutical Sciences 36(1):78-90 (Jan. 2009; Epub Nov. 5, 2008).
SOLIQUA® Product Information; pp. 1-33 (Oct. 2017).
SOLIQUA® Consumer Medicine Information (CMI); pp. 1-7 (Oct. 2017).
SOLIQUA® Summary of Product Characteristics; pp. 1-74 (Jan. 2017).
Stitt et al., "The progress in understanding and treatment of diabetic reinopathy" Progress in Retinal and Eye Research 51:156-186 (2016; Epub Aug. 18, 2015).
Urakami et al., "Pharmacologic treatment strategies in children with type 2 diabetes mellitus", Clin Pediatr Endocrinol., 22(1):1-8 (Jan. 2013).
Yu et al., "Glucagon-like peptide-1 prevented abdominal aortic aneurysm development in rats" Sugr. Today 446:1099-1107 (2016).
Final Rejection issued in U.S. Appl. No. 13/382,442; dated Apr. 16, 2018, pp. 1-28.
Non-Final Rejection issued in U.S. Appl. No. 15/411,557; dated Mar. 19, 2018, pp. 1-11.
Final Rejection issued in U.S. Appl. No. 15/162,563; dated Aug. 9, 2017, pp. 1-11.
Final Rejection issued in U.S. Appl. No. 15/162,563; dated Apr. 17, 2018, pp. 1-16.
Extended European Search Report for European Application No. 17 17 4341; dated Nov. 7, 2017, pp. 1-1.
Search Report of the Intellectual Property Office of Singapore for Patent Application No. 11201704678S; search completed May 25, 2018 and dated Jun. 14, 2018, pp. 1-2.
Intellectual Property Office of Singapore for Patent Application No. 11201705755U search completed Jun. 5, 2018 and dated Jun. 20, 2018, pp. 1-2.

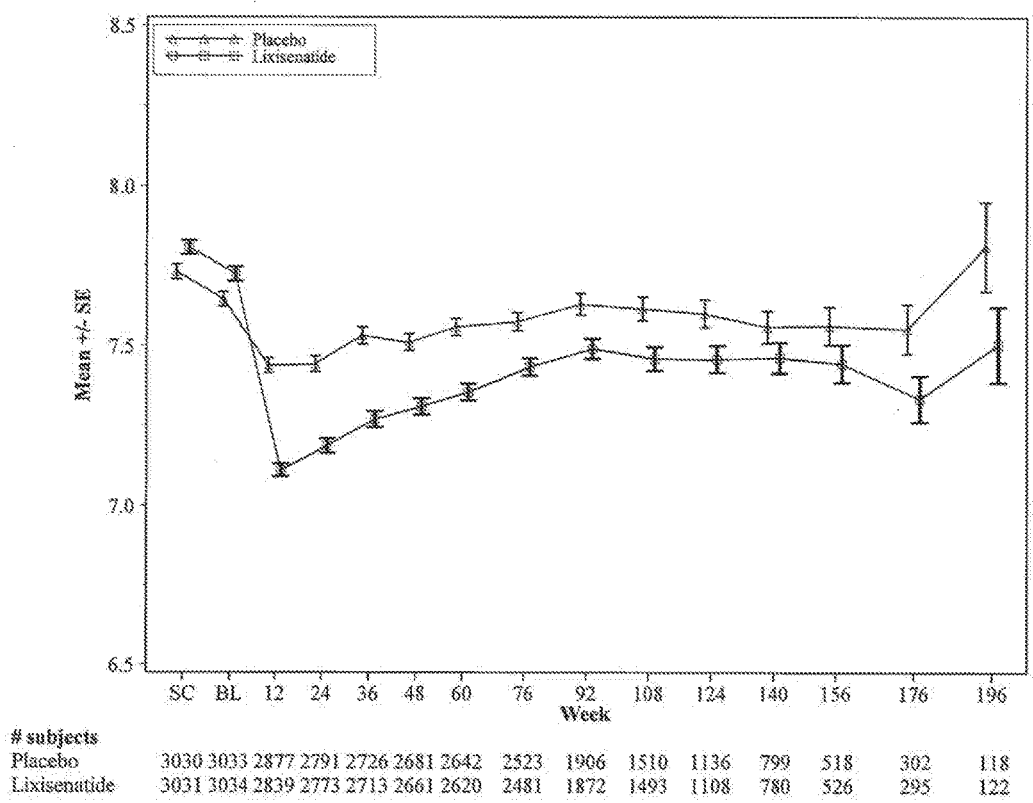

TREATMENT OF TYPE 2 DIABETES MELLITUS PATIENTS

This application claims the benefit of European Application No. 15 159 733.3, filed Mar. 18, 2015, and European Application No. 15 191 585.7, filed Oct. 27, 2015, the disclosures of which are herein incorporated by reference in their entirety.

Subject of the present invention is desPro$^{36}$Exendin-4(1-39)-Lys$_6$-NH$_2$ (AVE0010, lixisenatide) or/and a pharmaceutically acceptable salt thereof, for the reduction of progression of urinary albumin excretion in a type 2 diabetes mellitus patient.

Yet another aspect of the present invention is lixisenatide or/and a pharmaceutically acceptable salt thereof, for use in the reduction of cardiovascular morbidity or/and cardiovascular mortality in a type 2 diabetes mellitus patient who experienced at least one acute coronary syndrome event.

Yet another aspect is a method for reduction of cardiovascular morbidity or/and cardiovascular mortality in a type 2 diabetes mellitus patient who experienced at least one acute coronary syndrome event, said method comprising administering lixisenatide or/and a pharmaceutically acceptable salt thereof.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro- and macrovascular damages that possibly manifest themselves in retinopathies, nephropathies or neuropathies and lead to blindness, renal failure and the loss of extremities and are accompanied by an increased risk of cardiovascular diseases.

In the past two decades the prevalence of type 2 diabetes has increased to epidemic proportions worldwide; the number of subjects with type 2 diabetes is set to rise from the current estimate of 150 million to 220 million in 2010 and 300 million in 2025. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications, leading to a decreased life expectancy. This is mainly due to cardiovascular deaths with a risk of coronary heart disease increased by two- to fourfold in this population.

Results from large controlled trials as well as smaller studies and numerous epidemiologic studies have demonstrated that intensive glycemic control decreases the risk of microvascular complications. On the basis of these findings the American Diabetes Association (ADA) and the International Diabetes Federation recommend a tight glycemic control with an HbA1c target <7% and <6.5%, respectively. Although an intensive glycemic management has also been shown to have beneficial effect on cardiovascular disease (CVD) complications in type 1 diabetes, there is still controversy whether this demonstration can also apply in patients with type 2 diabetes. Recent individual studies conducted in type 2 diabetes have failed to demonstrate a beneficial effect of intensive diabetes therapy on CVD. However meta-analyses recently performed, showed a reduction in coronary events; effect on cardiovascular death or all-cause mortality was less evident.

New types of antidiabetic medicines, such as GLP-1 receptor agonists may achieve physiological blood glucose-insulin response with a low risk of hypoglycemia and may offer a valuable new therapeutic approach. These drugs reduce blood glucose by glucose dependent stimulation of insulin release and inhibition of glucagon secretion, which decreases prandial blood glucose excursion and hepatic glucose production; they also delay gastric emptying and reduce appetite which is associated with weight loss.

Effects of lixisenatide on glycemia and weight reduction with a favourable safety and tolerability profile were evidenced in the dose-ranging DRI6012 study. This study was a placebo-controlled, randomized, parallel-group, 12 treatments groups [8 AVE0010 active treatment groups (5, 10, 20, or 30 µg BID before breakfast and dinner, or 5, 10, 20, or 30 µg QD before breakfast with volume-matched placebo before dinner) or volume-matched placebo groups], 13-week treatment, dose finding study being conducted on 542 patients with type 2 diabetes treated with metformin. The adjusted HbA1c mean change from baseline to endpoint at week 13 was −0.69% with lixisenatide 20 µg QD from a mean baseline of 7.58% (p<0.0001).

The example of the present invention is a secondary prevention study with the objective to evaluate lixisenatide in type 2 diabetic patients who recently experienced an acute coronary syndrome (ACS) event. The term acute coronary syndrome, as used herein, includes unstable angina, non-ST segment elevation myocardial infarction (NSTEMI), and ST segment elevation myocardial infarction (STEMI) and will allow covering a large spectrum of patients for whom there is a common aetiology in the formation of thrombus on an inflamed and complicated atheromatous plaque. The requirement for either an elevated cardiac biomarker, or an occluded coronary artery at emergent angiography, is consistent with this pathology, and will reduce the incidence of false positives based on clinical history and/or ECG findings alone. Patients with ACS are at high risk for recurrence of cardiovascular events, indeed the 30-day and 6-months mortality is high, particularly in patients with NSTEMI (10.4% and 18.7% at 30 days and 6 months, respectively) and STEMI (12.9% and 19.2% at 30 days and 6 months, respectively) compared with unstable angina (4.5% and 8.6% at 30 days and 6 months, respectively) (20). In addition, it is also known that patients with diabetes have a substantially greater risk of death and ischemic complications following an ACS event than patients without diabetes (21).

The primary efficacy endpoint is to evaluate the effect of lixisenatide compared to placebo on the occurrence of cardiovascular death, non-fatal myocardial infarction, non-fatal stroke, and hospitalization for unstable angina. Based on published data the estimated cardiovascular event rate in the proposed population is to be approximately 10% within the first year after the ACS event (22) (23) (24) (25).

A secondary objective of this study is to evaluate the effect of lixisenatide on the urinary albumin excretion (calculated from the urinary albumin/creatinine ratio) which is a marker of development of nephropathy in type 2 diabetes. It is well known that for patients with type 2 diabetes an increased incidence of cardiovascular mortality is observed in those with microalbuminuria. This observation was confirmed in a meta-analysis of 11 longitudinal studies that included 2,138 patients with type 2 diabetes and microalbuminuria followed for a mean of 6.4 years. The overall odds ratio was 2.0 (95% CI 1.4-2.7) for cardiovascular morbidity or mortality, and 2.4 (95% CI 1.8-3.1) for total mortality (26). Recent studies suggest that an increase in the urinary albumin excretion, even within the normal range, is also associated with a greater risk of cardiovascular disease (27), (28). Blood pressure lowering and blood glucose lowering have shown a reduction of albuminuria as well as a reduction of the development of nephropathy (6), (7), (29), (30).

It was surprisingly found that lixisenatide reduces the progression of urinary albumin excretion (albuminuria).

Metformin is a biguanide hypoglycemic agent used in the treatment of non-insulin-dependent diabetes mellitus (type 2 diabetes mellitus) not responding to dietary modification. Metformin improves glycemic control by improving insulin sensitivity and decreasing intestinal absorption of glucose. Metformin is usually administered orally. However, control of type 2 diabetes mellitus in obese patients by metformin may be insufficient. Thus, in these patients, additional measures for controlling type 2 diabetes mellitus may be required.

Metformin is the international nonproprietary name of 1,1-dimethylbiguanide (CAS number 657-24-9).

The compound desPro$^{36}$Exendin-4(1-39)-Lys$_6$-NH$_2$ (lixisenatide) is a Glucagon-like peptide 1 (GLP-1) receptor agonists and is being developed for the treatment of patients with type 2 diabetes mellitus (T2DM). Lixisenatide is a derivative of Exendin-4. Lixisenatide is disclosed as SEQ ID NO:93 in WO 01/04156:

```
lixisenatide (44 amino acids)
SEQ ID NO: 1:
H-G-E-G-T-F-T-S-D-L-S-K-Q-M-E-E-E-A-V-R-L-F-I-
E-W-L-K-N-G-G-P-S-S-G-A-P-P-S-K-K-K-K-K-K-NH₂ exendin-4 (39 amino acids)
SEQ ID NO: 2:
H-G-E-G-T-F-T-S-D-L-S-K-Q-M-E-E-E-A-V-R-L-F-I-
E-W-L-K-N-G-G-P-S-S-G-A-P-P-P-S-NH₂
```

Exendins are a group of peptides which can lower blood glucose concentration. Lixisenatide is characterised by C-terminal truncation of the native Exendin-4 sequence. Lixisenatide comprises six C-terminal lysine residues not present in Exendin-4.

Lixisenatide is also termed des-38-proline-exendin-4 (*Heloderma suspectum*)-(1-39)-peptidylpenta-L-lysyt-L-lysinamide (CAS number 320367-13-3).

An aspect of the present invention is the use of lixisenatide or/and a pharmaceutically acceptable salt thereof, in the reduction of cardiovascular morbidity or/and cardiovascular mortality in a type 2 diabetes mellitus patient who experienced at least one acute coronary syndrome event.

In particular, lixisenatide or/and a pharmaceutically acceptable salt thereof is used for reduction of the 30-day or/and the 6-months mortality in a type 2 diabetes mellitus patient who experienced at least one acute coronary syndrome event.

In particular, reduction of cardiovascular morbidity or/and cardiovascular mortality includes reduction of the risk of a cardiovascular event, more particular within one year after the at least one acute coronary syndrome event.

In the present invention, the cardiovascular event can include death, non-fatal myocardial infarction, non-fatal stroke, unstable angina, hospitalization for unstable angina, non-fatal heart failure, hospitalization for heart failure or/and coronary revascularization procedure.

In the present invention, the cardiovascular event can include death, non-fatal myocardial infarction, non-fatal stroke, unstable angina, or/and non-fatal heart failure.

In the present invention, the cardiovascular event can a major adverse cardiovascular event (MACE). A MACE can be one of cardiovascular death (CV death), non-fatal myocardial infarction (non-fatal MI), and non-fatal stroke.

According to the present invention, the risk of the cardiovascular event can be expressed as the expected rate of cardiovascular events, for example for a period of 1 year.

In particular, the type 2 diabetes mellitus patient to be treated according to the present invention experienced the at least one acute coronary syndrome event within 1, within 2, within 3, within 4, within 5 or within 6 months prior to or at the onset of treatment with lixisenatide or/and the pharmaceutically acceptable salt thereof. It is preferred that the type 2 diabetes mellitus patient to be treated according to the present invention experienced the at least one acute coronary syndrome event within 6 months prior to or at the onset of treatment with lixisenatide or/and the pharmaceutically acceptable salt thereof.

In particular, the at least one acute coronary syndrome event according to the present invention has been diagnosed within 1, within 2, within 3, within 4, within 5 or within 6 months prior to or at the onset of treatment with lixisenatide or/and the pharmaceutically acceptable salt thereof.

According to the present invention, the at least one acute coronary syndrome event can be a spontaneous acute coronary syndrome event.

According to the present invention, the at least one acute coronary syndrome event can include an ST-segment elevation myocardial infarction.

According to the present invention, the at least one acute coronary syndrome event can include a non-ST-segment elevation myocardial infarction.

According to the present invention, the at least one acute coronary syndrome event can include an unstable angina.

According to the present invention, the at least one acute coronary syndrome event can include one selected from the group consisting of an ST-segment elevation myocardial infarction, non-ST-segment elevation myocardial infarction and unstable angina.

According to the present invention, the at least one acute coronary syndrome event can be a biomarker-proven or biomarker-positive acute coronary syndrome event (ACS event). The at least one ACS event can be an ACS event associated with a positive diagnosis of at least one cardiac biomarker, such as troponin or/and CK-MB. In particular, there must be an elevation of the at least one cardiac biomarker, in particular troponin or/and CK-MB, above the normal reference ranges.

According to the present invention, the ACS event may be a class I, II, III or IV ACS event according to the New York Heart Association (NYHA). This classification is known to the skilled person. Disclosure of Class I to IV ACS events according to the New York Heart Association can, for example, be found in "The Criteria Committee of the New York Heart Association. Nomenclature and Criteria for Diagnosis of Diseases of the Heart and Great Vessels. 9th ed. Boston, Mass.: Little, Brown & Co: 1994:253-256".

Class I to IV ACS events according to the New York Heart Association can be defined as follows:

| Functional Capacity Objective | Assessment |
| --- | --- |
| Class I. Patients with cardiac disease but without resulting limitation of physical activity. Ordinary physical activity does not cause undue fatigue, palpitation, dyspnea, or anginal pain. | A. No objective evidence of cardiovascular disease. |

-continued

| Functional Capacity Objective | Assessment |
| --- | --- |
| Class II. Patients with cardiac disease resulting in slight limitation of physical activity. They are comfortable at rest. Ordinary physical activity results in fatigue, palpitation, dyspnea, or anginal pain. | B. Objective evidence of minimal cardiovascular disease. |
| Class III. Patients with cardiac disease resulting in marked limitation of physical activity. They are comfortable at rest. Less than ordinary activity causes fatigue, palpitation, dyspnea, or anginal pain. | C. Objective evidence of moderately severe cardiovascular disease. |
| Class IV. Patients with cardiac disease resulting in inability to carry on any physical activity without discomfort. Symptoms of Heart failure or the anginal syndrome may be present even at rest. If any physical activity is undertaken, discomfort is increased. | D. Objective evidence of severe cardiovascular disease. |

According to the present invention, the ACS event may also be a class I, II, III or IV angina pectoris according to the Canadian Cardiovascular Society. This classification is known to the skilled person. Disclosure of class I to IV of angina pectoris according to the Canadian Cardiovascular Society can be found in Campeau Lucien, Grading of Angina Pectons. Circulation, 1976; 54:522-3.

Class I to IV of angina pectoris according to the Canadian Cardiovascular Society can also be termed grade I to IV angina pectoris.

Class I to IV of angina pectoris according to the Canadian Cardiovascular Society can be defined as follows:

Class I: Ordinary physical activity does not cause angina, such as walking and climbing stairs. Angina with strenuous or rapid or prolonged exertion at work or recreation.

Class II: Slight limitation of ordinary activity. Walking or climbing stairs rapidly, walking uphill, walking or stair climbing after meals, or in cold, in wind or under emotional stress, or only during the few hours after awakening. Walking more than two blocks on the level and climbing more than one flight of ordinary stairs at a normal pace and in normal conditions.

Class III: Marked limitation of ordinary physical activity. Walking one or two blocks on the level and climbing one flight of stairs in normal conditions and at normal pace.

Class IV: Inability to carry out any physical activity without discomfort; angina may be present at rest. There are four sub-groups in CCS Class IV. Groups A to D:

A: Admitted to hospital, becomes relatively asymptomatic with aggressive medical therapy, and may be managed on an outpatient basis.

B: Admitted to hospital, continues to have angina despite aggressive medical therapy and cannot be safely discharged home, but does not require IV nitroglycerin.

C: Admitted to hospital and maximal medical therapy, including IV nitroglycerin, fails to control symptoms.

D: Patient in shock.

"At least one acute coronary syndrome event", as used herein, includes an acute coronary syndrome event, which can be the first acute coronary syndrome event the patient has experienced.

According to the present invention, the patient to be treated according to the present invention has a risk of cardiovascular death, non-fatal myocardial infarction, non-fatal stroke, unstable angina, hospitalization for unstable angina, non-fatal heart failure, hospitalization for heart failure or/and coronary revascularization procedure.

According to the present invention, the patient to be treated according to the present invention has a risk of cardiovascular death, non-fatal myocardial infarction, non-fatal stroke, unstable angina, or/and non-fatal heart failure.

Another aspect of the present invention is the use of lixisenatide or/and a pharmaceutically acceptable salt thereof, for the treatment of the risk of cardiovascular death, non-fatal myocardial infarction, non-fatal stroke, unstable angina, hospitalization for unstable angina, non-fatal heart failure, hospitalization for heart failure or/and revascularization procedure in a type 2 diabetes mellitus patient who experienced at least one acute coronary syndrome event. The type 2 diabetes mellitus patient may be a patient as described herein. The at least one acute coronary syndrome event may be at least one acute coronary syndrome event as described herein.

Another aspect of the present invention is the use of lixisenatide or/and a pharmaceutically acceptable salt thereof, for the treatment of the risk of cardiovascular death, non-fatal myocardial infarction, non-fatal stroke, unstable angina, or/and non-fatal heart failure in a type 2 diabetes mellitus patient who experienced at least one acute coronary syndrome event. The type 2 diabetes mellitus patient may be a patient as described herein. The at least one acute coronary syndrome event may be at least one acute coronary syndrome event as described herein.

In particular the treatment according to the present invention of the risk of cardiovascular death, non-fatal myocardial infarction, non-fatal stroke, unstable angina, hospitalization for unstable angina, non-fatal heart failure, hospitalization for heart failure or/and revascularization procedure reduces cardiovascular morbidity or/and cardiovascular mortality.

In particular the treatment according to the present invention of the risk of cardiovascular death, non-fatal myocardial infarction, non-fatal stroke, unstable angina, or/and non-fatal heart failure reduces cardiovascular morbidity or/and cardiovascular mortality.

According to the present invention, the revascularization procedure can be a percutaneous coronary intervention or coronary artery bypass grafting.

The treatment with lixisenatide or/and the pharmaceutically acceptable salt thereof according to the present invention can reduce the blood plasma concentration of hs-CRP, BNP or/and NT-proBNP.

Yet another aspect of the present invention is the use of lixisenatide or/and a pharmaceutically acceptable salt thereof, for reduction of the blood plasma concentration of hs-CRP. BNP or/and NT-proBNP.

According to the present invention, the type 2 diabetes mellitus patient can have a cardiovascular disease history prior to the at least one acute coronary syndrome event. In particular, the cardiovascular disease history includes at least one of coronary heart disease, cerebrovascular disease, peripheral artery disease, and cardiac arrhythmia.

According to the present invention, the type 2 diabetes mellitus patient can be a patient that has been diagnosed with a cardiovascular disease prior to the at least one acute coronary syndrome event. The cardiovascular disease can include at least one of coronary heart disease, cerebrovascular disease, peripheral artery disease, and cardiac arrhythmia.

According to the present invention, lixisenatide or/and a pharmaceutically acceptable salt thereof, can reduce the progression of urinary albumin excretion in a type 2 diabetes mellitus patient as described herein. The urinary albumin/creatinine ratio (UACR) increased in both treatment groups (24% and 34% change from baseline for the lixisenatide and placebo groups, respectively). Surprisingly, a smaller increase in the lixisenatide group as compared to the placebo group (the difference between lixisenatide versus placebo in the percent change from baseline of UACR was −0.10% with 95% CI: −0.17, −0.03) has been observed. Therefore, lixisenatide is capable of decreasing the worsening of albuminuria in type 2 diabetes patients, in particular in type 2 diabetes patients as described herein. The type 2 diabetes mellitus patient, as described herein, may suffer from microalbuminuria with an urinary albumin to creatinine ratio (UACR) of ≥30 to <300 mg/g, or the patient may suffer from macroalbuminuria with an urinary albumin to creatinine of ≥300 mg/g, as described herein. The patient may also suffer from mild renal impairment with a glomerular filtration rate of ≥60 to <90 mL/min/1.73 m$^2$, or from a moderate renal impairment with a glomerular filtration rate of ≥30 to <60 mL/min/1.73 m$^2$, or from a severe renal impairment with a glomerular filtration rate of >15 to <30 mL/min/1.73 m$^2$.

Yet another aspect of the present invention is the use of lixisenatide or/and a pharmaceutically acceptable salt thereof, for the reduction of urinary albumin excretion in a type 2 diabetes mellitus patient, as described herein.

Lixisenatide can also be used for the reduction of progression of urinary albumin excretion in a type 2 diabetes mellitus patient, as described herein.

Urinary albumin excretion is also termed albuminuria.

The type 2 diabetes mellitus patient suffering from albuminuria can be a patient as described herein. In particular, the patient suffering from urinary albumin excretion can have experienced at least one acute coronary syndrome event, as described herein.

In particular, the patient suffers from microalbuminuria with an urinary albumin to creatinine ratio of ≥30 to <300 mg/g, or the patient suffers from macroalbuminuria with an urinary albumin to creatinine ratio of ≥300 mg/g.

In particular, the patient suffers from mild renal impairment with a glomerular filtration rate of ≥60 to <90 mL/min/1.73 m$^2$, or the patient suffers from a moderate renal impairment with a glomerular filtration rate of ≥30 to <60 mL/min/1.73 m$^{2'}$, or the patient suffers from a severe renal impairment with a glomerular filtration rate of >15 to <30 mL/min/1.73 m$^2$.

The patient suffering from type 2 diabetes mellitus to be treated according to the present invention may be obese. A patient can be considered as obese if the body mass index is at least 30 kg/m$^2$. In the present invention, an obese patient may have a body mass index of at least 30 kg/m$^2$ or at least 31 kg/m$^2$. It is preferred that that the patient has a body mass index of at least 31 kg/m$^2$.

The patient suffering from type 2 diabetes mellitus to be treated according to the present invention preferably does not receive an antidiabetic treatment, for example by insulin or/and related compounds, or/and by one or more oral antidiabetic compounds, such as metformin, sulfonylurea or/and a glinide.

According to the present invention, lixisenatide or/and the pharmaceutically acceptable salt thereof may be administered in combination with (i) metformin or/and a pharmaceutically acceptable salt thereof,
(ii) insulin or/and a pharmaceutically acceptable salt thereof,
(iii) a glinide or/and a pharmaceutically acceptable salt thereof, or/and
(iv) a sulfonylurea or/and a pharmaceutically acceptable salt thereof.

The insulin to be administered in combination with lixisenatide or/and the pharmaceutically acceptable salt thereof may be a premixed, rapid-acting, or regular insulin.

The patient to be treated according to the present invention may be a subject suffering from type 2 diabetes mellitus, wherein type 2 diabetes mellitus is not adequately controlled by treatment with (a) metformin or/and a pharmaceutically acceptable salt thereof,
(b) insulin or/and a pharmaceutically acceptable salt thereof,
(c) a glinide or/and a pharmaceutically acceptable salt thereof, or/and
(d) a sulfonylurea or/and a pharmaceutically acceptable salt thereof, in particular prior to the onset of the treatment according to the present invention.

In particular, the type 2 diabetes mellitus is not adequately controlled by monotherapy with (a) metformin or/and a pharmaceutically acceptable salt thereof,
(b) insulin or/and a pharmaceutically acceptable salt thereof,
(c) a glinide or/and a pharmaceutically acceptable salt thereof, or
(d) a sulfonylurea or/and a pharmaceutically acceptable salt thereof, in particular prior to the onset of the treatment according to the present invention.

In the present invention, "not adequately controlled" by the treatment with compound (a), (b), (c) or/and (d), or with monotherapy with compound (a), (b), (c) or (d), as indicated above, means in particular that this treatment is not sufficient to remove the symptoms of diabetes mellitus. More particular, "not adequately controlled" by the treatment with compounds (a), (b), (c) or/and (d), or with monotherapy with compound (a), (b), (c) or (d), as indicated above, means that the patient does not reach normoglycemic values in terms of, for example, HbA1c value or/and fasting plasma glucose concentration.

The term "not adequately controlled" by the treatment with compounds (a), (b), (c) or/and (d), or with monotherapy with compound (a), (b), (c) or (d), as indicated above, in particular relates to the period prior to the treatment according to the present invention. It can be diagnosed prior to the treatment according to the present invention if the therapy with compounds (a), (b), (c) or/and (d), as indicated above adequately controls the type 2 diabetes mellitus or not. For example, such diagnosis may be performed within 1 month, within 2 months or within 3 months prior to the treatment of the present invention with lixisenatide or/and a pharmaceutically acceptable salt thereof.

In particular, the type 2 diabetes mellitus patient does not receive lixisenatide or/and a pharmaceutically acceptable salt thereof, prior to the onset of the treatment according to the present invention.

In the present invention, normoglycemic values are blood glucose concentrations of in particular 60-140 mg/dl (corresponding to 3.3 to 7.8 mmol/L).

Criteria for a type 2 diabetes mellitus diagnosis include:

the fasting plasma glucose concentration (FPG) is a ≥7.0 mmol/L (126 mg/dl), or the post challenge plasma glucose concentration is >11.1 mmol/L (200 mg/dl), performed as described by the World Health Organization (Definition, Diagnosis and Classification of Diabetes Mellitus and its Complications. Part 1: Diagnosis and Classification of Diabetes Mellitus. WHO/NCD/NCS/99.2. Geneva; 1999), using a glucose load containing the equivalent of 75 g anhydrous glucose dissolved in water, or HbA1c values of ≥6.5%, or symptoms of diabetes and a casual plasma glucose ≥200 mg/dl (11.1 mmol/L).

These criteria are described in the Global IDF/ISPAD Guideline for Diabetes in Childhood and Adolescence (International Diabetes Federation, ISBN 2-930229-72-1).

The diagnosis of type 2 Diabetes should not be based on a single plasma glucose concentration. Diagnosis may require continued observation with fasting and/or postprandial blood glucose levels and/or an oral glucose tolerance test.

According to Craig (Pediatric Diabetes 2014: 15 (Suppl. 20): 4-17), fasting plasma glucose (FPG can be classified as follows:

FPG<5.6 mmol/L (100 mg/dL)=normal fasting glucose concentration.

FPG 5.6 to 6.9 mmol/L (100-125 mg/dL)=impaired fasting glucose concentration.

FPG≥7.0 mmol/L (126 mg/dL)=provisional diagnosis of diabetes (the diagnosis must be confirmed, as described above)

Impaired glucose tolerance (IGT) and impaired fasting glucose concentration (IFG) are intermediate stages in the natural history of disordered carbohydrate metabolism between normal glucose homeostasis and diabetes.

In the present invention, normoglycemic glucose concentrations can include impaired glucose concentrations, as described herein.

In the present invention, normoglycemic values of fasting plasma glucose are blood glucose concentrations of in particular <5.6 mmol/L or <7.0 mmol/L.

By the treatment according to the present invention, adequate control of type 2 diabetes mellitus may be achieved in patients not adequately controlled with metformin monotherapy, for instance with a dose of at least 1.0 g/day metformin or at least 1.5 g/day metformin for at least 3 months, or/and a dose of at the maximum 2.0 g/day metformin for at least 3 months.

In the present invention, the type 2 diabetes patient to be treated may have a HbA1c value in the range of 7% to 10%. In particular the patient to be treated may have a $HbA_{1c}$ value of at least about 7%, at least about 7.5%, at least about 7.6%, at least about 7.7%, at least about 8%, at least about 8.5%, or at least about 9%, more particular prior to the onset of treatment with lixisenatide or/and the pharmaceutically acceptable salt thereof. These HbA1c values exceed normoglycemic values.

In the present invention, the type 2 diabetes patient to be treated may have a HbA1c value in the range of 7% to 10%, or a $HbA_{1c}$ value of at least about 7%, at least about 7.5%, at least about 7.6%, at least about 7.7%, at least about 8%, at least about 8.5%, or at least about 9% if the patient is treated with (a) metformin or/and a pharmaceutically acceptable salt thereof, (b) insulin or/and a pharmaceutically acceptable salt thereof, (c) a glinide or/and a pharmaceutically acceptable salt thereof, or/and (d) a sulfonylurea or/and a pharmaceutically acceptable salt thereof, or if the patient is treated with monotherapy with a compound selected from compound (a), (b), (c) or (d). In particular, the patient may have this value by treatment with compounds (a), (b), (c) or/and (d), or with monotherapy with compound (a), (b), (c) or (d), prior to the onset of treatment according to the present invention with lixisenatide or/and a pharmaceutically acceptable salt thereof, indicating that the type 2 diabetes mellitus is not adequately controlled.

In particular, a patient receiving metformin monotherapy (in particular before onset of therapy according to the present invention) may have a HbA1c value in the range of 7% to 10%. In particular the patient receiving metformin monotherapy may have a $HbA_{1c}$ value of at least about 7%, at least about 7.5%, at least about 7.6%, at least about 7.7%, at least about 8%, at least about 8.5%, or at least about 9%, indicating that the type 2 diabetes mellitus is not adequately controlled by metformin monotherapy.

In the present invention, the type 2 diabetes patient to be treated may have a fasting plasma glucose concentration of at least 8 mmol/L or at least 8.5 mmol/L in particular prior to the onset of treatment with lixisenatide or/and the pharmaceutically acceptable salt thereof. These plasma glucose concentrations exceed normoglycemic concentrations.

In the present invention, the type 2 diabetes patient to be treated may have a fasting plasma glucose concentration of at least 8 mmol/L or at least 8.5 mmol/L if the patient is treated with (a) metformin or/and a pharmaceutically acceptable salt thereof, (b) insulin or/and a pharmaceutically acceptable salt thereof, (c) a glinide or/and a pharmaceutically acceptable salt thereof, or/and (d) a sulfonylurea or/and a pharmaceutically acceptable salt thereof, or if the patient is treated with monotherapy with a compound selected from compound (a), (b), (c) or (d). In particular, the patient may have this fasting plasma glucose concentration by treatment with compounds (a), (b), (c) or/and (d), or with monotherapy with compound (a), (b), (c) or (d), prior to the onset of treatment according to the present invention with lixisenatide or/and a pharmaceutically acceptable salt thereof, indicating that the type 2 diabetes mellitus is not adequately controlled.

In particular, a patient receiving metformin monotherapy (in particular before onset of therapy according to the present invention) may have a fasting plasma glucose concentration of at least 8 mmol/l, or at least 8.5 mmol/L, indicating that the type 2 diabetes mellitus is not adequately controlled by metformin monotherapy.

In the present invention, the type 2 diabetes patient to be treated may have an age of at least 60 years.

In the present invention, metformin includes pharmaceutically acceptable salts thereof. The person skilled in the art knows suitable pharmaceutically acceptable salts of metformin.

In the present invention, metformin can be administered according to commonly known administration protocols of metformin in accordance with the terms of marketing authorization. For example, metformin can be administrated once daily, twice daily or three times a day. In particular, the metformin dose applied prior to the onset of the therapy as disclosed herein is continued in combination with lixisenatide or/and a pharmaceutically acceptable salt thereof, as disclosed herein.

In the present invention, metformin may be administered orally. The skilled person knows formulations of metformin suitable for treatment of type 2 diabetes mellitus by oral administration. Metformin may be administered to a patient in need thereof, in an amount sufficient to induce a therapeutic effect. Metformin may be administered in a dose of at least 1.0 g/day or at least 1.5 g/day. Metformin may be administered in a dose of at the maximum of 2.0 g/day. The daily metformin dose can be divided into 2 or three separate doses. For oral administration, metformin may be formulated in a solid dosage form, such as a tablet or pill. Metformin may be formulated with suitable pharmaceutically acceptable carriers, adjuvants, or/and auxiliary substances.

In the present invention, lixisenatide or/and a pharmaceutically acceptable salt may be administered in an add-on therapy to administration of metformin.

In the present invention, the terms "add-on", "add-on treatment" and "add-on therapy" relate to treatment according to the present invention with an oral anti-diabetic, as described herein, in particular metformin, and lixisenatide. The oral anti-diabetic, in particular metformin, and lixisenatide each may be administered in a once-a-day-dosage. The oral anti-diabetic, in particular metformin, and lixisenatide may be administered by different administration routes. Metformin may be administered orally, and lixisenatide may be administered parenterally.

In particular, "add-on", "add-on treatment" and "add-on therapy" mean that the dose of the oral anti-diabetic, in particular metformin, administered prior to the onset of the treatment with lixisenatide or/and a pharmaceutically acceptable salt thereof, as disclosed herein, is continued in combination with lixisenatide or/and a pharmaceutically acceptable salt thereof.

In the present invention, lixisenatide includes pharmaceutically acceptable salts thereof. The person skilled in the art knows suitable pharmaceutically acceptable salts of lixisenatide. A preferred pharmaceutically acceptable salt of lixisenatide employed in the present invention is the acetate salt of lixisenatide.

In the present invention, lixisenatide or/and the pharmaceutically acceptable salt thereof may be administered to a patient in need thereof, in an amount sufficient to induce a therapeutic effect.

In the present invention, lixisenatide or/and the pharmaceutically acceptable salt thereof may be formulated with suitable pharmaceutically acceptable carriers, adjuvants, or/and auxiliary substances.

Lixisenatide or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. Lixisenatide or/and a pharmaceutically acceptable salt thereof may be administered in a suitable amount, for instance in an amount in the range of 5 µg to 10 µg per dose or 5 to 20 µg per dose.

In the present invention, lixisenatide or/and a pharmaceutically acceptable salt thereof may be administered in a daily dose in the range of 5 to 10 µg or 5 to 20 µg. Lixisenatide or/and a pharmaceutically acceptable salt thereof may be administered by one injection per day. Lixisenatide or/and a pharmaceutically acceptable salt thereof may be administered about 30 min or 1 hour before breakfast.

In the present invention, lixisenatide or/and a pharmaceutically acceptable salt thereof may be provided in a liquid composition, which preferably is an aqueous formulation. It is preferred that the liquid composition is suitable for parenteral administration, in particular for injection. The skilled person knows such liquid compositions of lixisenatide. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition comprising lixisenatide or/and a pharmaceutically acceptable salt thereof may comprise a suitable preservative. A suitable preservative may be selected from phenol, m-cresol, benzyl alcohol and p-hydroxybenzoic acid ester. A preferred preservative is m-cresol.

The liquid composition comprising lixisenatide or/and a pharmaceutically acceptable salt thereof may comprise a tonicity agent. A suitable tonicity agent may be selected from glycerol, lactose, sorbitol, mannitol, glucose, NaCl, calcium or magnesium containing compounds such as $CaCl_2$. The concentration of glycerol, lactose, sorbitol, mannitol and glucose may be in the range of 100-250 mM. The concentration of NaCl may be up to 150 mM. A preferred tonicity agent is glycerol.

The liquid composition comprising lixisenatide or/and a pharmaceutically acceptable salt thereof may comprise methionine from 0.5 µg/mL to 20 µg/mL, preferably from 1 µg/ml to 5 µg/ml. Preferably, the liquid composition comprises L-methionine.

Yet another aspect of the present invention is a method for the reduction of cardiovascular morbidity or/and cardiovascular mortality in a type 2 diabetes mellitus patient who experienced at least one acute coronary syndrome event, said method comprising administering lixisenatide or/and a pharmaceutically acceptable salt thereof, to the patient in need thereof. Cardiovascular morbidity, cardiovascular mortality and acute coronary syndrome event are defined as described herein. The patient is a type 2 diabetes mellitus patient as described herein.

A further aspect of the present invention is a method of treatment of the risk of cardiovascular death, non-fatal myocardial infarction, non-fatal stroke, unstable angina, hospitalization for unstable angina, non-fatal heart failure, hospitalization for heart failure or/and revascularization procedure in a type 2 diabetes mellitus patient, said method comprising administering lixisenatide or/and a pharmaceutically acceptable salt thereof, to the patient in need thereof. The patient is a type 2 diabetes mellitus patient as described herein.

A further aspect of the present invention is a method of treatment of the risk of cardiovascular death, non-fatal myocardial infarction, non-fatal stroke, unstable angina, or/and non-fatal heart failure in a type 2 diabetes mellitus patient, said method comprising administering lixisenatide or/and a pharmaceutically acceptable salt thereof, to the patient in need thereof. The patient is a type 2 diabetes mellitus patient as described herein.

A further aspect of the present invention is a method for the reduction of the blood plasma concentration of hs-CRP, BNP or/and NT-proBNP in a type 2 diabetes mellitus patient, said method comprising administering lixisenatide or/and a pharmaceutically acceptable salt thereof, to the patient in need thereof. The patient is a type 2 diabetes mellitus patient as described herein.

A further aspect of the present invention is a method for the reduction of urinary albumin excretion in a type 2 diabetes mellitus patient, said method comprising administering lixisenatide or/and a pharmaceutically acceptable salt thereof, to the patient in need thereof. The patient is a type 2 diabetes mellitus patient as described herein. In particular, the patient has experienced at least one acute coronary syndrome event. The at least one acute coronary syndrome event is the at least one acute coronary syndrome event as described herein. In particular, the patient may suffer from albuminuria or/and renal impairment, as described herein.

A further aspect of the present invention is a method for the reduction of progression of urinary albumin excretion in a type 2 diabetes mellitus patient, said method comprising administering lixisenatide or/and a pharmaceutically acceptable salt thereof, to the patient in need thereof. The patient is a type 2 diabetes mellitus patient as described herein. In particular, the patient has experienced at least one acute coronary syndrome event. The at least one acute coronary syndrome event is the at least one acute coronary syndrome event as described herein. In particular, the patient may suffer from albuminuria or/and renal impairment, as described herein.

A further aspect of the present invention is the use of lixisenatide or/and a pharmaceutically acceptable salt thereof, for the manufacture of a medicament for the reduction of cardiovascular morbidity or/and cardiovascular mortality in a type 2 diabetes mellitus patient who experienced at least one acute coronary syndrome event. Cardiovascular morbidity, cardiovascular mortality and acute coronary syndrome event are defined as described herein. The patient is a type 2 diabetes mellitus patient as described herein. In particular, the patient may suffer from albuminuria or/and renal impairment, as described herein.

Another aspect of the present invention is the use of lixisenatide or/and a pharmaceutically acceptable salt thereof, for the manufacture of a medicament for the treatment of the risk of cardiovascular death, non-fatal myocardial infarction, non-fatal stroke, unstable angina, hospitalization for unstable angina, non-fatal heart failure, hospitalization for heart failure or/and revascularization procedure in a type 2 diabetes mellitus patient. The patient is a type 2 diabetes mellitus patient as described herein.

Another aspect of the present invention is the use of lixisenatide or/and a pharmaceutically acceptable salt thereof, for the manufacture of a medicament for the treatment of the risk of cardiovascular death, non-fatal myocardial infarction, non-fatal stroke, unstable angina, or/and non-fatal heart failure in a type 2 diabetes mellitus patient. The patient is a type 2 diabetes mellitus patient as described herein.

Another aspect of the present invention is the use of lixisenatide or/and a pharmaceutically acceptable salt thereof, for the manufacture of a medicament for the reduction of the blood plasma concentration of hs-CRP, BNP or/and NT-proBNP in a type 2 diabetes mellitus patient. The patient is a type 2 diabetes mellitus patient as described herein.

A further aspect of the present invention is the use of lixisenatide or/and a pharmaceutically acceptable salt thereof, for the manufacture of a medicament for the reduction of urinary albumin excretion in a type 2 diabetes mellitus patient. The patient is a type 2 diabetes mellitus patient as described herein. In particular, the patient has experienced at least one acute coronary syndrome event. The at least one acute coronary syndrome event is at least one acute coronary syndrome event as described herein. In particular, the patient may suffer from albuminuria or/and renal impairment, as described herein.

A further aspect of the present invention is the use of lixisenatide or/and a pharmaceutically acceptable salt thereof, for the manufacture of a medicament for the reduction of progression of urinary albumin excretion in a type 2 diabetes mellitus patient. The patient is a type 2 diabetes mellitus patient as described herein. In particular, the patient has experienced at least one acute coronary syndrome event. The at least one acute coronary syndrome event is at least one acute coronary syndrome event as described herein. In particular, the patient may suffer from albuminuria or/and renal impairment, as described herein.

REFERENCES

1 Zimmet P, Alberti K G, Shaw J. Global and societal implications of the diabetes epidemic. Nature 2001; 414: 782-87.
2 King H, Aubert R E, Herman W H. Global burden of diabetes, 1995-2025. Prevalence, numerical estimates and projections. Diabetes Care 1998; 21: 1414-31.
3 Williams G, Pickup J C. Macrovascular disease in Diabetes. In handbook of Diabetes. 2nd ed. Williams G, Pickup J C, Eds. Oxford, U K, Blackwell Science 1999; 151-58,
4 Khaw K-T, Wareham N, Luben R, et al. Glycated haemoglobin, diabetes, and mortality in men in Norfolk cohort of European Prospective Investigation of cancer and Nutrition (EPICNorfolk). BMJ 2001; 322: 15-18.
5 The Diabetes Control and Complications Trial Research Group. The effect of intensive treatment of diabetes on the development and progression of long-term complications in insulin-dependent diabetes mellitus. N Engl J Med 1993; 329: 977-86.
6 The UK Prospective Diabetes Study (UKPDS) Group. Effect of intensive blood-glucose control with metformin on complications in overweight patients with type 2 diabetes (UKPDS 34). Lancet 1998; 352: 854-65.
7 The UK Prospective Diabetes Study (UKPDS) Group. Intensive blood-glucose control with sulphonylureas or insulin compared with conventional treatment and risk of complications in patients with type 2 diabetes (UKPDS 33). Lancet 1998; 352: 837-53.
8 Nathan D M, Buse J B, Davidson M B, Ferrannini E, Holman R R, Sherwin R, Zinman B: Medical Management of Hyperglycemia in type 2 diabetes: a consensus algorithm for the initiation and adjustment of therapy. Diabetes Care 2009; 32: 193-203.
9 Diabetes Control and Complications Trial/Epidemiology of Diabetes Interventions and Complications Research Group: Intensive diabetes therapy and carotid intima-media thickness in type 1 diabetes. N Engl J Med 2003; 348: 2294-303.
11 Diabetes Control and Complications Trial/Epidemiology of Diabetes Interventions and Complications Research Group: Intensive diabetes treatment and cardiovascular disease in patients with type 1 diabetes. N Engl J Med 2005; 353: 2643-5.
11 The Action to Control Cardiovascular Risk in Diabetes Study Group: Effects of intensive glucose lowering in type 2 diabetes. N Engl J Med 2008; 358: 2545-59.
12 The ADVANCE Collaborative Group: Intensive blood glucose control and vascular outcomes in patients with type 2 diabetes. N Engl J Med 2008; 358: 2560-72.
13 Abraira C, Duckworth W C. Moritz T: Glycaemic separation and risk factor control in the Veterans Affairs Diabetes Trial: an interim report. Diabetes Obes Metab 2009; 11 (2): 150-56. Epub 2008 Jul. 29.
14 Ray K K, Seshasai S R. Wijesunya S, Sivakumaran R, Nethercott S, Preiss D et al. Effect of intensive control of glucose on cardiovascular outcomes and death in patients with diabetes mellitus: a meta-analysis of randomized controlled trials. Lancet 2009; 373: 1765-72.

15 Kelly T N, Bazzano L A, Fonseca V A, Thethi T K, Reynolds K, He J. Systematic review: glucose control and cardiovascular disease in type 2 diabetes. Ann Intern Med 2009; 151: 394-403.

17 Drucker D J, Nauck M A. The incretin system: glucagon-like peptide-1 receptor agonists and dipeptidyl peptidase-4 inhibitors in type 2 diabetes. The Lancet 2006; 368: 1696-705.

18 Weir G C. Glucagon-like peptide-1 (7-37) actions on endocrine pancreas. Diabetes 1989; 38:338-42.

19 Park C W, Kim H W, Ko S H, Lim J H, Ryu G R, Chung H W, Han S W, Shin S J, Bang B K, Breyer M D, Chang Y S. J Am Soc Nephrol 2007; 18(4): 1227-38.

20 Das R, Kilcullen N, Morell C, Robinson M B, Barth J H, Hall A S. The British Cardiac Society Working group definition of myocardial infarction: implications for practice. Heart 2006; 92(1): 21-6.

21 Beckman J A, Creager M A, Libby P. Diabetes and atherosclerosis: epidemiology, pathophysiology, and management. JAMA 2002; 287: 2570-81.

22 Cannon C P, Braunwald E, McCabe C H, Rader D J, Rouleau J L, Belder R. Joyal S V, Hill K A, Pfeffer M A, and Skene A M, for the Pravastatin or Atorvastatin Evaluation and Infection Therapy-Thrombolysis in Myocardial Infarction Investigators*. Intensive versus Moderate Lipid Lowering with Statins after Acute Coronary Syndromes. N Engl J Med 2004; 350(15):1495-504.

23 De Lemos J A, Blazing M A, Wiviott S D, Lewis E F, Fox K A, White H D, Rouleau J L, Pedersen T R, Gardner L H, Mukherjee R, Ramsey K E, Palmisano J, Bilheimer D W, Pfeffer M A, Califf R M, Braunwald E, A to Z Investigators. Early intensive vs. a delayed conservative simvastatin strategy in patients with acute coronary syndromes: phase Z of the A to Z trial. JAMA 2004; 292: 1307-16.

24 Wiviott S D., Braunwald E, Angiolillo D J, Meisel S, Dalby A J, Verheugt F W A, Goodman S G, Corbalan R, Purdy D A, Murphy S A, McCabe C H, Antman E M; for the TRITON-TIMI 38 Investigators. Greater Clinical Benefit of More Intensive Oral Antiplatelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38. Circulation 2008; 118: 1626-36.

25 Yusuf S, Zhao F, Mehta S R, Chrolavicius S, Tognoni G, Fox K K. Clopidogrel in Unstable Angina to Prevent Recurrent Events Trial Investigators. Effects of clopidogrel in addition to aspirin in patients with acute coronary syndromes without ST-segment elevation. N Engl J Med 2001; 345 (7): 494-502. Erratum in: N Engl J Med 2001 Dec. 6; 345(23):1716. N Engl J Med 2001 Nov. 15; 345(20): 1506.

26 Dinneen S F, Gerstein H C. The association of microalbuminuria and mortality in non-insulindependent diabetes mellitus. A systematic overview of the literature. Arch Intern Med 1997; 157: 1413-8.

27 Gerstein H C, Mann J F, Yi Q, Zinman B, Dinneen S F, Hoogwerf B, Halle J P, Young J, Rashkow A, Joyce C, Nawaz S, Yusuf S, the HOPE Study Investigators. Albuminuria and risk of cardiovascular events, death, and heart failure in diabetic and nondiabetic individuals. JAMA 2001; 286: 421-6.

28 Forman J P, Fisher N D, Schopick E L, Curhan G C. Higher levels of albuminuria within the normal range predict incident hypertension. J Am Soc Nephrol 2008; 19: 1983-8.

29 The UK Prospective Diabetes Study (UKPDS) Group. Tight blood pressure control and risk of macrovascular and microvascular complications in type 2 diabetes (UKPDS 38). BMJ 1998; 317: 703-13.

30 Zoungas S, De Galan B E, Ninomiya T, Grobbee D, Hamet P, Heller S, MacMahon S, Marre M, Neal B, Patel A, Woodward M, Chalmers J, on behalf of the ADVANCE collaborative group*. Combined Effects of Routine Blood Pressure Lowering and Intensive Glucose Control on Macrovascular and Microvascular Outcomes in Patients With Type 2 Diabetes. New results from the ADVANCE trial. Diabetes Care 2009; 32: 2068-74.

31 European Medicines Agency, Committee for Proprietary Medicinal Products (CPMP) and International Conference on Harmonisation of Technical Requirements for Registration of Pharmaceuticals for Human Use (ICH): ICH Topic M3 (R2)/Note for guidance on non-clinical safety studies for the conduct of human clinical trials and marketing authorization for pharmaceuticals (CPMP/ICH/286/95), 2009.

32 Standardized Definitions for Cardiovascular Outcomes Trials: Draft Recommendations. Division of Metabolism and Endocrinology Products. Center for Drug Evaluation and Research (CDER). Jul. 22, 2009.

33 Spertus J A, Winder J A, Dewhurst T A, Deyo R A, Fihn S D. Monitoring the quality of life in patients with coronary heart disease. Am J Cardiol. 1994; 74:1240-1244.

34 Spertus J A, Winder J A, Dewhurst T A, Deyo R A, Prodzinski J, McDonell M, Fihn S D. Development and evaluation of the Seattle Anginal Questionnaire: a new functional status measure for coronary artery disease. J Am Coil Cardiol. 1995; 25:333-341.

Spertus J A, Jones P, McDonell M, Fan V, Fihn S D. Health status predicts long-term outcome in outpatients with coronary disease. Circulation. 2002; 106:43-49.

36 Brazier J, Jones N, Kind P. Testing the validity of the Euroqol and comparing it with the SF-36 health survey questionnaire. Qual Life Res 1993; 2(3):169-180.

37 Nowels D, McGloin J, Westfall J M, Holcomb S. Validation of the EQ-5D quality of life instrument in patients after myocardial infarction. Qual Life Res 2005; 14(1):95-105.

38 EuroQol—a new facility for the measurement of health-related quality of life. The EuroQol Group. Health policy (Amsterdam, Netherlands) 1990: 16(3):199-208.

39 Dolan P. Modeling valuations for EuroQol health states. Med Care 1997; 35(11):1095-1108.

40 Shaw J W, Johnson J A, Coons S J. U S valuation of the EQ-5D health states: development and testing of the D1 valuation model. Med Care 2005; 43(3):203-220.

41 Juniper E F, Guyatt G H, Willan A, Griffith L E. Determining a minimal important change in a disease-specific quality of life questionnaire. J Clin Epidemiol 1994; 47:81-7.

42 K. Meadows, N. Steen, E. McColl, M. Eccles, C. Shiels, J. Hewison, et al., The diabetes health profile (DHP): a new instrument for assessing the psychosocial profile of insulin requiring patients: development and psychometric evaluation, Qual. Life Res. 5 (1996) 242-254.

43 K. A. Meadows, C. Abrams, A. Sandbaek, Adaptation of the diabetes health profile (DHP-1) for use with patients with Type 2 diabetes mellitus: psychometric evaluation and cross-cultural comparison, Diabet. Med. 17 (2000) 572-580.

The invention is further illustrated be the following example and figures:

FIGURE LEGENDS

FIG. 1—Kaplan-Meier cumulative curves of the primary CV endpoint (time to the first occurrence of the composite of CV death, non-fatal MI, non-fatal stroke, or hospitalization for unstable angina)—ITT population. Only CAC positively adjudicated events are included.

Figure 2:
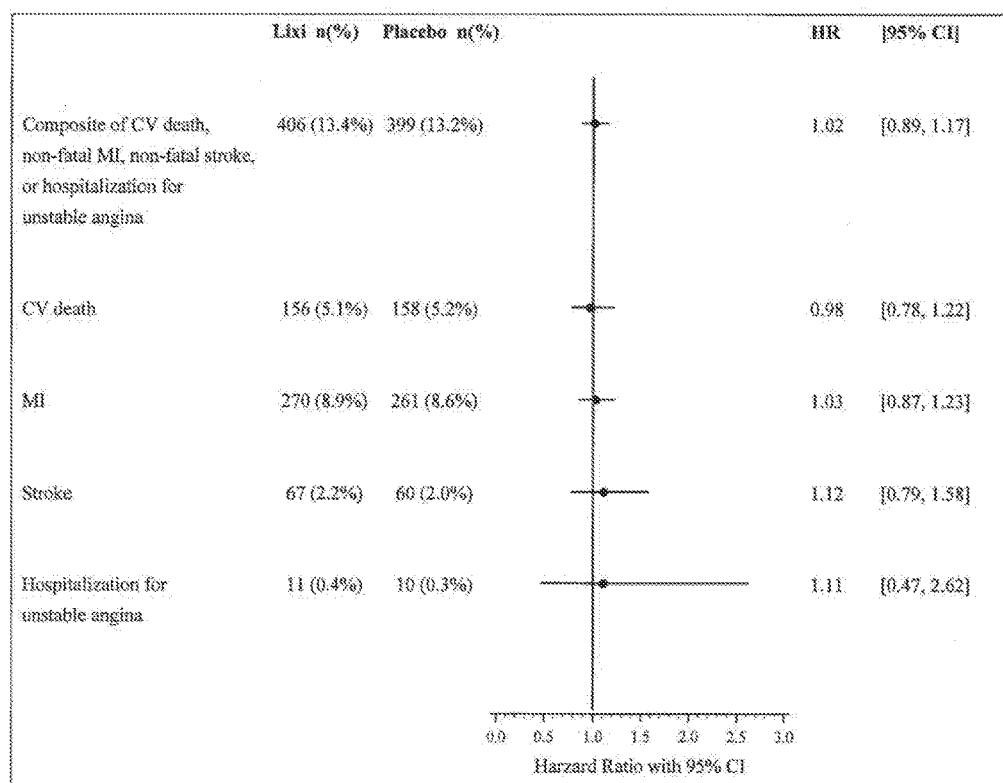

FIG. 2—Forest plot: analyses of each individual cardiovascular event of the primary endpoint—ITT population. CV: cardiovascular, MI: myocardial infarction, HR: hazard ratio, CI: confidence interval. Only CAC positively adjudicated events are included.

Figure 3:
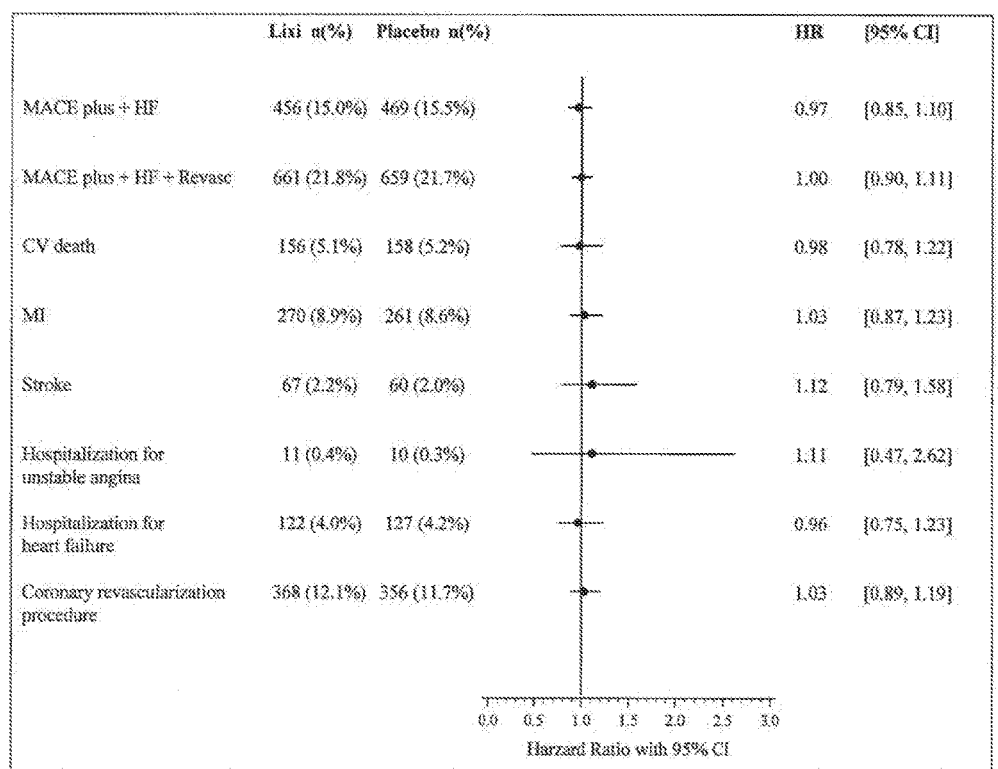

FIG. 3—Forest plot analyses of each individual cardiovascular event of the secondary endpoints—ITT population. MACE plus: Composite of CV death, non-fatal MI, non-fatal stroke, hospitalization for unstable angina. CV: cardiovascular, MI: myocardial infarction, HR: hazard ratio, CI: confidence interval. Only CAC positively adjudicated events are included.

FIG. 4—Plot of mean HbA1c (%) by scheduled visit—ITT population. SC: Screening, BL: Baseline. Only visits with at least 30 patients with measurements in each group are presented.

EXAMPLE

A Randomized, Double-Blind, Placebo-Controlled, Parallel-Group, Multicenter Study to Evaluate Cardiovascular Outcomes During Treatment with Lixisenatide in Type 2 Diabetic Patients after an Acute Coronary Syndrome Event

1 Abbreviations

ACS: acute coronary syndrome
AE: adverse event
ANCOVA: analysis of covariance
BMI: body mass index
CAC: Cardiovascular Events Adjudication Committee
CI: confidence interval
CV: cardiovascular
EOS: End of Study
GFR: glomerular filtration rate
MACE: major cardiovascular adverse event
MI: myocardial infarction
PSAC: Pancreatic Safety Assessment Committee
QD: once daily
T2DM: type 2 diabetes mellitus
TEAE: treatment-emergent AE
UACR: urinary albumin/creatinine ratio

2 Synopsis

Title of the study: A randomized, double-blind, placebo-controlled, parallel-group, multicenter study to evaluate cardiovascular outcomes during treatment with lixisenatide in type 2 diabetic patients after an Acute Coronary Syndrome event
Study centers: multicenter: 888 in 49 countries
Phase of development: Phase 3
Objectives:
Primary objective: To demonstrate that lixisenatide can reduce cardiovascular (CV) morbidity and mortality (composite endpoint of CV death, non-fatal myocardial infarction [MI], non-fatal stroke, hospitalization for unstable angina) compared to placebo in type 2 diabetic patients who recently experienced a spontaneous, biomarker-positive acute coronary syndrome (ACS) event
Methodology: Double-blind, placebo-controlled, 1:1 randomized, 2-arm, parallel-group, multinational, Phase 3 study conducted in adult patients with type 2 diabetes mellitus (T2DM).

| Number of patients: | Planned 6000 |
|---|---|
| | Randomized: 6068 |
| | Treated: 6063 |
| Evaluated: | Efficacy: 6068 |
| | Safety: 6063 |

Diagnosis and criteria for inclusion:
Patients with a history of T2DM as per World Health Organization criteria who had experienced a biomarker-proven spontaneous ACS event of ST-segment elevation myocardial infarction or non-ST-segment elevation myocardial infarction or unstable angina within 180 days prior to screening.
Study treatment Investigational medicinal product: AVE0010/lixisenatide
Formulations:
Control Drug: Volume-matched placebo, 3-mL aqueous solution (in cartridge)
Active drug: 3-mL aqueous solution (in cartridge) containing 300 µg of active ingredient (ie, 100 µg/mL), glycerol, sodium acetate trihydrate, methionine, meta-cresol, HCL/NaOH, water for injection
Route of administration: subcutaneous injection
Dose regimen: The starting dose was 10 µg once daily (QD) for 2 weeks; the dose was then increased to the maintenance dose of 20 µg QD for the remainder of the treatment period, safety and tolerability permitting. The IMP dose could be down-titrated to 15 µg or 10 µg QD if the patient was intolerant of 20 µg or 15 µg QD. The IMP was administered in the morning within 1 hour prior to breakfast. However, if a patient experienced an adverse event (eg, nausea or vomiting) or other conditions that made the morning dosing difficult, the Investigator could change the dosing time to the evening (within 1 hour prior to dinner).
Non-investigational medicinal products: No background antidiabetic medications were specified in the study protocol. Patients were eligible for enrollment regardless of whether or not they were receiving pharmacologic therapy for diabetes treatment. During the double-blind treatment period, the management of glycemia was left to the Investigator's judgment in accordance with clinical guidelines. The Investigators were allowed to undertake appropriate action, ie, adjust the background antidiabetic treatment or prescribe an additional antidiabetic medication according to its labeling. Exceptions were other GLP-1 receptor agonists or DPP-IV inhibitors, which were prohibited throughout the study.
Duration of treatment: At least 10 months for the last randomized patients with variable treatment periods for all study patients until 844 patients had at least one positively-adjudicated primary CV event.

-continued

Duration of observation: A minimum of 10 months + 2 weeks (7 + 3 days run-in + variable double-blind treatment + 3 days post treatment follow-up)
Criteria for evaluation:

Efficacy
Primary Endpoint: Time to the first occurrence of any of the following events positively adjudicated by the Cardiovascular Events Adjudication Committee (CAC): Cardiovascular death, non-fatal MI, non-fatal stroke, or hospitalization for unstable angina
Secondary Endpoints:
Time to the first occurrence of any of the following events positively adjudicated by the CAC: Cardiovascular death, non-fatal MI, non-fatal stroke, hospitalization for unstable angina, or hospitalization for heart failure
Time to the first occurrence of any of the following events positively adjudicated by the CAC: Cardiovascular death, non-fatal MI, non-fatal stroke, hospitalization for unstable angina, hospitalization for heart failure, or coronary revascularization procedure
Percent change in the urinary albumin/creatinine ratio from baseline to Week 108 (ie, approximately 2 years)
Safety
Safety analyses included adverse events (AE), serious AEs, vital signs, and standard hematology and blood chemistry laboratory values.
Statistical methods:

Analysis of efficacy endpoints
All efficacy analyses were performed on the ITT population, defined as all randomized patients analyzed according to the treatment group allocated at randomization, regardless of treatment discontinuation. The analyses of CV efficacy endpoints were based on the positively-adjudicated CV endpoint events occurring from randomization to the study end date inclusive, even for patients who had discontinued study treatment.
The time to the first occurrence of the primary CV endpoint event was analyzed using a Cox proportional hazards model with treatment (lixisenatide, placebo), and region (North America, South and Central America, Western Europe, Eastern Europe, Africa/Near East, and Asia/Pacific) as the factors. The hazard ratio between lixisenatide and placebo was estimated along with the associated 2-sided 95% confidence interval (CI). Depending on the upper bound of the 2-sided 95% CI from the above Cox model: (1) non-inferiority to confirm an acceptable CV safety profile of lixisenatide was to be claimed if the upper bound of the 2-sided 95% CI of the hazard ratio was less than 1.3; and (2) superiority of lixisenatide versus placebo was to be claimed if the upper bound of the 2-sided 95% CI of the hazard ratio was less than 1.0. The p-value using the log-rank test was also calculated for descriptive purpose.
The two secondary composite CV endpoints were analyzed using the same Cox proportional hazards model as described for the primary efficacy endpoint. The time to the first occurrence of any major adverse cardiovascular event (MACE) (ie, cardiovascular death, non-fatal MI, or non-fatal stroke) was performed using the same Cox model as described for the analysis of the primary CV endpoint.
Percent change in the urinary albumin/creatinine ratio (UACR) from baseline to Week 108, was analyzed in the ITT population using an analysis of covariance (ANCOVA) model with treatment (lixisenatide, placebo), region, intake of ACE inhibitors at baseline (yes or no) and intake of angiotensin II receptor blockers at baseline (yes or no) as fixed effects and using the baseline urinary albumin/creatinine ratio as a covariate.
Analysis of safety endpoints
All safety analyses were performed on the safety population (ie, all randomized patients who received at least one dose of double-blind IMP) during the on-treatment period, which was defined as the time from the first administration of double-blind IMP up to 3 days after the last administration of double-blind IMP. The safety endpoints included AEs, clinical laboratory data, and vital signs. The events reported in the specific CV AE forms for "Myocardial infarction or hospitalization for unstable angina", "Stroke", "Hospitalization for heart failure", or "Coronary revascularization procedure" were not included in the safety analyses, regardless of adjudication results, seriousness, or relationship to IMP, because they were analyzed as efficacy endpoints.
Suspected events of pancreatitis reported during the on-treatment period and pancreatic neoplasms reported during the on-treatment and post-treatment periods were summarized based on the adjudicated outcome. The number (%) of patients with overall malignancy and subcategories of major cancer types (thyroid, lung, colorectal, breast, and prostate) during the combined on-treatment and post-treatment periods were summarized.
Summary:
Population characteristics:
The demographics were well-balanced between the two treatment groups. The mean age of the ITT population was 60 years and more male (69%) and Caucasian (75%) patients were enrolled. The majority of patients were either obese or overweight (median BMI 29.4 kg/m$^2$). Baseline diabetes status (duration of diabetes, HbA1c, and incidence of diabetic complications) was generally similar between the treatment groups. The characteristics of the qualifying ACS were well-matched between the treatment groups, with most patients (72%) having had a qualifying ACS within 90 days prior to randomization. The most common type of qualifying ACS was ST-segment elevation MI (44%); about 60% of patients in both groups underwent percutaneous coronary revascularization.
All 6068 randomized and treated patients were included for efficacy and safety analyses, respectively. Of these, 5853 patients completed the study, defined as patients who either performed the final study visit at the protocol-specified End of Study (EOS) or died during the study period. The median IMP exposure was 22.4 and 23.3 months for lixisenatide and placebo, respectively. At the time of the EOS, vital status was available for 98.8% of patients.

|  | Placebo (N = 3034) | Lixisenatide (N = 3034) |
|---|---|---|
| Randomized and treated | 3032 (>99.9%) | 3031 (>99.9%) |
| Completed the study | 2924 (96.4%) | 2929 (96.5%) |
| Completed the double blind treatment | 2264 (74.6%) | 2147 (70.8%) |
| Vital status known at the end of study | 2992 (98.6%) | 3005 (99.0%) |
| Alive | 2769 (91.3%) | 2794 (92.1%) |
| Dead | 223 (7.4%) | 211 (7.0%) |
| LTFU | 14 (0.5%) | 11 (0.4%) |

LTFU: patients discontinued study participation without a known reason and were not reachable via any means of contact by the Investigator
until the EOS.

Efficacy Results:

Primary CV endpoint:
The hazard ratio for lixisenatide versus placebo was 1.017 with an associated 2-sided 95% CI of 0.886 to 1.168. The upper bound of the 2-sided 95% CI estimated from the Cox model was below the pre-specified non-inferiority margin of 1.3 and above the superiority margin of 1.0.
The percentage of patients with a primary CV endpoint event (13.4% and 13.2% for lixisenatide and placebo, respectively) as well as the incidence per 100-patient years (6.39 and 6.31 for lixisenatide and placebo, respectively) were comparable between treatment groups.
Kaplan-Meier cumulative curves of time from randomization to the first primary CV endpoint event for lixisenatide and placebo were superimposed over the majority of the study period (FIG. 1).
Results of the individual components of the composite endpoint were consistent with the analyses of the primary composite endpoint (Table 7).
Results of the analysis of MACE (CV death, non-fatal MI, and non-fatal stroke) (HR 1.02, 95% CI of 0.887 to 1.172) were consistent with the results of the primary composite endpoint (MACE + hospitalization for unstable angina).
Secondary CV endpoints: Similarly, the incidence rates were comparable between the two treatments for both of the secondary composite CV endpoints.
The hazard ratio of the composite endpoint of CV death, nonfatal MI, nonfatal stroke, hospitalization for unstable angina, or hospitalization for heart failure was 0.968 for lixisenatide versus placebo with an associated 2-sided 95% CI of 0.851 to 1.102.
The hazard ratio of the composite endpoint of CV death, nonfatal MI, nonfatal stroke, hospitalization for unstable angina, hospitalization for heart failure, or coronary revascularization was 0.997 for lixisenatide versus placebo with an associated 2-sided 95% CI of 0.895 to 1.111.
The results for the individual components of the composite endpoints were consistent with analyses of the secondary composite endpoints (FIG. 3).
Urinary albumin/creatinine ratio: Geometric mean urinary albumin/creatinine ratio (UACR) increased from baseline to Week 108 in both treatment groups (24% and 34% change from baseline for the lixisenatide and placebo groups, respectively), but showed a smaller increase in the lixisenatide group as compared to the placebo group (the difference between lixisenatide versus placebo in the percent change from baseline of UACR was −0.10% with 95% CI: −0.17, −0.03).
Safety results:
Safety endpoints were generally comparable between the two treatments:
The proportion of patients with at least 1 treatment-emergent AE (TEAE) was numerically higher in the lixisenatide (80.7%) versus the placebo group (76.6%).
More patients in the lixisenatide than in the placebo group had a TEAE leading to IMP discontinuation (11.4% and 7.2%, respectively). The imbalance was mainly due to the higher frequency of TEAEs of nausea and vomiting, known side effects of GLP-1 receptor agonist treatment.
Serious TEAEs were reported in 20.6% of patients in the lixisenatide and 22.1% in the placebo group. The frequencies were generally similar between treatments or numerically lower in the lixisenatide group compare to the placebo group with the exception of serious TEAEs categorized as gallbladder disorders (32 patients [1.1%] versus 19 [0.6%]), including cholecystitis (acute or chronic) and cholelithiasis.
The incidence of all deaths (CV-death, non-CV death, or unknown death) was comparable between lixisenatide and placebo during the on-treatment (3.1% and 3.2%) and on-study (7.0% and 7.4%) periods. The incidences of CV deaths and non-CV deaths were also similar in the two treatment groups.
The incidence of pancreatitis and pancreatic cancer as adjudicated by a blinded Pancreatic Safety Assessment Committee (PSAC) was lower with lixisenatide treatment than with placebo (5 patients [0.2%] versus 8 [0.3%] and 3 [<0.1%] versus 9 [0.3%] for pancreatitis and pancreatic cancer, respectively).
Patients in the lixisenatide group had a lower rate of severe symptomatic hypoglycemia (16 versus 37 events [0.3 versus 0.6 per 100-patient years]) while maintaining better glycemic control as compared to the patients in the placebo group.
Conclusions:
The ELIXA study evaluated the CV effects of long-term administration of lixisenatide compared to placebo in patients with T2DM and a recent ACS; the results demonstrated the long-term CV safety of lixisenatide. Furthermore, lixisenatide was generally safe and well-tolerated; no unexpected safety concerns were identified.
Demographics and disease characteristics were well matched between the two treatment groups
More than 96% of the patients in both treatment groups completed the study and vital status at the end of the study was known for >98% of the patients in both treatment groups
In the ELIXA study, lixisenatide administered for a median duration of 22.4 months to patients with T2DM and a high CV risk:
Met the pre-specified criterion of non-inferiority versus placebo for the composite primary endpoint of CV death, non-fatal myocardial infarction, non-fatal stroke, or hospitalization for unstable angina.
Did not demonstrate superiority over placebo in reducing the composite primary CV endpoint
Showed a consistent neutral effect on the individual components of the composite primary and secondary CV endpoints, including hospitalization for heart failure
Appeared to decrease the worsening of albuminuria
Was associated with:
No increased risk of pancreatitis
No increased risk of pancreatic neoplasm
No increased risk of severe, symptomatic hypoglycemia

3 Results

3.1 Study Patients

3.1.1 Patient Accountability

A total of 7719 patients were screened from 888 study centers in 49 countries worldwide; of these, 6068 patients were randomized 1:1 to double-blind treatment with IMP: 3034 to placebo, 3034 to lixisenatide. One additional patient was randomized, but did not sign the Health Insurance Portability and Accountability Act form, and hence was not included in the 6068 patients in the ITT population.

Five of the randomized patients (2 in the placebo and 3 in the lixisenatide groups) did not receive IMP but were included in the analyses of the ITT population.

3.1.2 Study Disposition

Patient disposition by treatment group is provided in Table 1. The number of patients in "Complete the study" included those who either performed the End of Study visit as defined in the protocol or died during the study period. At the End of Study, vital status was not obtained for 71 patients (42 [1.4%] for placebo and 29 [1.0%] for lixisenatide), including patients from sites that had been terminated by the Sponsor, patients lost to follow-up, and patients who withdrew prematurely from the study and refused further contact with the investigators.

Numerically more patients treated with lixisenatide prematurely discontinued study treatment as compared to patients treated with placebo. The most common reasons for treatment discontinuation were "Adverse events" and "Withdrawal by patient" in both groups.

The study discontinuation rate was comparable between treatment groups; the main reason for study discontinuation was "withdrawal by patients".

TABLE 1

Patient disposition with reason for premature discontinuation - Randomized population

|  | Placebo (N = 3034) | Lixisenatide (N = 3034) |
|---|---|---|
| Randomized and not treated | 2 (<0.1%) | 3 (<0.1%) |
| Randomized and tested | 3032 (>99.9%) | 3031 (>99.9%) |
| Complete the study | 2924 (96.4%) | 2929 (96.5%) |
|   Complete the final visit | 2702 (89.1%) | 2722 (89.7%) |
|   Death | 222 (7.3%) | 207 (6.8%) |
| Vital states known at the global study end | 2992 (98.6%) | 3005 (99.0%) |
|   Alive | 2769 (91.3%) | 2794 (92.1%) |
|   Dead | 223 (7.4%) | 211 (7.0%) |
| Did not complete treatment | 768 (25.3%) | 884 (29.1%) |
|   Adverse event | 310 (10.2%) | 418 (13.8%) |
|   Site termination by sponsor | 8 (0.3%) | 4 (0.1%) |
|   Withdrawal by patient | 398 (13.1%) | 414 (13.6%) |
|     Unwilling to undergo injections | 119 (3.9%) | 116 (3.8%) |
|     Unwilling or unable to perform study procedure | 82 (2.7%) | 83 (2.7%) |
|     Personal or family issue | 127 (4.2%) | 137 (4.5%) |
|     Unwilling or unable to attend study visits or to be contacted | 70 (2.3%) | 78 (2.6%) |
|   Physician's decision, due to potential risk of continued IMP administration | 16 (0.5%) | 24 (0.8%) |
|   Protocol deviation | 15 (0.5%) | 10 (0.3%) |
|   Other | 21 (0.7%) | 14 (0.5%) |
| Did not complete the study | 110 (3.6%) | 105 (3.5%) |
|   Site termination by sponsor | 13 (0.4%) | 5 (0.2%) |
|   Withdrawal by patient | 83 (2.7%) | 88 (2.9%) |
|     Personal or family issue | 21 (0.7%) | 12 (0.4%) |
|     Due to an adverse event | 2 (<0.1%) | 5 (0.2%) |
|     Unwilling or unable to attend study visits or to be contacted | 60 (2.0%) | 71 (2.3%) |
|   Patient lost to follow-up | 14 (0.5%) | 11 (0.4%) |
|   Other | 0 | 1 (<0.1%) |

IMP: investigational medicinal product
Note:
Percentages are calculated using the number of randomized patients as denominator.

3.1.3 Demographics and Baseline Characteristics

Demographics were well-balanced between the two treatment groups (Table 2).

Median age was 60 years and about one quarter of the study population was 65 years or older. More male and Caucasian patients were enrolled in the study. The majority of patients were either obese or overweight with a median body mass index (BMI) of 29.4 kg/m².

TABLE 2

Demographics and patient characteristics at screening or baseline - Randomized population

|  | Placebo (N = 3034) | Lixisenatide (N = 3034) | All (N = 6068) |
|---|---|---|---|
| Age (years) | | | |
| Number | 3034 | 3034 | 6068 |
| Mean (SD) | 60.6 (9.6) | 59.9 (9.7) | 60.3 (9.7) |
| Medians | 61.0 | 60.0 | 60.0 |
| Min:Max | 30:89 | 30:93 | 30:93 |
| Age group (years) [n (%)] | | | |
| Number | 3034 | 3034 | 6068 |
| <50 | 377 (12.4%) | 464 (15.3%) | 841 (13.9%) |
| ≥50 to <65 | 1617 (53.3%) | 1567 (51.6%) | 3184 (52.5%) |
| ≥65 to <75 | 792 (26.1%) | 805 (26.5%) | 1597 (26.3%) |
| ≥75 | 248 (8.2%) | 198 (6.5%) | 446 (7.4%) |
| Gender [n (%)] | | | |
| Number | 3034 | 3034 | 6068 |
| Male | 2096 (69.1%) | 2111 (69.6%) | 4207 (69.3%) |
| Female | 938 (30.9%) | 923 (30.4%) | 1861 (30.7%) |
| Race [n (%)] | | | |
| Number | 3034 | 3034 | 6068 |
| Caucasian/White | 2318 (76.4%) | 2258 (74.4%) | 4576 (75.4%) |
| Black | 103 (3.4%) | 118 (3.9%) | 221 (3.6%) |
| Asian/Oriental | 367 (12.1%) | 404 (13.3%) | 771 (12.7%) |
| Other | 246 (8.1%) | 254 (8.4%) | 500 (8.2%) |
| Ethinicity [n (%)] | | | |
| Number | 3034 | 3034 | 6068 |
| Hispanic | 903 (29.8%) | 865 (28.5%) | 1768 (29.1%) |
| Not hispanic | 2131 (70.2%) | 2169 (71.5%) | 4300 (70.9%) |
| Baseline body weight (kg) | | | |
| Number | 3032 | 3033 | 6065 |
| Mean (SD) | 85.06 (19.64) | 84.64 (19.21) | 84.85 (19.43) |
| Median | 82.40 | 82.40 | 82.40 |
| Min:Max | 38.0:198.2 | 40.2:232.0 | 38.0:232.0 |
| Baseline BMI (kg/m²) | | | |
| Number | 3032 | 3033 | 6065 |
| Mean (SD) | 30.20 (5.79) | 30.12 (5.60) | 30.16 (5.69) |
| Median | 29.29 | 29.40 | 29.35 |
| Min:Max | 16.9:59.3 | 17.1:68.9 | 16.9:68.9 |
| Baseline BMI Categories (kg/m²) [n (%)] | | | |
| Number | 3032 | 3033 | 6065 |
| <30 | 1681 (55.4%) | 1649 (54.4%) | 3330 (54.9%) |
| ≥30 | 1351 (44.6%) | 1384 (45.6%) | 2735 (45.1%) |

SD: standard deviation, BMI: body mass index.

Diabetes characteristics at screening or baseline were generally well-matched between treatment groups (Table 3. Around 40% of patients in both groups had long-standing T2DM (10 years). Glycemia at study entry as represented by HbA1c and FPG was relatively controlled and was balanced between treatment groups. Over 75% of patients had impaired renal function and more than 20% of patients had an estimated glomerular filtration rate (GFR)<60 mL/min/1.73 m². At screening, ~25% of patients in both treatment groups had microalbuminuria or overt proteinuria.

TABLE 3

Disease characteristics at screening or baseline: Diabetes status - Randomized population

| | Placebo (N = 3034) | Lixisenatide (N = 3034) | All (N = 6068) |
|---|---|---|---|
| Duration of diabetes (years) | | | |
| Number | 3034 | 3031 | 6065 |
| Mean (SD) | 9.38 (8.32) | 9.20 (8.19) | 9.29 (8.25) |
| Median | 7.36 | 7.40 | 7.38 |
| Min:Max | 0.0:54.7 | 0.0:50.0 | 0.0:54.7 |
| Duration of diabetes (years) | | | |
| Number | 3034 | 3031 | 6065 |
| <10 | 1789 (59.0%) | 1828 (60.3%) | 3617 (59.6%) |
| ≥10 | 1245 (41.0%) | 1203 (39.7%) | 2448 (40.4%) |
| Age at onset of diabetes (years) | | | |
| Number | 3034 | 3031 | 6065 |
| Mean (SD) | 51.29 (10.72) | 50.76 (10.73) | 51.02 (10.73) |
| Median | 51.00 | 51.00 | 51.00 |
| Min:Max | 13.0:87.0 | 17.0:91.0 | 13.0:91.0 |
| Baseline HbA1c (%) | | | |
| Number | 3033 | 3034 | 6067 |
| Mean (SD) | 7.64 (1.28) | 7.72 (1.32) | 7.68 (1.30) |
| Median | 7.50 | 7.50 | 7.50 |
| Min:Max | 5.0:11.5 | 4.9:13.3 | 4.9:13.3 |
| Baseline FPG (mmol/L) | | | |
| Number | 2947 | 2954 | 5901 |
| Mean (SD) | 8.20 (2.91) | 8.27 (2.82) | 8.23 (2.86) |
| Median | 7.50 | 7.60 | 7.60 |
| Min:Max | 2.3:28.1 | 2.5:25.1 | 2.3:28.1 |
| Baseline FPG (mg/dL) | | | |
| Number | 2947 | 2954 | 5901 |
| Mean (SD) | 147.79 (52.34) | 148.89 (50.86) | 148.34 (51.60) |
| Median | 135.11 | 136.91 | 136.91 |
| Min:Max | 41.4:506.2 | 45.0:45.2 | 41.4:506.2 |
| Baseline urinary albumin/creatinine ratio (mg/g) [n (%)] | | | |
| Number | 2994 | 2984 | 5978 |
| <30 mg/g (normoalbuminuria) | 2191 (73.2%) | 2250 (75.4%) | 4441 (74.3%) |
| ≥30 to <300 mg/g (microalbuminuria) | 596 (19.9%) | 552 (18.5%) | 1148 (19.2%) |
| ≥300 mg/g (macroalbuminuria) | 207 (6.9%) | 182 (6.1%) | 389 (6.5%) |
| Baseline estimated glomerular filtration rate (eGFR), n (%) | | | |
| Number | 3026 | 3029 | 6055 |
| ≥15 to <30 mL/min/1.73 m² (severe renal impairment) | 4 (0.1%) | 4 (0.1%) | 8 (0.1%) |
| ≥30 to <60 mL/min/1.73 m² (moderate renal impairment) | 744 (24.6%) | 655 (21.6%) | 1399 (23.1%) |
| ≥60 to <90 mL/min/1.73 m² (mild renal impairment) | 1603 (53.0%) | 1632 (53.9%) | 3235 (53.4%) |
| ≥90 mL/min/1.73 m² (normal) | 675 (22.3%) | 738 (24.4%) | 1413 (23.3%) |

SD: standard deviation,
HbA1: glycosylated hemoglobin A1c,
FPG: fasting plasma glucose.
eGFR: estimated glomerular filtration rate, calculated by the 4-variable modification of diet in renal disease (MDRD) formula using the serum creatinine, race, age, and gender of the patient: GFR (mL/min/1.73 m²) = 175 × serum creatinine (mg/dL)$^{-1.334}$ × age (years)$^{-0.203}$ × 1.212 [if black] × 0.742 [if female]

The majority of patients (>70%) in both treatment groups had a qualifying ACS within 90 days before randomization (Table 4). The most common type of qualifying ACS in both treatment groups was ST-segment elevation MI followed by non ST-segment elevation MI; less than 20% of patients experienced unstable angina. An equal percentage of patients in each treatment group (61%) underwent a percutaneous coronary revascularization for treatment of the ACS before entering the study. Heart function status and severity of angina as per New York Heart Association and Canadian Classification was similar in the two groups.

TABLE 4

Disease characteristics at baseline: History of qualifying acute coronary syndrome - Randomized population

| | Placebo (N = 3034) | Lixisenatide (N = 3034) | All (N = 6068) |
|---|---|---|---|
| Duration (days) between qualifying ACS and screening | | | |
| Number | 3031 | 3033 | 6064 |
| Mean (SD) | 64.11 (43.81) | 63.77 (43.35) | 63.94 (43.58) |
| Median | 52.00 | 52.00 | 52.00 |
| Min:Max | 3.0:220.0 | 3.0:251.0 | 3.0:251.0 |

TABLE 4-continued

Disease characteristics at baseline: History of qualifying
acute coronary syndrome - Randomized population

|  | Placebo (N = 3034) | Lixisenatide (N = 3034) | All (N = 6068) |
|---|---|---|---|
| Duration (days) between qualifying ACS and randomization | | | |
| Number | 3031 | 3033 | 6064 |
| Mean (SD) | 72.19 (43.85) | 71.83 (43.37) | 72.01 (43.61) |
| Median | 60.00 | 60.00 | 60.00 |
| Min:Max | 10.0:227.0 | 9.0:261.0 | 9.0:261.0 |
| Duration between qualifying ACS and randomization by the time category [n (%)] | | | |
| Number | 3031 | 3033 | 6064 |
| <30 days | 399 (13.2%) | 397 (13.1%) | 796 (13.1%) |
| ≥30 days-<60 days | 1099 (36.3%) | 1086 (35.8%) | 2185 (36.0%) |
| ≥60 days-<90 days | 675 (22.3%) | 722 (23.8%) | 1397 (23.0%) |
| ≥90 days | 858 (28.3%) | 828 (27.3%) | 1686 (27.8%) |
| Qualifying ACS [n (%)] | | | |
| Number | 3032 | 3033 | 6065 |
| ST-segment elevation MI | 1317 (43.4%) | 1349 (44.5%) | 2666 (44.0%) |
| Non ST-segment elevation MI | 11.83 (39.0%) | 1165 (38.4%) | 2348 (38.7%) |
| Unstable angina | 528 (17.4%) | 514 (16.9%) | 1042 (17.2%) |
| Unknown | 4 (0.1%) | 5 (0.2%) | 9 (0.1%) |
| Qualifying ACS: New York Heart Association (NYHA) class [n (%)] | | | |
| Number | 2936 | 2948 | 5884 |
| I | 1754 (59.7%) | 1816 (61.6%) | 3570 (60.7%) |
| II | 962 (32.8%) | 940 (31.9%) | 1902 (32.3%) |
| III | 190 (6.5%) | 166 (5.6%) | 356 (6.1%) |
| IV | 30 (1.0%) | 26 (0.9%) | 56 (1.0%) |
| Qualifying ACS: Worst severity of angina per Canadian Classification [n (%)] | | | |
| Number | 3020 | 3015 | 6035 |
| I | 610 (20.2%) | 611 (20.3%) | 1221 (20.2%) |
| II | 488 (16.2%) | 466 (15.5%) | 954 (15.8%) |
| III | 212 (7.0%) | 234 (7.8%) | 446 (7.4%) |
| IV | 122 (4.0%) | 145 (4.8%) | 267 (4.4%) |
| NA | 1588 (52.6%) | 1559 (51.7%) | 3147 (52.1%) |
| Patient underwent percutaneous coronary revascularization for qualifying ACS [n (%)] | | | |
| Number | 3032 | 3033 | 6065 |
| Yes | 1865 (61.5%) | 1875 (61.8%) | 3740 (61.7%) |
| No | 1167 (38.5%) | 1158 (38.2%) | 2325 (38.3%) |

SD: standard deviation,
ACS: acute coronary syndrome,
CABG: coronary artery bypass graft,
MI: myocardial infarction 3.1.4 Dosage and Duration of Exposure The starting dose of IMP was 10 μg QD for the first 2 weeks, after which the dose was increased to 20 μg QD and then maintained at that dose for the duration of the study. In case of intolerance, investigators were allowed to reduce the dose to 15 μg or 10 μg QD. The majority of patients in both groups received the maximal study dose of 20 μg QD (Table 5). More patients treated with placebo (96.5%) than with lixisenatide (85.5%) maintained the target dose of 20 μg QD until the end of the study.

TABLE 5

Number (%) of patients by final dose at the end of the
double-blind treatment period - Safety population

| Final Dose | Placebo (N = 3032) | Lixisenatide (N = 3031) |
|---|---|---|
| 5 μg | 0 | 5 (0.2%) |
| 10 μg | 86 (2.8%) | 312 (10.3%) |

TABLE 5-continued

Number (%) of patients by final dose at the end of the
double-blind treatment period - Safety population

| Final Dose | Placebo (N = 3032) | Lixisenatide (N = 3031) |
|---|---|---|
| 15 μg | 18 (0.6%) | 122 (4.0%) |
| 20 μg | 2926 (96.5%) | 2591 (85.5%) |
| 30 μg | 1 (<0.1%) | 0 |
| 40 μg | 1 (<0.1%) | 1 (<0.1%) |

Dose = Dose of lixisenatide or volume-matched placebo.
Note:
Percentages are calculated using the number of randomized and exposed population as the denominator.

The cumulative duration of treatment exposure was numerically higher for placebo versus lixisenatide. The median treatment exposure was 22.4 months for lixisenatide and 23.3 months for placebo (Table 6). More than 80% of patients in the lixisenatide group were treated for over 1 year, 66% for ≥1.5 years, and 45% for ≥2 years.

TABLE 6

Exposure to investigational product - Safety population

|  | Placebo (N = 3032) | Lixisenatide (N = 3031) |
|---|---|---|
| Cumulative duration of treatment exposure (patient years) | 5888.7 | 5690.2 |
| Duration of study treatment (days) | | |
| Number | 3007 | 3005 |
| Mean (SD) | 715.3 (330.7) | 691.6 (348.1) |
| Median | 698.0 | 673.0 |
| Min:Max | 1:1548 | 1:1572 |
| Duration of study treatment by category [n(%)] | | |
| Missing | 25 (0.8%) | 26 (0.9%) |
| <26 weeks | 255 (8.4%) | 348 (11.5%) |
| ≥26 to <52 weeks | 156 (5.1%) | 163 (5.4%) |
| ≥52 to <78 weeks | 498 (16.4%) | 484 (16.0%) |
| ≥78 to <104 weeks | 680 (22.4%) | 643 (21.2%) |
| ≥104 to <130 weeks | 561 (18.5%) | 545 (18.0%) |
| ≥130 to <156 weeks | 436 (14.4%) | 406 (13.4%) |
| ≥156 to <182 weeks | 261 (8.6%) | 255 (8.4%) |
| ≥182 to <208 weeks | 149 (4.9%) | 143 (4.7%) |
| ≥208 weeks | 11 (0.4%) | 18 (0.6%) |
| Cumulative duration of study treatment by category [n (%)] | | |
| ≥26 weeks | 2752 (90.8%) | 2657 (87.7%) |
| ≥52 weeks | 2596 (85.6%) | 2494 (82.3%) |
| ≥78 weeks | 2098 (69.2%) | 2010 (66.3%) |
| ≥104 weeks | 1418 (46.8%) | 1367 (45.1%) |
| ≥130 weeks | 857 (28.3%) | 822 (27.1%) |
| ≥156 weeks | 421 (13.9%) | 416 (13.7%) |
| ≥182 weeks | 160 (5.3%) | 161 (5.3%) |
| ≥208 weeks | 11 (0.4%) | 18 (0.6%) |

SD: standard deviation.
IMP: investigational medicinal product.
Note:
Patients are considered in the group of treatment they actually received at randomization.
Duration of exposure = (date of the last double-blind IMP injection − date of the first double-blind IMP injection) + 1 day.

3.2 Efficacy 3.2.1 Primary Efficacy Endpoint

The percentage of patients with a primary CV endpoint event (13.4% and 13.2% for lixisenatide and placebo, respectively) as well as the incidence per 100-patient years (6.39 and 6.31 for lixisenatide and placebo, respectively) were comparable between treatment groups (Table 7).

The hazard ratio for lixisenatide versus placebo was 1.017 with an associated 2-sided 95% CI of 0.886 to 1.168. The upper bound of the 2-sided 95% CI estimated from the Cox model was below the pre-specified non-inferiority margin of 1.3 but above 1.0; thus, lixisenatide demonstrated non-inferiority but did not show superiority versus placebo for the primary CV endpoint.

The percentages of each type of primary endpoints included in the primary composite endpoint by treatment group were consistent with the results of the composite endpoint (Table 7).

Individual Primary Endpoints

The results of the analyses of the time to the first occurrence of each individual component of the composite primary endpoint are presented in a forest plot (FIG. 2). Overall, these results are concordant with the composite primary endpoint. Numerically more "stroke" events were seen in the lixisenatide group; however, the imbalance in the number of events (67 for lixisenatide versus 60 for placebo)

TABLE 7

Analysis of the primary cardiovascular endpoint (time to the first occurrence of the composite of cardiovascular death, non-fatal myocardial infarction, non-fatal stroke, or hospitalization for unstable angina) - ITT population

|  | Placebo (N = 3034) | Lixisenatide (N = 3034) | Hazard ratio (95% CI)$^c$ | Log-rank test p-value |
|---|---|---|---|---|
| Composite of CV death, non-fatal MI, non-fatal stroke, or hospitalization for unstable angina* |  |  | 1.017 (0.886, 1.168) | 0.8542 |
| Number of patients with event (%) | 399 (13.2%) | 406 (13.4%) | — | — |
| Total patient years for the event$^a$ | 6328.2 | 6356.8 | — | — |
| Incidence rate per 100 patient years$^b$ | 6.31 | 6.39 | — | — |
| Type of the first event of the composite endpoint |  |  |  |  |
| CV death | 93 (3.1%) | 88 (2.9%) | — | — |
| Non-fatal MI | 247 (8.1%) | 255 (8.4%) | — | — |
| Non-fatal stroke | 49 (1.6%) | 54 (1.8%) | — | — |
| Hospitalization for unstable angina | 10 (0.3%) | 9 (0.3%) | — | — |

*Only CAC positively adjudicated events are included.
CV: cardiovascular, MI: myocardial infarction, CI: confidence interval.
$^a$Calculated as time from randomization date to the first event date or censoring date (the end of study date) for patients who had no events.
$^b$Calculated as number of patients with an event divided by total patient years for the event and multiplied by 100.
$^c$Hazard ratio of lixisenatide versus placebo estimated using Cox proportional hazards model based on ITT population, with treatment (lixisenatide, placebo), and region (North America, South and Central America, Western Europe, Eastern Europe, Africa/Near East, and Asia/Pacific) as covariates, and the associated two-sided 95% CI.
In case of multiple events ocurred on the same date, event is counted in the categories following the order of CV death, non-fatal MI, non-fatal stroke, hospitalization for unstable angina.

Kaplan-Meier cumulative curves of time from randomization to the first primary CV endpoint event for lixisenatide and placebo were superimposed over the majority of the study period (FIG. 1).

Analysis of MACE Endpoint

The results of the composite MACE endpoint, which excluded "hospitalization for unstable angina", showed a result consistent with the primary endpoint with similar incidence rates between treatment groups (Table 8). A neutral HR for lixisenatide versus placebo was observed with an associated upper bound of the 2-sided 95% CI below 1.3.

was small and the 95% CI was wide and crossed unity. In addition, fatal strokes were reported less frequently in the lixisenatide group than in the placebo group (Table 13).

3.2.2 Other Key Efficacy Endpoints 3.2.2.1 Secondary CV Endpoints

Consistent with the analyses of the primary CV endpoint, the event rates of composite endpoints adding "hospitalization for heart failure" or both "hospitalization for heart failure" and "coronary revascularization" were comparable between treatments. The hazard ratio, 95% CI, and descriptive p-values for each of the composite endpoints are presented in Table 9.

TABLE 8

Analysis of Major Adverse Cardiac Event (MACE) (time to the first occurrence of the composite of cardiovascular death, non-fatal myocardial infarction, or non-fatal stroke) - ITT population

|  | Placebo (N = 3034) | Lixisenatide (N = 3034) | Hazard ratio (95% CI)$^c$ | Log-rank test p-value |
|---|---|---|---|---|
| Composite of CV death, non-fatal MI, or non-fatal stroke* |  |  | 1.02 (0.887, 1.172) | 0.8234 |
| Number of patients with event (%) | 392 (12.9%) | 400 (13.2%) | — | — |
| Total patient years for the event$^a$ | 6340.2 | 6368.7 | — | — |
| Incidence rate per 100 patient years$^b$ | 6.18 | 6.28 | — | — |

CV: cardiovascular, MI: myocardial infarction, CI: confidence interval.
*Only CAC positively adjudicated events are included.
$^a$Calculated as time from randomization date to the first event date or censoring date (the end of study date) for patients who had no events.
$^b$Calculated as number of patients with an event divided by total patient years for the event and multiplied by 100.
$^c$Hazard ratio of lixisenatide versus placebo estimated using Cox proportional hazards model based on ITT population, with treatment (lixisenatide, placebo), and region (North America, South and Central America, Western Europe, Eastern Europe, Africa/Near East, and Asia/Pacific) as covariates, and the associated two-sided 95% CI.

TABLE 9

Analysis of the secondary composite cardiovascular endpoints - ITT population

|  | Placebo (N = 3034) | Lixisenatide (N = 3034) | Hazard ratio (95% CI)[c] | Log-rank test p-value |
|---|---|---|---|---|
| Composite of CV death, non-fatal MI, non-fatal stroke, hospitalization for unstable angina, or hosptalization for heart failure* |  |  | 0.968 (0.851, 1.102) | 0.5823 |
| Number of patients with event (%) | 469 (15.5%) | 456 (15.0%) | — | — |
| Total patient years for the event[a] | 6209.2 | 6269.6 | — | — |
| Incidence rate per 100 patient years[b] | 7.55 | 7.27 | — | — |
| Composite of CV death, non-fatal MI, non-fatal stroke, hospitalization for unstable angina, hospitalization for heart failure, or coronary revascularization procedure* |  |  | 0.997 (0.895, 1.111) | 0.963 |
| Number of patients with event (%) | 659 (21.7%) | 661 (21.8%) | — | — |
| Total patient years for the event[a] | 5904.5 | 5946.9 | — | — |
| Incidence rate per 100 patient years[b] | 11.16 | 11.12 | — | — |

CV: cardiovascular, MI: myocardial infarction, CI: confidence interval.
*Only CAC positively adjudicated events are included.
[a]Calculated as time from randomization date to the first event date or censoring date (the end of study date) for patients who had no events.
[b]Calculated as number of patients with an event divided by total patient years for the event and multiplied by 100.
[c]Hazard ratio of lixisenatide versus placebo estimated using Cox proportional hazards model based on ITT population, with treatment (lixisenatide, placebo), and region (North America, South and Central America, Western Europe, Eastern Europe, Africa/Near East, and Asia/Pacific) as covariates, and the associated two-sided 95% CI.

Individual Secondary Endpoints

The results of analyses of the time to the first occurrence of each individual component of the composite secondary endpoints are presented in FIG. 3, including MACE+"hospitalization for heart failure", and MACE+"hospitalization for heart failure" or "coronary revascularization".

The hazard ratios for lixisenatide versus placebo and the associated 2-sided 95% CI suggest that treatment with lixisenatide, as compared to placebo, did not increase or decrease the occurrence of hospitalization for heart failure or both hospitalizations for heart failure and coronary revascularization.

3.2.2.2 Urinary Albumin/Creatinine Ratio

UACR was measured at Weeks 0, 24, 76, 108 and End of Study and percent changes from baseline to Week 108 are summarized (Table 10). Geometric mean values at baseline were similar in the two treatment groups. Geometric mean UACR increased from baseline to Week 108 in both treatment groups, but showed a smaller increase in the lixisenatide group as compared to the placebo group (the difference between lixisenatide versus placebo in the percent change from baseline of UACR was −0.10% with a 95% CI of −0.17 to −0.03).

TABLE 10

Analysis of percent change in urinary albumin/creatinine ratio in US units (mg/g) from baseline to Week 108 (LOCF) - ITT population

| Urinary albumin/creatinine ratio (mg/g) | Placebo (N = 3034) | Lixisenatide (N = 3034) |
|---|---|---|
| Baseline |  |  |
| Number | 2830 | 2803 |
| Geometric Mean (SD) | 17.36 (26.53) | 16.04 (23.32) |
| Median | 10.36 | 10.03 |
| Min:Max | 1.24:76025.07 | 1.77:155074.87 |
| Week 108 (LOCF) |  |  |
| Number | 2830 | 2803 |
| Geometric Mean (SD) | 22.99 (39.16) | 19.90 (31.36) |
| Median | 13.39 | 11.89 |
| Min:Max | 2.15:19710.58 | 1.44:16047.83 |

TABLE 10-continued

Analysis of percent change in urinary albumin/creatinine ratio in US units (mg/g) from baseline to Week 108 (LOCF) - ITT population

| Urinary albumin/creatinine ratio (mg/g) | Placebo (N = 3034) | Lixisenatide (N = 3034) |
|---|---|---|
| Percent change from baseline to Week 108 (LOCF[a]) |  |  |
| Based on geometric mean | 0.32 | 0.24 |
| Based on geometric mean estimated from ANCOVA model[b] (SE) | 0.34 (0.03) | 0.24 (0.03) |
| Lixisenatide versus placebo[c] (SE) |  | −0.10 (0.04) |
| 95% CI |  | (−0.17, −0.03) |

SD: standard deviation, LOCF: last observation carried forward, SE: standard error, CI: confidence interval.
[a]In case of missing measurements at Week 108, the LOCF procedure is used by taking the last available post-baseline urinary albumin/creatinine ratio before Week 108 as the value at Week 108, regardless of treatment discontinuation or not.
[b]The urinary albumin/creatinine ratio are first log-transformed. Then the change from baseline is analyzed using ANCOVA model with treatment (lixisenatide, placebo), region, intake of ACE inhibitors at baseline (yes or no) and intake of Angiotensin II Receptor Blockers at baseline (ARB) (yes or no) as fixed effects and using the baseline urinary albumin/creatinine ratio as a covariate. Results in the log scale are back-transformed to provide the estimates of the geometric means.
[c]Calculated based on the estimates from the ANCOVA model.
Region: North America, South and Central America, Western Europe, Eastern Europe, Africa/Near East, and Asia/Pacific.

3.2.2.3 Change from Baseline in HbA1c

Patients in both treatment groups had a comparable mean HbA1c at baseline (7.72% for lixisenatide versus 7.64% for placebo). The mean HbA1c was reduced in both treatment groups over the course of the study. A greater reduction was seen in the lixisenatide than in the placebo group at each observation over the entire study period (FIG. 4).

3.3 Safety 3.3.1 TEAEs

Note: as stated in the statistical section, this table does nor include the events reported in the specific CV AE forms for "Myocardial infarction (MI) or hospitalization for unstable angina", "Stroke", "Hospitalization for heart failure", or "Coronary revascularization procedure", regardless of adjudication results, seriousness or drug-relationship, because all these events were reported as endpoints.

The proportion of patients with at least 1 TEAE was numerically higher in the lixisenatide group as compared to the placebo group, while the proportion of patients with a serious TEAE was numerically higher in the placebo group as compared to the lixisenatide group (Table 1). The percentage of patients with TEAEs leading to death was comparable between treatments.

More patients discontinued IMP due to an AE in the lixisenatide group than in the placebo group. As previously observed in lixisenatide Phase 3 studies, the imbalance was primarily due to the higher frequency of TEAEs of nausea and vomiting, known side effects of GLP-1 receptor agonists.

TABLE 11

Overview of on-treatment adverse events - safety population

|  | Placebo (N = 3032) | Lixisenatide (N = 3031) |
|---|---|---|
| Patients with any on-treatment AE | 2321 (76.6%) | 2447 (80.7%) |
| Patients with any serious on-treatment AE | 669 (22.1%) | 625 (20.6%) |
| Patients with any on-treatment AE leading to death | 64 (2.1%) | 74 (2.4%) |
| Patients with any on-treatment AE leading to permanent treatment discontinuation | 217 (7.2%) | 347 (11.4%) |

AE: adverse event.
On-treatment AE: AEs that developed or worsened (according to the Investigator opinion) or became serious during the on-treatment period.
On-treatment period = the time from the first IMP dose intake until 3 days after treatment discontinuation.
n (%) = number and percentage of patients with at least one on-treatment AE.

3.3.2 Deaths

All deaths were reviewed by the CAC and the primary cause of death was adjudicated by the CAC regardless of the investigators' diagnosis. The incidence of CV and non-CV deaths, or unknown deaths (due to insufficient information for adjudication) according to the CAC adjudication was summarized for on-treatment and on-study periods.

The incidence of all deaths on-treatment and on-study was comparable between lixisenatide and placebo (Table 12), as were the on-study deaths by primary cause of death as adjudicated by the CAC (Table 13).

TABLE 12

Number (%) of patients who died by study period (on-study, on-treatment, post-study) and primary cause of death as adjudicated by the CAC - safety population

|  | Placebo (N = 3032) | Lixisenatide (N = 3031) |
|---|---|---|
| Death on-study[a] | 223 (7.4%) | 211 (7.0%) |
| CV death | 158 (5.2%) | 156 (5.1%) |
| Non-CV death | 58 (1.9%) | 46 (1.5%) |
| Unknown | 7 (0.2%) | 9 (0.3%) |
| Death on-treatment[b] | 96 (3.2%) | 93 (3.1%) |
| CV death | 86 (2.8%) | 76 (2.5%) |
| Non-CV death | 10 (0.3%) | 13 (0.4%) |
| Unknown | 0 | 4 (0.1%) |
| Death post-study[c] | 0 | 1 (<0.1%) |

CAC: cardiovascular events adjudication committee, CV: cardiovascular.
[a]On-study period = time from the randomization until the study end date for a patient.
[b]On-treatment period = the time from the first IMP dose intake until 3 days after treatment discontinuation.
[c]Includes deaths that occurred after the end of the study and reported in the database.

TABLE 13

Number (%) of patients who died during the on-study period by primary cause of death as adjudicated by the CAC - safety population

| Type | Placebo (N = 3032) | Lixisenatide (N = 3031) |
|---|---|---|
| Any death | 223 (7.4%) | 211 (7.0%) |
| Cardiovascular death | 158 (5.2%) | 156 (5.1%) |
| Fatal Myocardial Infarction | 23 (0.8%) | 35 (1.2%) |
| Heart failure | 24 (0.8%) | 18 (0.6%) |
| Sudden death | 58 (1.9%) | 66 (2.2%) |
| Witnessed or last seen alive LT 1 hr | 41 (1.4%) | 44 (1.5%) |
| Last seen alive GE 1 hr and LT 24 hrs | 17 (0.6%) | 22 (0.7%) |
| Presumed sudden death | 4 (0.1%) | 4 (0.1%) |
| Presumed CV death | 25 (0.8%) | 12 (0.4%) |
| Fatal stroke | 18 (0.6%) | 13 (0.4%) |
| Ischemic | 8 (0.3%) | 6 (0.2%) |
| Ischemic with hemorrhagic conversion | 1 (<0.1%) | 2 (<0.1%) |
| Hemorrhagic | 8 (0.3%) | 3 (<0.1%) |
| Clinical | 1 (<0.1%) | 2 (<0.1%) |
| Fatal pulmonary embolism | 1 (<0.1%) | 0 |
| CV Procedural | 3 (<0.1%) | 6 (0.2%) |
| CABG | 1 (<0.1%) | 4 (0.1%) |
| PCI/Stenting | 0 | 1 (<0.1%) |
| Valvular | 0 | 0 |
| Other CV Procedural | 2 (<0.1%) | 1 (<0.1%) |
| Other cardiovascular death | 2 (<0.1%) | 2 (<0.1%) |
| Non Cardiovascular death | 58 (1.9%) | 46 (1.5%) |
| Infection | 17 (0.6%) | 13 (0.4%) |
| Malignancy | 21 (0.7%) | 22 (0.7%) |
| Pulmonary | 6 (0.2%) | 2 (<0.1%) |
| Gastro intestinal | 10 (0.3%) | 3 (<0.1%) |
| Renal | 2 (<0.1%) | 1 (<0.1%) |
| Accidental | 0 | 1 (<0.1%) |
| Suicide | 1 (<0.1%) | 1 (<0.1%) |
| Diabetes-related | 1 (<0.1%) | 0 |
| Other Non-CV death | 0 | 3 (<0.1%) |
| Unknown cause of death | 7 (0.2%) | 9 (0.3%) |

CAC: cardiovascular events adjudication committee.
On-study period = time from the randomization until the study end date for a patient.

3.3.3 SAEs

Table 14 is a modified serious TEAE table due to KRM space limitation. It includes serious TEAEs (n/%) by primary system organ class (SOC). Serious TEAEs by HLGT and HLT are displayed only if the incidence was ≥0.4% and was also higher in the lixisenatide than in the placebo group.

The incidence of serious TEAEs was well-balanced between treatment groups, Serious TEAEs were reported in 20.6% and 22.1% of patients in the lixisenatide and placebo groups, respectively (Table 14).

The frequencies of categories of serious TEAEs were generally similar between treatments or numerically lower in the lixisenatide group as compared to the placebo group. An exception was serious TEAEs categorized as gallbladder disorders (32 patients [1.1%] versus 19 [0.6%] for lixisenatide versus placebo), including cholecystitis (acute or chronic) and cholelithiasis.

TABLE 14

Number (%) of patients with serious on-treatment adverse events presented by primary SOC, HLGT, HLT, and PT - safety population

| PRIMARY SYSTEM ORGAN CLASS<br>HLGT: High Level Group Term<br>HLT: High Level Term<br>Preferred Term n(%) | Placebo<br>(N = 3032) | Lixisenatide<br>(N = 3031) |
|---|---|---|
| Any class | 669 (22.1%) | 625 (20.6%) |
| INFECTIONS AND INFESTATIONS | 186 (6.1%) | 173 (5.7%) |
| HLGT: Infections - pathogen unspecified | 154 (5.1%) | 150 (4.9%) |
| HLT: Abdominal and gastrointestinal infections | 20 (0.7%) | 25 (0.8%) |
| NEOPLASMS BENIGN, MALIGNANT AND UNSPECIFIED (INCL CYSTS AND POLYPS) | 61 (2.0%) | 72 (2.4%) |
| HLGT: Gastrointestinal neoplasms malignant and unspecified | 16 (0.5%) | 19 (0.6%) |
| HLT: Colorectal neoplasms malignant | 7 (0.2%) | 13 (0.4%) |
| HLGT: Reproductive neoplasms male malignant and unspecified | 9 (0.3%) | 12 (0.4%) |
| HLT: Prostatic neoplasms malignant | 8 (0.3%) | 12 (0.4%) |
| BLOOD AND LYMPHATIC SYSTEM DISORDERS | 14 (0.5%) | 14 (0.5%) |
| ENDOCRINE DISORDERS | 3 (<0.1%) | 2 (<0.1%) |
| METABOLISM AMD NUTRITION DISORDERS | 57 (1.9%) | 33 (1.1%) |
| HLGT: Electrolyte and fluid balance conditions | 12 (0.4%) | 15 (0.5%) |
| PSYCHIATRIC DISORDERS | 5 (0.2%) | 9 (0.3%) |
| NERVOUS SYSTEM DISORDERS | 53 (1.7%) | 47 (1.6%) |
| EYE DISORDERS | 13 (0.4%) | 9 (0.3%) |
| EAR AND LABYRINTH DISORDERS | 4 (0.1%) | 5 (0.2%) |
| CARDIAC DISORDERS | 107 (3.5%) | 83 (2.7%) |
| HLGT: Cardiac arrhythmias | 71 (2.3%) | 49 (1.6%) |
| HLT: Ventricular arrhythmias and cardiac arrest | 13 (0.4%) | 14 (0.5%) |
| VASCULAR DISORDERS | 71 (2.3%) | 59 (1.9%) |
| HLGT: Arteriosclerosis, stenosis, vascular insufficiency and necrosis | 19 (0.6%) | 19 (0.6%) |
| HLT: Peripheral vasoconstriction, necrosis and vascular insufficiency | 13 (0.4%) | 14 (0.5%) |
| RESPIRATORY, THORACIC AND MEDIASTINAL DISORDERS | 58 (1.9%) | 58 (1.9%) |
| GASTROINTESTINAL DISORDERS | 81 (2.7%) | 66 (2.2%) |
| HEPATOBILIARY DISORDERS | 28 (0.9%) | 36 (1.2%) |
| HLGT: Gallbladder disorders | 19 (0.6%) | 32 (1.1%) |
| HLT: Cholecystitis and cholelithiasis | 19 (0.6%) | 31 (1.0%) |
| SKIN AND SUBCUTANEOUS TISSUE DISORDERS | 18 (0.6%) | 14 (0.5%) |
| MUSCULOSKELETAL AND CONNECTIVE TISSUE DISORDERS | 35 (1.2%) | 32 (1.1%) |
| HLGT: Joint disorders | 9 (0.3%) | 13 (0.4%) |
| RENAL AND URINARY DISORDERS | 48 (1.6%) | 48 (1.6%) |
| HLGT: Renal disorders (excl nephropathies) | 32 (1.1%) | 33 (1.1%) |
| HLT: Renal failure and impairment | 31 (1.0%) | 32 (1.1%) |
| REPRODUCTIVE SYSTEM AND BREAST DISORDERS | 5 (0.2%) | 13 (0.4%) |
| GENERAL DISORDERS AND ADMINISTRATION SITE CONDITIONS | 58 (1.9%) | 64 (2.1%) |
| HLGT: General system disorders NEC | 51 (1.7%) | 54 (1.8%) |
| HLT: Pain and discomfort NEC | 44 (1.5%) | 49 (1.6%) |
| INVESTIGATIONS | 19 (0.6%) | 10 (0.3%) |
| INJURY, POISONING AND PROCEDURAL COMPLICATIONS | 50 (1.6%) | 44 (1.5%) |
| HLGT: Injuries NEC | 16 (0.5%) | 17 (0.6%) |
| HLT: Non-site specific injuries NEC | 10 (0.3%) | 11 (0.4%) |
| SURGICAL AND MEDICAL PROCEDURES | 6 (0.2%) | 6 (0.2%) |
| SOCIAL CIRCUMSTANCES | 0 | 1 (<0.1%) |

Note:
SOC: system organ class, HLGT: high level group term, HLT: high level term, On-treatment AE: AEs that developed or worsened (according to the Investigator opinion) or became serious during the on-treatment period. On-treatment period = the time from the first IMP dose intake until 3 days after treatment discontinuation. n (%) = number and percentage of patients with at least one on-treatmeant AE.

3.3.4 Other Significant Adverse Events

3.3.41 Pancreatis

Pancreatitis occurred infrequently in both treatment groups (Table 15), and the percentage of patients with suspected pancreatitis sent for adjudication was similar between lixisenatide and placebo. Fewer patients in the lixisenatide than in the placebo group had TEAEs of any type of pancreatitis as confirmed by the PSAC.

TABLE 15

Summary of events sent to PSAC for pancreatitis adjudication during the on-treatment period - safety population

| Type | Placebo<br>(N = 3032) | Lixisenatide<br>(N = 3031) |
|---|---|---|
| Total patient years of exposure | 5942.69 | 5757.09 |
| Events sent to PSAC for adjudication | | |
| Number of patients with events | 32 (1.1%) | 36 (1.2%) |
| Number of events | 34 | 47 |

TABLE 15-continued

Summary of events sent to PSAC for pancreatitis adjudication during the on-treatment period - safety population

| Type | Placebo (N = 3032) | Lixisenatide (N = 3031) |
|---|---|---|
| Events adjudicated as "Yes" for pancreatitis by PSAC | | |
| Number of patients with events | 8 (0.3%) | 5 (0.2%) |
| Number of events | 8 | 5 |
| Events adjudicated as "Yes" for acute pancreatitis by PSAC | | |
| Number of patients with events | 7 (0.2%) | 2 (<0.1%) |
| Number of events | 7 | 2 |
| Events adjudicated as "Yes" for acute on chronic pancreatitis by PSAC | | |
| Number of patients with events | 0 | 1 (<0.1%) |
| Number of events | 0 | 1 |
| Events adjudicated as "Yes" for chronic pancreatitis by PSAC | | |
| Number of patients with events | 1 (<0.1%) | 2 (<0.1%) |
| Number of events | 1 | 2 |
| Events adjudicated as "Yes" for unknown pancreatitis by PSAC | | |
| Number of patients with events | 0 | 0 |
| Number of events | 0 | 0 |
| Events adjudicated as "No" for pancreatitis by PSAC | | |
| Number of patients with events | 24 (0.8%) | 32 (1.1%) |
| Number of events | 25 | 42 |
| Events adjudicated as Insufficient documentation for event determination by PSAC | | |
| Number of patients with events | 1 (<0.1%) | 0 |
| Number of events | 1 | 0 |

PSAC: pancreatic safety assessment committee.
On-treatment period = the time from the first IMP dose intake until 3 days after treatment discontinuation.
Patient years of exposure is calculated as time from the first to the last injection of IMP plus 3 days.

3.3.42 Pancreatic Cancer

Pancreatic cancer occurred infrequently during the combined on-treatment and post-treatment periods (Table 16). The incidence of observed pancreatic malignancy confirmed by the PSAC was lower in the lixisenatide than in the placebo group (3 patients [<0.1%] versus 9 [0.3%], respectively).

No patients in the lixisenatide and two in the placebo group had pancreatic cancers that were considered as possibly related to study treatment by the PSAC (Table 17).

TABLE 16

Summary of events sent to PSAC for pancreatic neoplasms adjudication during the combined on-treatment and post-treatment periods - safety population

| Type | Placebo (N = 3032) | Lixisenatide (N = 3031) |
|---|---|---|
| Total patient years of follow up | 6690.75 | 6730.22 |
| Events sent to PSAC for adjudication | | |
| Number of patients with events | 11 (0.4%) | 5 (0.2%) |
| Number of events | 11 | 5 |
| Events adjudicated as malignant pancreatic neoplasms by PSAC | | |
| Number of patients with events | 9 (0.3%) | 3 (<0.1%) |
| Number of events | 9 | 3 |

TABLE 16-continued

Summary of events sent to PSAC for pancreatic neoplasms adjudication during the combined on-treatment and post-treatment periods - safety population

| Type | Placebo (N = 3032) | Lixisenatide (N = 3031) |
|---|---|---|
| Events adjudicated as benign pancreatic neoplasms by PSAC | | |
| Number of patients with events | 0 | 1 (<0.1%) |
| Number of events | 0 | 1 |
| Events adjudicated as Insufficient documentation for event determination by PSAC | | |
| Number of patients with events | 1 (<0.1%) | 1 (<0.1%) |
| Number of events | 1 | 1 |

PSAC: pancreatic safety assessment committee.
On-treatment period = the time from the first IMP dose intake until 3 days after treatment discontinuation.
Post-treatment period = the time starting 4 days after the last administration of IMP (after the on-treatment period).
Patient years of follow up is calculated as time from the first dosing to the last contact date or death.

3.3.4.3 Other Malignancy Events and Unspecified Tumors

TABLE 17

Number (%) of patients with events adjudicated as malignant pancreatic neoplasms by PSAC by causal relationship during the combined on-treatment and post-treatment periods - safety population

| Number of patients with events adjudicated as malignant pancreatic neoplasms by PSAC | Placebo (N = 3032) | Lixisenatide (N = 3031) |
|---|---|---|
| Related | 0 | 0 |
| Possibly related | 2 (<0.1%) | 0 |
| Unlikely related | 3 (<0.1%) | 2 (<0.1%) |
| Not related | 4 (0.1%) | 1 (<0.1%) |

PSAC: pancreatic safety assessment committee.
On-treatment period = the time from the first IMP dose intake until 3 days after treatment discontinuation.
Post-treatment period = the time starting 4 days after the last administration of IMP (after the on-treatment period).

Using a standardized MedDRA Query, the SMQ "Malignant or unspecified tumors" was used for the analyses. The presented AEs include cancers and unspecified neoplasm (eg, nodules and neoplasms). Five pre-specified categories of malignancies are summarized in the table.

A numerically greater incidence of any type of malignancy was noted for lixisenatide treatment (3.5%) as compared to placebo (2.9%) (Table 18). For the individual categories, reported events were balanced for thyroid, lung, and breast cancers. Numerically more events of colorectal and prostate cancers were reported in the lixisenatide as compared to the placebo group.

No event of thyroid C-cell tumor or hyperplasia was reported in the study.

TABLE 18

Number (%) of malignancies during the combined on-treatment and post-treatment periods - safety population

| | Placebo (N = 3032) | Lixisenatide (N = 3031) |
|---|---|---|
| Any patients with malignancy event | 89/3032 (2.9%) | 105/3031 (3.5%) |
| Thyroid | 8/3032 (0.3%) | 11/3031 (0.4%) |
| Lung | 12/3032 (0.4%) | 8/3031 (0.3%) |

TABLE 18-continued

Number (%) of malignancies during the combined on-treatment and post-treatment periods - safety population

|  | Placebo (N = 3032) | Lixisenatide (N = 3031) |
|---|---|---|
| Colorectal | 11/3032 (0.4%) | 17/3031 (0.6%) |
| Breast[a] | 3/937 (0.3%) | 3/920 (0.3%) |
| Prostate[b] | 8/2095 (0.4%) | 14/2111 (0.7%) |

On-treatment period = the time from the first IMP dose intake until 3 days after treatment discontinuation.
Post-treatment period = the time starting 4 days after the last administration of IMP (after the on-treatment period).
The overall malignancy will be defined by preferred terms in the MedDRA SMQ of Malignant orunspecified tumors (#20000091). Additional classifications by subcategories (thyroid, lung, colorectal, breast, and prostate) will be done based on this SMQ.
[a]Events of breast cancer/malignancy will be summarized for females only.
[b]Events of prostate cancer/malignancy for males only.

3.3.4.4 Severe Hypoglycemia

The incidence of severe symptomatic hypoglycemia was low in both treatment groups as assessed by either the event-rate per 100 patient-years or the percentage of patients with events (Table 19). Fewer patients treated with lixisenatide than with placebo experienced severe symptomatic hypoglycemia; event rates per 100-patient years were 0.3 and 0.6 in the lixisenatide and placebo group, respectively.

TABLE 19

Summary of severe symptomatic hypoglycemia during the on-treatment period - safety population

| Type | Placebo (N = 3032) | Lixisenatide (N = 3031) |
|---|---|---|
| Total patient years | 5942.69 | 5757.09 |
| *Any severe symptomatic hypoglycemia* | | |
| Number of patients with events[a] | 24 (0.8%) | 14 (0.5%) |
| Number of patients with events per 100 patient years[b] | 0.4 | 0.2 |
| Number of events | 37 | 16 |
| Number of events per 100 patient years[c] | 0.6 | 0.3 |
| *Blood glucose <36 mg/dL* | | |
| Number of patients with events[a] | 14 (0.5%) | 4 (0.1%) |
| Number of patients with events per 100 patient years[b] | 0.2 | 0.1 |
| Number of events | 25 | 5 |
| Number of events per 100 patient years[c] | 0.4 | 0.1 |
| *No blood glucose reported[d]* | | |
| Number of patients with events[a] | 12 (0.4%) | 10 (0.3%) |
| Number of patients with events per 100 patient years[b] | 0.2 | 0.2 |
| Number of events | 12 | 11 |
| Number of events per 100 patient years[c] | 0.2 | 0.2 |

Symptomatic hypoglycemia = symptomatic hypoglycemia as defined per protocol.
On-treatment period = the time from the first IMP dose intake until 3 days after treatment discontinuation.
[a]Percentages are calculated using the safety population as the denominator.
[b]Number of patients with events per 100 patient years = number of patients with events * 100/total exposure + 3 days in patient years.
[c]Number of events per 100 patient years = number of events * 100/total exposure + 3 days in patient years.
[d]Events associated with prompt recovery after oral carbohydrate, intravenous glucose, or glucagon administration, if plasma glucose measurement is not available or obtained after the event was treated.

The invention claimed is:

1. A method of reducing urinary albumin excretion in a type 2 diabetes mellitus patient with albumunuria, said method comprising
selecting a type 2 diabetes mellitus patient with albuminuria, and administering lixisenatide or a pharmaceutically acceptable salt thereof to the patient in need thereof, thereby reducing albumin excretion in the patient.

2. The method of claim 1, wherein the patient has microalbuminuria.

3. The method of claim 1, wherein the patient has a urinary albumin to creatinine ratio (UACR) of ≥30 mg/g to <300 mg/g.

4. The method of claim 1, wherein the patient has a urinary albumin to creatinine ratio (UACR) of ≥300 mg/g.

5. The method of claim 1, wherein the patient has a glomerular filtration rate (GFR) of ≥60 mL/min/1.73 m² to <90 mL/min/1.73 m².

6. The method of claim 1, wherein the patient has a glomerular filtration rate (GFR) of ≥30 mL/min/1.73 m² to <60 mL/min/1.73 m².

7. The method of claim 1, wherein the patient has a glomerular filtration rate (GFR) of ≥15 mL/min/1.73 m² to <30 mL/min/1.73 m².

8. The method of claim 1, wherein the patient receives lixisenatide in combination with
an insulin or a pharmaceutically acceptable salt thereof.

9. The method of claim 1, wherein prior to the onset of treatment with lixisenatide, the patient has a HbA1c value of 7% to 10%.

10. The method of claim 1, wherein the patient has macroalbuminuria.

11. The method of claim 1, wherein prior to the onset of treatment with lixisenatide, the patient's type 2 diabetes mellitus is not adequately controlled.

12. The method of claim 1, wherein the lixisenatide is administered subcutaneously.

13. The method of claim 1, wherein the lixisenatide is administered in a daily dose of 5 μg to 20 μg.

14. The method of claim 11, wherein the patient's type 2 diabetes mellitus is not adequately controlled on insulin or a pharmaceutically acceptable salt thereof.

15. The method of claim 1, wherein the patient receives lixisenatide in combination with metformin or a pharmaceutically acceptable salt thereof.

16. The method of claim 1, wherein the patient receives lixisenatide in combination with a glinide or a pharmaceutically acceptable salt thereof.

17. The method of claim 1, wherein the patient receives lixisenatide in combination with a sulfonylurea or a pharmaceutically acceptable salt thereof.

* * * * *

SEQUENCE LISTING

<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<223> OTHER INFORMATION: Lixisenatide
<220> FEATURE:
<221> NAME/KEY: MOD_RES
<222> LOCATION: (44)..(44)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Artificial Sequence
<220> FEATURE:

```
<223> OTHER INFORMATION: Exendin-4
<220> FEATURE:
<221> NAME/KEY: MOD_RES
<222> LOCATION: (39)..(39)
<223> OTHER INFORMATION: AMIDATION

<400> SEQUENCE: 2

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35
```